(12) United States Patent
Tran

(10) Patent No.: US 10,052,026 B1
(45) Date of Patent: Aug. 21, 2018

(54) SMART MIRROR

(71) Applicant: Bao Tran, Saratoga, CA (US)

(72) Inventor: Bao Tran, Saratoga, CA (US)

(*) Notice: Subject to any disclaimer, the term of this patent is extended or adjusted under 35 U.S.C. 154(b) by 0 days.

(21) Appl. No.: 15/451,321

(22) Filed: Mar. 6, 2017

(51) Int. Cl.

| | | |
|---|---|---|
| A61B 5/0245 | (2006.01) |
| A61B 5/15 | (2006.01) |
| A61B 5/103 | (2006.01) |
| A61B 5/00 | (2006.01) |
| G06T 19/20 | (2011.01) |
| G06K 9/00 | (2006.01) |
| H04N 5/33 | (2006.01) |
| G06T 11/60 | (2006.01) |
| G06T 19/00 | (2011.01) |
| H04N 13/02 | (2006.01) |
| G06T 7/00 | (2017.01) |
| A61B 5/16 | (2006.01) |
| A61B 5/0205 | (2006.01) |
| G01N 30/72 | (2006.01) |
| C12Q 1/6886 | (2018.01) |
| C12Q 1/6883 | (2018.01) |
| G01N 33/68 | (2006.01) |
| G06F 19/00 | (2018.01) |
| G06F 17/30 | (2006.01) |

(52) U.S. Cl.
CPC .......... *A61B 5/0075* (2013.01); *A61B 5/0077* (2013.01); *A61B 5/02055* (2013.01); *A61B 5/165* (2013.01); *A61B 5/4815* (2013.01); *A61B 5/742* (2013.01); *C12Q 1/6883* (2013.01); *C12Q 1/6886* (2013.01); *G01N 30/724* (2013.01); *G01N 33/6848* (2013.01); *G06F 17/3087* (2013.01); *G06F 17/30973* (2013.01); *G06F 17/30979* (2013.01); *G06F 19/3418* (2013.01); *G06F 19/3431* (2013.01); *G06K 9/00369* (2013.01); *G06T 7/0012* (2013.01); *G06T 11/60* (2013.01); *G06T 19/006* (2013.01); *G06T 19/20* (2013.01); *H04N 5/33* (2013.01); *H04N 13/025* (2013.01); *G01N 2570/00* (2013.01); *G06T 2207/10028* (2013.01); *G06T 2207/30201* (2013.01)

(58) Field of Classification Search
None
See application file for complete search history.

(56) References Cited

U.S. PATENT DOCUMENTS

| | | |
|---|---|---|
| 3,752,147 A | 8/1973 | Castro et al. |
| 4,880,013 A | 11/1989 | Chio |
| 6,333,985 B1 | 12/2001 | Ueda |
| 6,511,435 B1 | 1/2003 | Bluth et al. |
| 6,540,687 B2 | 4/2003 | Chio |
| 7,717,858 B2 | 5/2010 | Massad |
| 8,069,055 B2 | 11/2011 | Keen |
| 8,082,597 B2 | 12/2011 | Young |
| 8,249,941 B2 | 8/2012 | Saul |
| 8,534,549 B2 | 9/2013 | Sarkis, Jr. et al. |
| 8,560,371 B2 | 10/2013 | Levitt |
| 8,620,594 B2 | 12/2013 | Silver |
| 8,639,226 B2 | 1/2014 | Hutchings et al. |
| 9,011,834 B1 | 4/2015 | McKenzie |
| 2006/0085230 A1 | 5/2006 | Brill |
| 2008/0100916 A1 | 5/2008 | Suhl |
| 2010/0113892 A1 | 5/2010 | Kaput |
| 2011/0071410 A1 | 3/2011 | Chul |
| 2012/0030061 A1 | 2/2012 | Lu et al. |
| 2012/0078837 A1* | 3/2012 | Bagchi ............... A61B 5/00 706/52 |
| 2012/0246102 A1 | 9/2012 | Sudharsan |
| 2013/0110551 A1 | 5/2013 | Bingol |
| 2013/0129210 A1 | 5/2013 | Na |
| 2013/0131655 A1 | 5/2013 | Rigotti et al. |
| 2013/0144916 A1 | 6/2013 | Lum |
| 2013/0245391 A1 | 9/2013 | Hyde et al. |
| 2014/0063056 A1* | 3/2014 | Zhong ............ G06Q 30/0641 345/633 |
| 2014/0089399 A1 | 3/2014 | Chun |
| 2014/0188994 A1 | 7/2014 | Patterson |
| 2014/0330579 A1 | 11/2014 | Cashman et al. |
| 2015/0066824 A1 | 3/2015 | Harris |
| 2015/0186419 A1 | 7/2015 | Agrawal |
| 2015/0252428 A1 | 9/2015 | Camper |
| 2015/0302505 A1 | 10/2015 | Di |

(Continued)

FOREIGN PATENT DOCUMENTS

| | | |
|---|---|---|
| EP | 0312821 A1 | 4/1989 |
| WO | WO2015063376 | 5/2015 |

OTHER PUBLICATIONS

Qiu, Q., Chang, Z., Draelos, M., Chen, J., Bronstein, A., & Sapiro, G. (Dec. 2015). Low-cost Gaze and Pulse Analysis using RealSense. InProceedings of the 5th EAI International Conference on Wireless Mobile Communication and Healthcare (pp. 276-279). ICST (Institute for Computer Sciences, Social-Informatics and Telecommunications Engineering).*
KCA Chan, C Ding, A Gerovassili, SW Yeung, RWK Chiu, TN Leung, TK Lau, SSC Chim, GTY Chung, KH Nicolaides, YMD Lo. Hypermethylated RAAFIA in Maternal Plasma: A Universal Fetal DNA Marker that Improves Reliability of Noninvasive Prenatal Diagnosis. Clinical Chemistry, 2006, vol. 52, No. 12, p. 2211-2218.*
Sayem, Resizable Outerwear Templates for Virtual ESIGN and Pattern Flattening 2012.
Gu, Study of 2D Automatic Anthropometric and Pattern Generation System, International Journal of Advancements in Computing Technology(IJACT) vol. 5,No. 6,Mar. 2013.

(Continued)

*Primary Examiner* — John S. Brusca
*Assistant Examiner* — Olivia M Wise
(74) *Attorney, Agent, or Firm* — Tran & Associates

(57) ABSTRACT

A mirror system includes a visual display disposed to convey information and images during an active period; and the visual display disposed to provide a reflected image during an inactive period; a multi-spectral 3D camera including a high definition video camera and an infrared camera; and a processor coupled to the visual display and the multi-spectral 3D camera.

18 Claims, 6 Drawing Sheets

(56) References Cited

U.S. PATENT DOCUMENTS

| | | |
|---|---|---|
| 2015/0344944 A1 | 12/2015 | Reid |
| 2015/0370963 A9 | 12/2015 | Dewey |
| 2016/0019335 A1 | 1/2016 | Dehaven |
| 2016/0026926 A1 | 1/2016 | Yeung |

OTHER PUBLICATIONS

Lim, Automatic Pattern Generation Process for Made-to-Measure, JTATM vol. 7, Issue 4, Fall 2012.

Xu, Pattern Automatic Generation for Men's Trousers, IJCA vol. 7 No. 5 (2014), pp. 123-132.

Sayem, Resizable Outerwear Templates for Virtual Design and Pattern Flattening, 2012.

Gu, Study of 2D Automatic Anthropometric and Pattern Generation System, International Journal of Advancements in Computing Technology(IJACT) vol. 5,No. 6,Mar. 2013 doi:10.4156/ijact.vo15.issue6.34.

Lim, AUtomatic Pattern Generation for Made to Measure, JTATM, vol. 7 Fall 2012.

Xu, Pattern Automatic Generation for Men's Trousers, ISSN: 2005-4297 IJCA 2014 SERRSC.

Chen et al, Personal Omics Profiling Reveals Dynamic Molecular and Medical Phenotypes, Cell 148, 1293-1307, Mar. 16, 2012.

Lanman et al, Analytical and Clinical Validation of a Digital Sequencing Panel for Quantitative, Highly Accurate Evaluation of Cell-Free Circulating Tumor DNA, PLOS ONE | DOI:10.1371/journal.pone.0140712 Oct. 16, 2015.

Edwards,Protein Identification from Tandem Mass Spectra by Database Searching, 2014.

Kaput, Nutritional genomics: the next frontier in the postgenomic era, Physiol Genomics 16: 166-177, 2004; 10.1152/physiolgenomics.00107.2003.

Park, Computer Aided Technical Design, JTATM vol. 7, Issue 1, Spring 2011.

Vaseghi, Advanced Digital Signal Processing and Noise Reduction 2008.

Willimon, Classification of Clothing Using Midlevel Layers, ISRN Robotics vol. 2013 (2013), Article ID 630579, http://dx.doi.org/10.5402/2013/630579.

* cited by examiner

| |
|---|
| Capture 3D model of body (310) |
| Digitally remove current dress (312) |
| Select new fashion styles from new trends (314) |
| Morph or project clothing onto the 3D model of body with mirror (316) |
| Allow user to gesture and iteratively change fashion color, length until satisfied with new clothing with the mirror (318) |
| Allow user to select from a library of jewelry and shoes to provide realistic simulation with the mirror (320) |
| Order desired clothing with custom measurements from the mirror (322) |

FIG. 3A

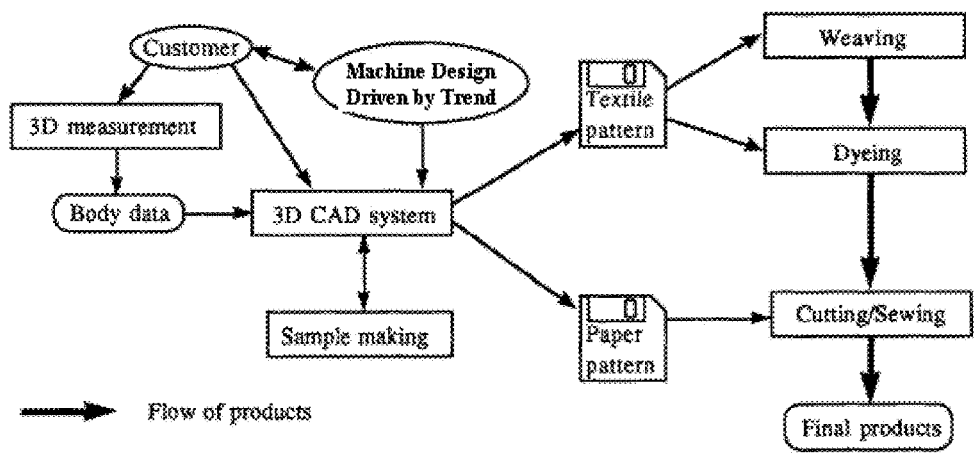

FIG. 3C

| Capture 3D model of head with the mirror (350) |
| --- |
| Remove current hair (352) |
| Select hair styles from new trends (354) |
| Morph or project hair onto the 3D model of head (356) |
| Allow user to iterative change hair styling with gestures directed at mirror until satisfied with new hairdo (358) |
| Allow user to select from a library of wardrobes with gestures directed at mirror to provide realistic simulation with the mirror (360) |
| Share desired hair style with professional to achieve desired hairdo (362) |

FIG. 4

| Capture 3D model of user body with the mirror (370) |
| --- |
| Isolate breast or butt region (372) |
| Model shape and size of breast or butt increase due to implant with the mirror (374) |
| Morph or project the shape/size of breast or butt increase onto the 3D model of user with the mirror (376) |
| Allow user to iterative change breast/butt shapes/sizes with gestures directed at mirror until satisfied with new shape (378) |
| Allow user to select from a library of wardrobes to provide realistic simulation with the mirror (380) |
| Send desired shape and provide feedback to plastic surgeon to implement desired shape and size (382) |

FIG. 5

SMART MIRROR

BACKGROUND

The present invention relates to image analysis and pattern recognition with a mirror.

A study from AOL and the Today show found that women spend an average of 55 minutes in front of the mirror every day, whereas men spend 39 minutes every day. The mirror is thus an integral part of life that has not yet joined the digital age.

SUMMARY

In one aspect, a smart mirror provides relevant information to a user to prepare him/her for daily tasks. The smart mirror overlays a graphical user interface over a partially reflective glass. The user interface can provide news, traffic and weather information, emails, social network communications. The smart mirror can act on the user's verbal requests or gestures. A mirror gesture control system includes a plurality of cameras mounted proximal to the mirror to detect edges of an object; and a processor to translate the edges as mouse movement and mouse clicks to control the vehicle by moving hands.

In another aspect, a camera tracks movements and a 3-D scanner analyzes the viewer's physique. Body recognition software analyzes the body shape to determine weight loss or gain. The smart mirror can provide clothing/jewelry/hair styling suggestions along with augmented reality view of the suggestions so that the user can visualize the impact of the clothing or jewelry or styling. Facial recognition software inspects the face shape to determine health. The smart mirror can provide make-up suggestions along with augmented reality view of the applied suggestions so that the user can visualize the impact of the makeup. The smart mirror can provide non-surgical body augmentation suggestions such as breast/buttock augmentations along with augmented reality view of the body enlargements or size reduction so that the user can visualize the impact of the body enhancement, along with clothing or jewelry or hair styling changes.

In yet another aspect, built-in sensors in combination with mobile phone usage pattern and social network communications can detect signs of stress and other mental/emotional health states of the user. The mirrors could also be combined with other health-related apps to keep track of your calorie count, vital signs, fitness level and sleep quality. By extrapolating from the user's current behaviors, vitals and bone and muscle structure, the augmented-reality mirror can forecast the user's future health. The camera can measure breathing activity and/or heart rate of the user in front of the mirror or alternatively the system can bounce WiFi off the chest to detect breathing activity. The mirror highlights hard-to-see changes in the body, such as increased fatigue, minute metabolic imbalances and more. A DNA analyzer can receive swipes from tongue, ear, and saliva, bodily fluids to capture genetic data at a high frequency and such data can be correlated with the fitness wearable devices for signs of health problems. Additionally, the data can be analyzed at a metropolitan level for public health purposes.

Advantages may include one or more of the following. The mirror provides convenience and time efficiency when a user is in front of a mirror. As today's habits shape future health, the smart mirror can encourage users to take healthy actions. The time spent in front of the mirror can be used to continually monitor health and proactively report any changes before they get serious. The smart mirror converts an everyday object that's already in the homes into a communication portal, and provides people with more "granular" health data that may otherwise be undetected until their yearly checkups. The system turns time spent in the bathroom into fun or productive periods. When these effects are considered in aggregate, one or more of the methodologies described herein may obviate a need for certain efforts or resources that otherwise would be involved in convenience to the user. Efforts expended by user or provider of fashion products may be reduced by one or more of the methodologies described herein. Computing resources used by one or more machines, databases, or devices may similarly be reduced. Examples of such computing resources include processor cycles, network traffic, memory usage, data storage capacity, power consumption, and cooling capacity.

BRIEF DESCRIPTION OF THE DRAWINGS

FIG. 3A shows an exemplary process for suggesting styles for the user with the mirror.

FIG. 3C shows a mass-customized clothing fabrication network that is driven by current fashion and hot celebrity trends.

FIG. 4 shows an exemplary hair style suggestion process with the mirror.

FIG. 5 shows an exemplary medical cosmetic suggestion process with the mirror.

DESCRIPTION

Figure 1:
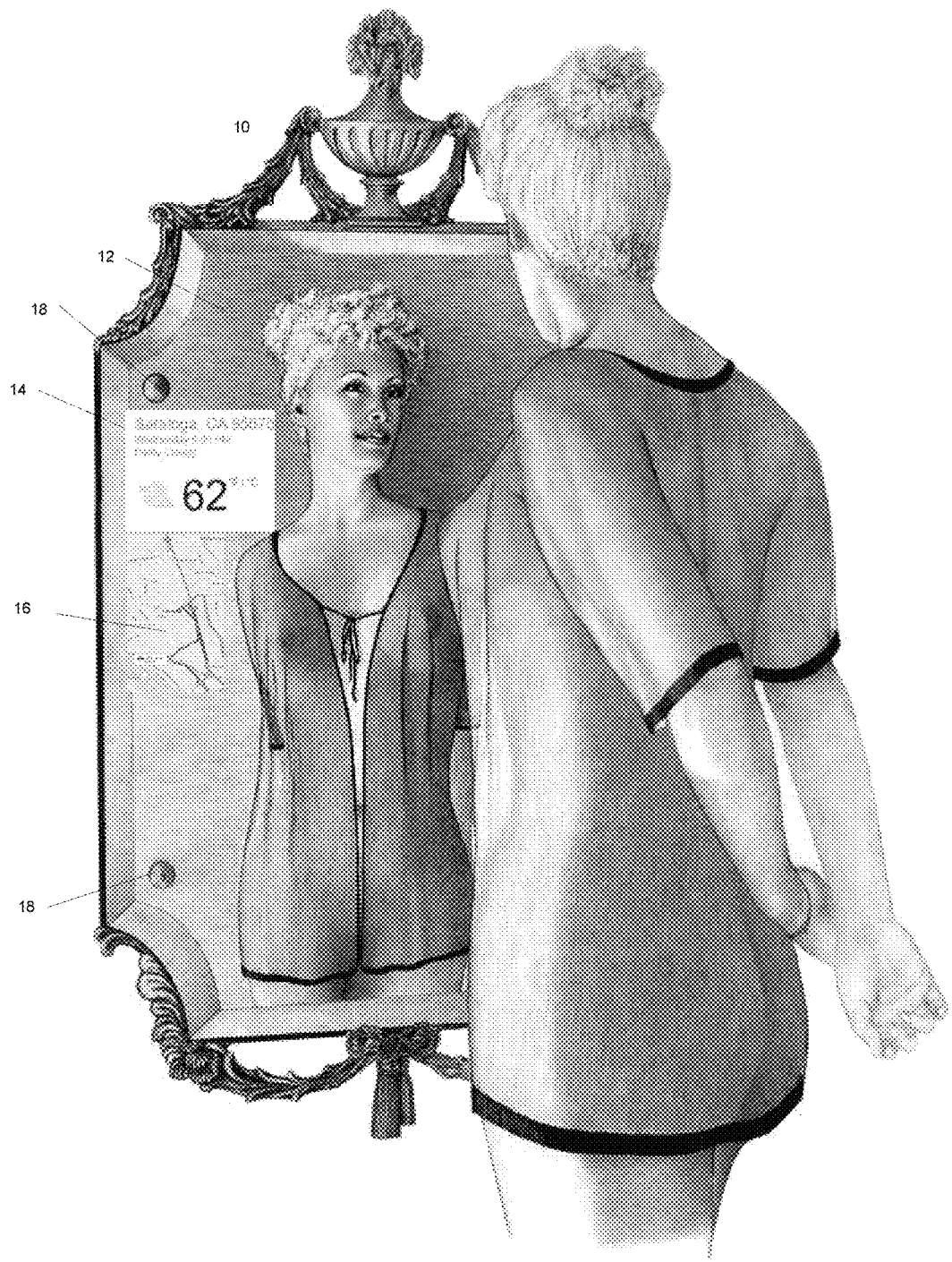
FIG. 1 shows an exemplary smart mirror.

FIG. 1 shows an exemplary smart mirror 10 that provides relevant information such as weather 14 and traffic 16 to a user to prepare him/her for daily tasks. The smart mirror 10 overlays a graphics user interface 13-16 over a reflective glass 12. The user interface can provide videoconferencing, news, traffic and weather information, emails, social network communications, among others. The smart mirror can act on the user's verbal requests or gestures.

Figure 2A:
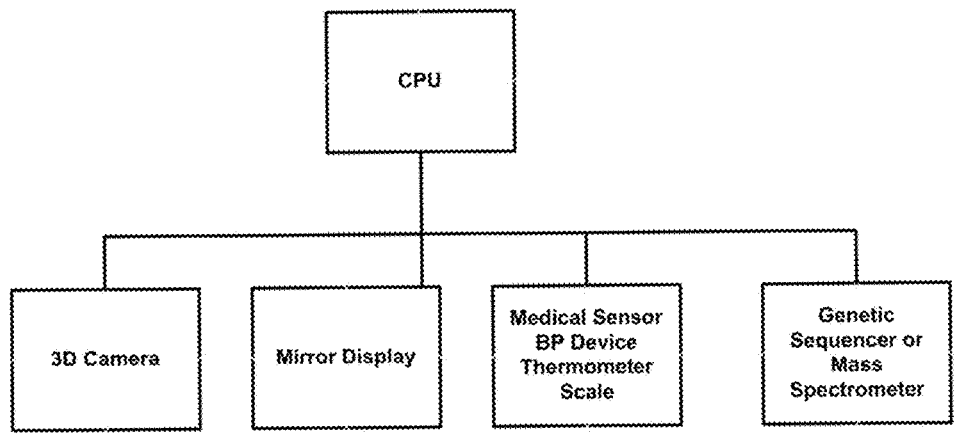
FIGS. 2A-2B show exemplary hardware supporting the smart mirror.
Figure 2B:
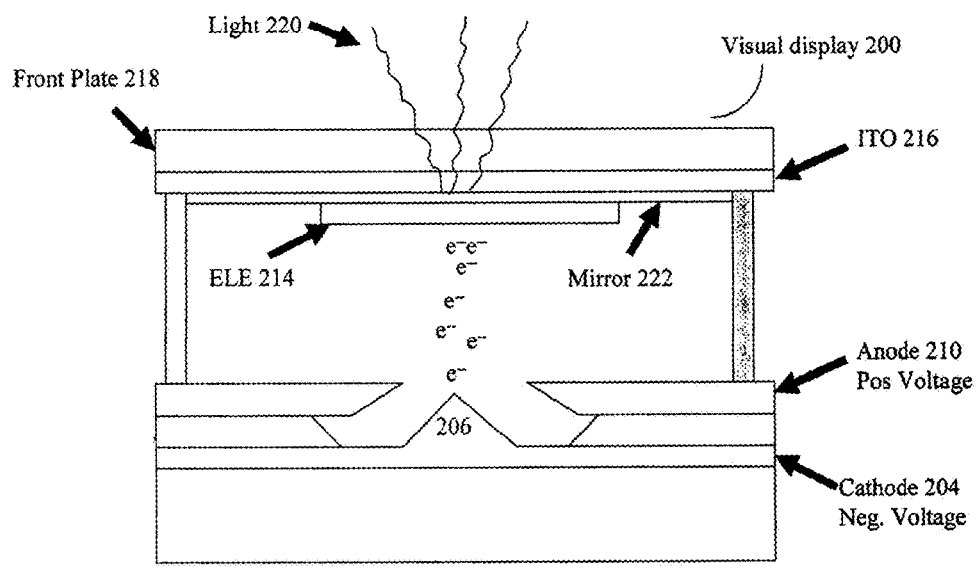

FIGS. 2A-2B show exemplary hardware supporting the smart mirror. As shown in FIG. 2A, a processor communicates with a mirror display and receives 3D information from a 3D camera. The processor can also communicate with fitness sensors that detect physical activity, sleep quality, heart rate, among others. The process can also capture medical information such as blood pressure, temperature, weight scale, among others. In certain embodiments, a portable genetic analyzer or mass spectrometer can communicate DNA information captured from hair, skin flakes, saliva, stool, urine, and sweat, among others, to the processor. In one embodiment shown in FIG. 2B, a display disposed to convey information and images during an active period; and the visual display disposed to provide a reflected image during an inactive period. The display device includes a transparent front plate having an internal and an external surface, and a metal layer formed on the internal surface of the front plate, the metal layer having a thickness selected to reflect a majority of incident external light during a time period when the visual device is in an off state, while transmitting a majority of internally generated light during a time period when the visual device is in an on state. In another embodiment, a solar panel can be positioned above the metal layer to capture light and generate electricity therefrom. In one embodiment shown in FIG. 2, a high resolution display can be converted into an efficient mirror during time periods when the visual display is not needed for active data and image transmission. The elements of the illustrative embodiment of an electroluminescent device 200 pixel differ from a conventional display in the addition of a mirror layer 222 placed between electroluminescent element (ELE) 214 and the Indium tin oxide (ITO) 216. The mirror layer 222 may be what is known as a one way mirror, or a half coated mirror, and comprise a very thin layer of a reflective material. For example, the reflecting layer may be formed of aluminum, with a thickness that is less than what may be known as the skin depth of the material. Such a thin layer may be adjusted to allow a desired percentage of the incident light to pass through. When the cathode 204 is emitting electrons to strike the ELE 214, there will be a substantial number of photons of light 220 produced, and with a thin enough half mirror layer 222, the great majority of the photons will pass through the ITO 216 layer and the front plate layer 218 to form part of the image. On the other hand, during time periods when the cathode 204 is not emitting electrons, the region between the anode 210 and the front plate 218 will be dark and there will be few photons of light 220 produced. In this situation, the majority of the light from the external area beyond the top surface of the front plate will either reflect back from the top surface of the front plate 218 (as occurs with the situation of a lighted room reflected in the window looking out over a dark night) or from the ITO layer, but the great majority of the light will reflect from the half mirror layer 222, as occurs with what are known as one way mirrors. Thus, the visual display 200 becomes an improved mirror when there is no image projected. The mirror layer 222 should have a thickness determined by the specific allowable loss of display intensity due to photons of light 220 lost in the mirror layer 222, as compared to the desired improvement in the front plate 218 mirror properties. The mirror layer may be formed from a conductive material, and so may be used as the electron attracting positive electrode, or as an addition to the existing ITO 216 electrode. Thus, the high resolution display can be converted into an efficient mirror during time periods when the visual display is not needed for active data and image transmission. When the display is active, to simulate a mirror, the display can capture the user's 3D model and superimpose the room's background with the user's movement and thus an electronic mirror is presented. The mirror has voice recognition with search capabilities such as those done by Apple's Siri™, Microsoft's Cortana™, or Amazon Alexa™ speech response units.

A mirror gesture control system includes a plurality of cameras 18 (FIG. 1) mounted proximal to the mirror to detect edges of an object, among others. In one embodiment the Microsoft Kinect® camera can be used, while in another embodiment, a 3D camera such as the Intel RealSense® uses three components: a conventional camera, a near infrared image sensor and an infrared laser projector. Infrared parts are used to calculate the distance between objects, but also to separate objects on different planes. In one embodiment, a processor to translate the edges as mouse movement and mouse clicks to control the vehicle by moving hands. They serve for facial recognition as well as gestures tracking. The Intel 3D camera can scan the environment from 0.2 m to 1.2 m. Its lens has a built in IR cut filter. The video camera has a frame rate up to 60 fps with a 90° FOV, moreover its lens has an IR Band Pass filter. The IR laser integrates an infrared laser diode, low power class 1, and a resonant micro-mirror. The 3D camera can provide skeletal and depth tracking and may gather spatial data that describes objects located in the physical environment external to the depth sensor (e.g., the user's bath room). The skeletal and depth tracking technology may be implemented in a depth sensor (e.g., the Kinect®, the Intel Realsense®, stereo cameras, mobile devices, and any other device that may capture depth data. In some example embodiments, the skeletal and depth tracking technology is implemented on a server using algorithms that utilize the RGB and depth channels. In some example embodiments, depth sensing technologies use structured light or time off light based sensing. For example, an infrared (hereinafter, also "IR") emitter that is part of the preference analysis machine 310 and that is located in the user's living room, may project (e.g., emit or spray out) beams of infrared light into surrounding space. The projected beams of IR light may hit and reflect off objects that are located in their path (e.g., the user or a physical object in the user's living room). A depth sensor (e.g., located in the user's living room) may capture (e.g., receive) spatial data about the surroundings of the depth sensor based on the reflected beams of IR light. In some example embodiments, the captured spatial data may be used to create (e.g., represent, model, or define) a 3D field of view that may be displayed on a screen (e.g., of a TV set, computer, or mobile device). Examples of such spatial data include the location and shape of the objects within the room where the spatial sensor is located. In some example embodiments, based on measuring how long it takes the beams of IR light to reflect off objects they encounter in their path and be captured by the depth sensor, the preference analysis machine 310 may determine the location (e.g., the distance from the depth sensor) of the objects off which the beams of IR light reflected (e.g., the user, a furniture piece, or a wall). In various example embodiments, based on the received spatial data, the system may determine details of the objects in the room, such as spatial measurements of the objects in the room (e.g., the dimensions of the user's body). The camera determines one or more measurements (e.g., dimensions) of the body of the user as part of the analysis of the image and the model. The processor with 3D model information from the user may also determine, based on the measurements of the user's body, one or more sizes of fashion items from different brands (e.g., manufacturers or sellers of fashion items) that may fit the user's body.

Video Conferencing with Virtual Background

For video conferencing, the camera can extract just the head of the user from background scenery and replace the background with a user selected background. For example, the background might show a logo or a business scene. The user can simply incorporate a virtual, not physical, background when video conferencing with customers, suppliers, co-brokers, logistics providers, bankers, etc., from the privacy of a bathroom or home.

Calendaring

The mirror can show the user's calendar and suggested activities for free time and busy time, or activities to be performed based on upcoming events. For example, if user's schedule includes a date (e.g., user entered, company entered, etc.) in the future for the completion of a report, suggestions can be made earlier in time (e.g., during open time slots, blocked time slots) to the user to begin preparing the report, or begin researching data for preparing the report, for example. If the report completion is an important deadline, as tagged by the user or the entity that inserted the scheduled task, the suggestions for preparation and completion can be given higher priority over other suitable suggestions returned by the architecture. The suggested activities can be obtained from web-based sources (e.g., social networks), enterprise sources, client machines, other accessible information sources, or any combination thereof. For example, in one implementation, the user can select or prioritize the sources of suggested activities such that a suggestion from a first source will be given higher priority over a suggestion related to a second source. This can be changed on a time basis, as well. For example, if the first source is of the user's employer and the second source is an entertainment source, suggestions from the employer source can be given higher priority with one month of project completion, while entertainment suggestions will be given higher priority immediately after the project completion date, or one week before project completion (to begin preparing for vacation or a short relaxing break). In another example, the user places a parent birthday on the calendar. The system then suggests time for the user to shop for a gift for the parent two weeks before the birthday. In yet another example, the user indicates on a to-do list a dinner engagement with another couple two weeks hence, but the location is yet to be determined. Five days before the approximate time the system suggests that the user block out time to choose a restaurant, generates a candidate list of suggestions, and provides links to the candidates for booking. If the calendar indicates an event such as a concert, the system can also suggest fashion styles to stand out.

Clothing Recommendation

One embodiment includes obtaining a 3D model of a user standing in front of the display and rendering one or more articles or products on the 3D model. Images such as photographs or videos can be made of the user (also referred to as customer or client) when trying on different articles. These images can be seen on the display and can simply be ordered/edited/deleted by the user by "dragging" them across the screen. In this example, the display is designed as a touch screen. In this manner, the articles tried on can be compared more realistically and more easily by the user.

A user can be a consumer of fashion items. Further, a user may include an expert such as a fashion professional, where this fashion professional includes a fashion designer, a personal shopper, a personal stylist, a journalist who reports on fashion, or some other suitable person. Matching is based, in part, upon an attribute of a fashion item. Attributes include color, fabric, cut, designer, size, time of creation, and other suitable attributes used in denoting a fashion. In one example embodiment, matching includes receiving input in the form of a particular fashion item, and based upon this fashion item suggesting an additional fashion item based upon matching attributes. Matching is facilitated through the use of a learning machine. In one example embodiment, the learning machine can determine the user's favorite actress or model and build a related association. Thus, the fashion style from trendy stars, models, and musicians followed by the user in social media (Facebook, twitter) can be analyzed and similar items can be added to the virtual digital closet of the user. Similar clothing items worn by the actress or model can be retrieved and the clothing data can be superimposed on the 3D model of the user to show the user the expected appearance. In addition, experts such as magazine editors/writers can provide outfit ideas and the user can apply the outfit ideas to his/her wardrobe and hairstyling, among others. The user can adjust color or size or any other attributes of the clothing, and place an order. The order is sent to the fashion maker, who customizes the item accordingly and ships the product to the user.

One exemplary process is as follows:

Identify user's current fashion style. The fashion item can be hair styles, clothing, shoes, bras, dental wear (braces/aligners)

Figure 3B:
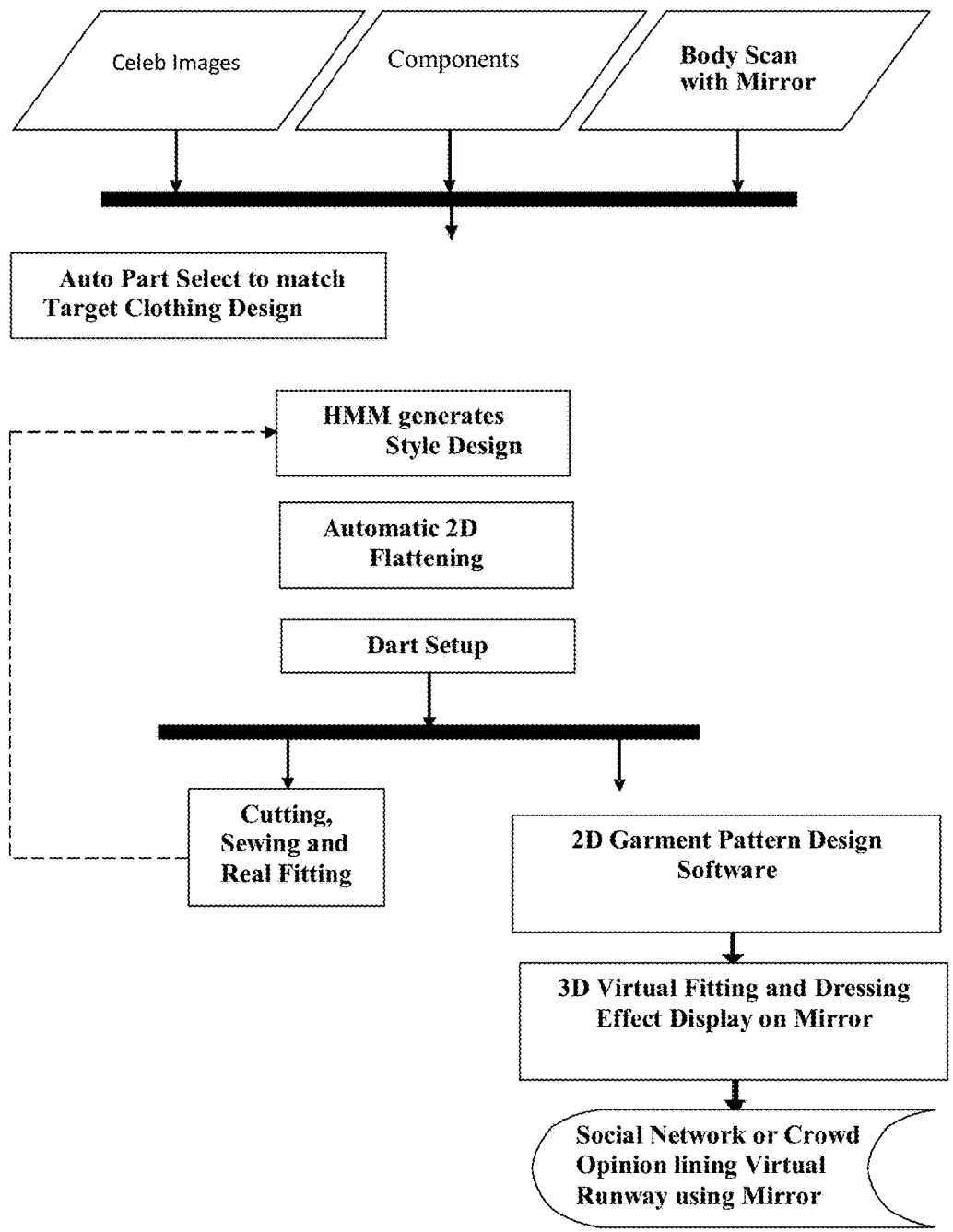
FIG. 3B shows an exemplary process for producing custom fashion clothing based on images or videos of a model or a celebrity that the user likes.

Determine matching style sets based on one or matching attributes, current fashion style, fashion experts, or celebrity styles Present matching style sets and get user selection Identify vendor of the user selected style Render a 3D augmented reality imposed over the user 3D model for preview Accept user customization requests and re-render the 3D augmented reality view Send data to the vendor to ship fashion product to the user FIG. 3 shows an exemplary process to provide mass-customized clothing Capture 3D model of body (310)

Digitally remove current dress (312)

Select new fashion styles from new trends (314)

Morph or project clothing onto the 3D model of body (316)

Allow user to iterative change fashion color, length until satisfied with new clothing (318)

Allow user to select from a library of jewelry and shoes to provide realistic simulation (320)

Order desired clothing with custom measurements (322)

In one embodiment, trendy clothing identified based on news or Internet buzz can be located. In this embodiment, the system performs a search of an inventory of fashion items based on the identified fashion preference of the user and then performs a similarity search of the fashion inventory and generates similarity search results (e.g., fashion items that are similar to an item previously worn by the user).

In some example embodiments, the similarity search is based on an image search of the style or the identification of similar clothing. In some instances, the similarity search is also based on one or more measurements of the user's body. For example, to perform a similarity search, the search module compares one or more visual features extracted from the fashion image and one or more visual features identified in an image depicting a fashion item included in the fashion inventory being searched. In some example embodiments, the similarity search is based on an attribute-value pair that characterizes a fashion item previously worn by a celebrity, model, star, user's friend, user's social network or even by the user. In some instances, the similarity search is also based on one or more measurements of the user's body. The performing of the similarity search may include selecting an attribute-value pair to be used as a query attribute-value pair and identifying one or more items in the fashion inventory that are characterized by the attribute-value pair. In some instances, the coordination search is also based on one or more measurements of the user's body. The performing of the coordination search may include identifying, based on a coordination rule, one or more items in the fashion inventory that can be worn together with the fashion item that corresponds to the query image. Similarly, the search module may perform a similarity search based on the first image and then may generate one or more similarity search results. The search module may perform a coordination search based on the second image and further generate one or more coordination search results.

As still yet another embodiment, a feature to perform similarity searching is a user's geographical location used as a criterion to match the user to other users as style may vary from one location to another location. To illustrate this type of feature by way of example only is the case where a user A is a business executive woman living in Country A1. She is travelling on a business trip to country B1. Country A1 could be a conservative country, where ethnic attire is normally worn even in business meetings. Country B1 could be a fashion conscious country. User A may want to wear fashionable clothing, that would look smart on her and be appropriate for business meetings in B1." In yet another example of using this type of feature of engine 110 is illustrated as follows, a user is a graduating 22 year old female, 5'3", 145 lbs, having a hourglass body shape, starting a new job as a project manager in New York. She does not know what kind of attire is appropriate and what style of clothing would look good on her. She creates an account on the system of the present invention, creates her profile, enter her attributes, instantly gets matched to other users of similar attributes and gets recommendation on what style of attire would look good on her. In another preferred embodiment, the system may her to purchase the item in her size.

Clothing Fabrication

Based on the above fashion recommendation, the system can fabricate mass-customized clothing for the user that is trendy. The process has a training phase and a run-time phase as follows:

Training
Collect library of fashion designs (Pinterest, Google image, facebook images)
Normalize the fashion designs to standard size
Break up the designs into sections and extract features of sections
Clusterize the features into a codebook of clothing design sections/elements
Train library and create probabilistic model (HMM) to represent a fashion design as a collection of sections
Run-Time
Generate 3D model of user
Receive images of target fashion worn by celebrity or model for the user
Normalize target fashion images to a standard size
Extract features from the target fashion images
Apply probabilistic model to features and create a 3D model of the target fashion model
Do virtual fit to the user 3D model and optimize the 3D clothing model for crotch fitting and movement stress
Flatten the 3D clothing model into 2D pattern
Present to laser cutter to cut pattern
Move cut pattern to computerized sewing system
Perform QA as needed and ship mass-customized clothing to user In one embodiment, the system receives images of trendy clothing or clothing style from a celebrity that the user wishes to match. The images can be extracted from various news outlet or celebrity sites, for example from google images with search "celebrity fashion" or "tom cruise fashion", for example. For both training and run-time, the system generates features associated with portions of the fashion clothing. In one embodiment, a L-C-S-H process can be used, for low-level-characteristics-selection mask-high level. Low-level refers to the features that are calculated from the images of each article (e.g., 2D shape, 2D color, 2D texture, 2D edges, and 3D shape). Characteristics refer to the attributes that are found on generic articles of clothing (e.g., pockets, collars, hems). Selection mask refers to a vector that describes what characteristics are most useful for each category (e.g., collars and buttons are most useful for classifying shirts), used as a filter. High level refers to the categories to be classify (e.g., shirts, socks, dresses). In one embodiment, the unique characteristics to differentiate categories of clothing can be: Collar, Top brackets, Dark colored, Denim, Ankle hem, Front pockets, Graphic pictures, Colored, Plaid, Thigh hem, Back pockets, Graphic texts, White colored, Patterns, Inseam, Side pockets, Belt loops, V-neck, Round neck, Elastic band, Top buttons, Striped, Bicep hem, Front zipper, Shoulder hem, Wrist hem, or Shin hem, among others.

The L component of the approach uses the low-level features to estimate if the article does or does not have a particular characteristic. The low-level features that were used in this approach consist of color histogram (CH), histogram of line lengths (HLL), table point feature histogram (TPFH), boundary, scale-invariant feature transform (SIFT), and fast point feature histogram (FPFH). To combine the low-level features of all five instances into a single value or histogram, each value is determined by averaging each individual value along with its neighbors, in the case of the histogram.

For the part of the algorithm that converts from low-level to characteristics, low-level features are compared to the various characteristics. Since the characteristics were binary values, libSVM is used to solve the two-class problem. Each low-level feature determines if the characteristic is in class 1 or 2. Class 1 contains positive instances and class 2 contains negative instances.

For an article of clothing, a high definition RGB image and a raw depth map and background subtraction is done on the RGB image to yield an image of only the object. The background subtraction is performed using graph-based segmentation. Once the object is isolated within the image, multiple features are calculated from the RGB image and the 3D point cloud. These featurescapture 2D shape, 2D color, 2D texture, 2D edges, and 3D shape for both global and local regions of the object. One implementation uses Felzenswalb and Huttenlocher's graph-based segmentation algorithm which uses a variation of Kruskal's minimum spanning tree algorithm to iteratively cluster pixels in decreasing order of their similarity in appearance. An adaptive estimate of the internal similarity of the clusters is used to determine whether to continue clustering.

A color histogram CH is a representation of the distribution of the colors in a region of an image, derived by counting the number of pixels with a given set of color values. CH are chosen in this work because they are invariant to translation and rotation about the viewing axis, and for most objects they remain stable despite changes in viewing direction, scale, and 3D rotation. CH is used to distinguish, for example, between lights and darks, as well as denim.

A Table Point Feature Histogram (TPFH) feature consists of a 263-dimension array of float values that result from three 45-value subdivisions, that are calculated from extended fast point feature histograms (eFPFH), and 128-value subdivision for table angle information. This feature is a variant on the viewpoint feature histogram. The eFPFH values are calculated by taking the difference of the estimated normals of each point and the estimated normal of the objects centerpoint. The estimated normals of each point and the centerpoint are calculated by projecting them on the XY, YZ and XZ plane.

A boundary feature captures 2D shape information by storing the Euclidean distances from the centroid of each article to the boundary. First, the centroid of each binary image is calculated containing the object (after background subtraction). Then, starting at the angle of the major axis found by principle components analysis, 16 angles that range from 0 to 360 (i.e., 0 to 337.5) are calculated around the object. For each angle, the process measures the distance from the centroid to the furthest boundary pixel Other feature includes histogram of line lengths (HLL) to help distinguish between stripes, patterns, plaid, and so forth. For this, we use the object image as before (after background subtraction) and compute the Canny edges, then erode with a structuring element of ones to remove effects of the object boundary.

Next, local features can be computed. The SIFT, scale invariant feature transform, descriptor is used to gather useful 2D local texture information. The SIFT descriptor locates points on the article (after background subtraction) that provide local extremum when convolved with a Gaussian function. These points are then used to calculate a histogram of gradients (HoG) from the neighboring pixels. The descriptor consists of a 128-value feature vector that is scale and rotation invariant.

A FPFH, fast point feature histogram descriptor can be used to gather local 3D shape information. The FPFH descriptor utilizes the 3D point cloud and background subtraction for each article and segments the article from the background of the point cloud. For each 3D point, a simple point feature histogram (SPFH) is calculated by taking the difference of the normals between the current point and its neighboring points with a radius. Once all of the SPFHs are computed, the FPFH descriptor of each point is found by adding the SPFH of that point along with a weighted sum of the neighbors. Other features and descriptors can be used.

Once the features are computed, the global features are concatenated to create a histogram of values. For local features, SIFT and FPFH are calculated separately through bag-of-words to get two element histograms of codewords. Being concatenated, this yields predetermined values for the local features. Then being concatenated with global features yields additional values, which are then fed to the multiple one-versus-all SVMs.

With the codebook, one embodiment can train a probabilistic learning system such as Hidden Markov Model (HMM) to represent a fashion design as a constrained combination of various esthetic components or sections. HMM is a statistical Markov model in which the system being modeled is assumed to be a Markov process with unobserved (hidden) states. A HMM can be presented as the simplest dynamic Bayesian network. In simpler Markov models (like a Markov chain), the state is directly visible to the observer, and therefore the state transition probabilities are the only parameters. In a hidden Markov model, the state is not directly visible, but the output, dependent on the state, is visible. Each state has a probability distribution over the possible output tokens. Therefore the sequence of tokens generated by an HMM gives some information about the sequence of states. The adjective 'hidden' refers to the state sequence through which the model passes, not to the parameters of the model; the model is still referred to as a 'hidden' Markov model even if these parameters are known exactly. A hidden Markov model can be considered a generalization of a mixture model where the hidden variables (or latent variables), which control the mixture component to be selected for each observation, are related through a Markov process rather than independent of each other. Recently, hidden Markov models have been generalized to pairwise Markov models and triplet Markov models which allow consideration of more complex data structures and the modelling of nonstationary data. Other machine learning/classifiers can be used, as detailed below.

Once the system is set up, it can recognize and recreate clothing given an input image. For example, if a celebrity wears a fashionable clothing to attend a highly publicized event, images of the celebrity are publicized and the user may want to replicate the look. In this case, the system retrieves a 3D model of the user and receives images of target fashion worn by celebrity or model liked by the user. The system normalizes the target fashion images to a standard size and extracts features from the target fashion images as detailed above. The system applies the probabilistic model to features and creates a 3D model of the target fashion model using the HMM recognizer using the components/sections model. The system can then apply a virtual fit to the user 3D model and optimize the 3D clothing model for crotch fitting and movement stress.

In one embodiment, since the optimization problem is combinatorial and the number of combination items can vary (e.g., a pockets can be added or removed), it is difficult to define a closed-form solution. In fact, as in the real world, it is desirable to obtain multiple optimal solutions (outfits) from the various components instead of a single global optimum. The process generates candidate solutions by sampling a density function defined over the space of possible outfits. The density function is defined using idealized analytical formulations. Sampling is preferably performed using a Markov Chain Monte Carlo sampler. During the optimization dimensionality may change; i.e., the number of clothing components/sections may be altered during the optimization process, and a Reversible Jump MCMC (RJMCMC) framework supplements parameter-changing diffusion moves of Metropolis-Hastings (MH) with an additional set of dimension-altering jump moves, which allow the chain to move between subspaces of different dimension. To efficiently explore the solution space, a simulated annealing technique is applied in the optimization process with a Boltzmann-like objective function. A dimension matching strategy is adopted to allow reversible jumps across subspaces of different dimension or within the same subspace. The RJMCMC can be used to define the jump moves as adding/removing a clothing item to/from the outfit, which induce a dimension change, and diffusion moves as swapping items or modifying an item's colour, which involve no dimension change.

Various fitness criteria can be applied to evaluate how well the new design fits the user, such as comparing lengths and areas, analysis of space between clothing and the body, among others.

The final clothing model is flattened into 2D pattern. In one embodiment, each mesh element is deformed during the flattening from 3D to 2D plane. A pattern projection can be used that takes into consideration elastic and shear properties of the fabric.

One embodiment uses Design Concept Tex Tech (DCTT) software. The flattening operation involves two steps: first, the selection of the region part to be flattened, and second, the selection of flattening options appears in the "Flattening parameters" dialog box. The flattening tool provided by DCTT considers the geometric constraint of the shape, but no material properties. The process is comparable to the flattening of a network of springs whose stability is obtained through an even distribution of its internal energy. It is an iterative process which proceeds layer by layer beginning from the flattening start point. To control the flattening process, DCTT offers both automatic and numerical options, as can be seen in FIG. 3-6. The automatic control allows the flattening algorithm to run until balance is reached. This option is always selected for pattern flattening throughout this research work. To prepare the flattened pattern pieces for meaningful use in clothing manufacturing, an appropriate seam allowance is added around them. This is done in a "2D product" document using the "design parts" tool with the "create seamline part" option, which is available under the "parts" menu. Rendering of the virtual clothing items developed on the 3D templates is performed by keeping both the "3D Design" document (containing the 3D template and virtual clothing design) and the "2D pattern" document (containing the flattened pattern pieces open). On the active "2D Pattern" document, the "create rendering" tool with a "create virtual marker" option available under the "Pattern" menu is used to apply different graphical images of a particular pattern piece. After doing that, when the "realistic rendering" option in the "rendering" tab is activated, the graphic image applied on the pattern pieces is visualized in 3D.

In another embodiment, from the 3D model of the user, 2D non-contact anthropometric and automatic pattern generation system of men's shirts and pants can be done. The system needs the users to provide front and side photos of the target celebrity or model, and carry interaction design of shirts or pants' styles. Then the patterns can be automatically generated based on the user's physical measurement, the celeb photos and the style design. The two-dimensional anthropometric system is integrated with automatic pattern generation system. In one example, for men's trousers, an automatic pattern generation can apply predetermined rules on the 3D model of the user such as those by Hong Xu in Pattern Automatic Generation for Men's Trousers, ISSN: 2005-4297 IJCA 2014 SERSC.

The 2D pattern can be sent to a cutter such as a CNC or a laser cutter to cut patterns from a fabric that is selected by the user, and the system can move the fabric with the cut pattern on a conveyor to a computerized sewing system, where a robot can pick up the pattern and the sewing system can assemble the pieces into mass customized clothing. The machine fabrication can extend into computer controlled weaving, dying to create a highly mass-customized fashion wear for users, as shown in FIG. 3C.

In some embodiments, the user's purchase history, retained as part of their account information, may be used as training data for a Bayesian network component associated with the outfit suggestion component. For example, if the user has previously purchased high heel shoes and a jacket in the same purchase, the Bayesian network component may recognize that sports shoes and vests should both belong to the outfit.

The present 3D clothing design systems offer a number of benefits over 2D clothing design systems in use. Virtual prototyping using computer-based 3D clothing product-development techniques results in fewer physical prototypes and a shorter product-development phase. For decision-making on product selection and prior to the commencement of production, it is usual for at least two up to ten physical prototypes to be made when using existing traditional product-development systems and this incurs a high cost involvement and time consumption, Virtual prototyping and virtual try-on processes can significantly reduce the product-development time and cost. Virtual review and evaluation of fit with realistically simulated fabric behaviour can enable faster detection of errors and earlier corrections to design elements, material selection and assembly. At the same time, the virtual prototypes can be used as a marketing aid for online product presentation and internet-based retailing. The application of flattening technology provides the opportunity to combine clothing design and pattern creation in to a single step. Automatic flat pattern extraction from 3D designs offers a considerable reduction of the time and manpower involvement in the pattern cutting process. The instant 3D CAD system will form the nerve centre of at the centre of a textile information network.

Hairstyling Recommendation

In another embodiment, the system can analyze fashion trends based on the user's social network profile, the twitter follow profile, celebrity likes and followings, or expert advice from his/her fashion advisor or hairdresser or experts from magazines and a number of sources. As another alternative or addition, another feature that may be used by mirror to perform similarity searching may correspond to a user's height range to height range; weight-weight, body shape-body shape; age group appropriate as explained above; profession range-profession range; job position-job position; geographic location to geographic location and user profile attributes to celebrity profile attributes. For instance, the height and the width of a user's body figure, as well as a generalization or quantitative description of an overall head-shape (elongated or round shape) may provide another basis for identifying results. Additionally, a user may perform some actions on other user's images. For example: If the user likes the way clothing fits on another user, ii) likes the style of clothing, iii) likes clothing by brand, iv) type of clothing or for any other reason, the user can "like" the image, leave a "comment" on the image, or save the image in his/her digital closet.

The system first captures the user's head 3D model. For style recommendation, the hair color information, the apparel pattern information, the season information, the weather information, the indoor/outdoor information, and the time information may be included in the style characteristics. The recommendation unit may receive a style preference from the user or celebrity or experts as discussed above and search the recommendation style information matched with the received style preference, the face and the style characteristics. In addition, the style recognizer extracts style feature information from the images of the model/celebrity/favorite people that the user indicates directly or indirectly through social network likes and twitter-follow profiles, and recognizes style characteristics using the extracted style feature information. Next, the recommender may search recommendation style information matched with the face and style characteristics recognized in the face recognizer and the style recognizer in the recommendation style table in which the recommendation style information is templated according to face and style characteristics stored in the memory to provide the searched recommendation style information to the user.

The method includes selecting a suitable hair-style wherein the most suitable hair-style can be decided based on consideration of personality and facial features of each selector, along with adopting her preference and request, and at the same time to provide an image map for a hair-style where it can be easily defined what kind of an image the selected hair-style has. The system can analyze a contour of the selector's face and its image are defined for the hair-style brought by an inner line which constitutes a boundary line between a face and a hairline and an outer line which constitutes an outside of the hair style, and wherein it is analyzed whether the selected hair-style is suitable or not with respect to form and balance features and also analyzed whether the selected hair-style is suitable to the image.

Analysis for the form and the balance of the hair-style is performed based on five elements; 1. balance between upper and lower parts of the face, 2. Silhouette, 3. Face line, 4. Balancing between head and face, and 5. Total balancing.

Further, analysis for an image of the hair-style is performed based on two elements; 1. An impression on the hair-style and 2. An image gap between face features and a hair-style. Further, with regard to the analysis for a form of the hair-style and its balance, the analysis is performed based on a comparison of a standard proportion between the hair and the face. Further, the system can apply predetermined standards such as those in U.S. Pat. No. 6,333,985 where the standard proportion between the hair and the face is devised as follows:

1. The placement of the eyes is in the center of the whole construction.
2. The proportion ratio between distance from the eyes to the top end of a hair style and distance from the eyes to a bottom end of a jaw is 1:1.
3. The proportion ratio between length of a forehead, distance from the bottom of the forehead to a nose tip and distance from the nose tip to the bottom end of the jaw is 1:1:1.
4. The proportion ratio between the length of the forehead and distance from the top of the forehead at the hairline to the top end of the hair style is 1:0.5.
5. The proportion ratio between length and breadth of the face including the head and hair is, 1.5:1.

Further, an image for "light" and "heavy" is prepared on a perpendicular axis up and down, while the image for "curve line" and "straight line" is prepared on a horizontal axis, and thus representative hair-styles in accordance with these expressed images are arranged.

Further, the image for "light" has some features considered to be youthful such as fluffy loose hair ends, bright in color, having hairs on the forehead, to appear dry, and short to medium size.

On the other hand, the image for "heavy" has features associated with to be calm and an adult image such as stable in the hair-ends, dark in color, no hair on the forehead, to appear wet, and medium to long hair length.

The "curve line" depicts a warm and sweet image, with some features of the hair style waved and curled, a rounded line, and abundant soft hair at the sides.

The "straight line" depicts a cool and clean image, with some features of the style straight, an angular line, and having a long and hard silhouette.

For the face recognizing process and the style recognizing process, the recommendation device detects a face region from a user image transmitted and extracts face feature information from the detected face region. Next, the recommendation device may recognize gender and age from the extracted face feature information or from the user's social network profile. In addition, the recommendation device may extract style feature information from a region of the user image except for the face region and recognize the user style characteristics from the extracted style feature information. The hair style information matched with the face characteristics is used to superimpose the hair onto the user's 3D head model.

Then, the recommendation unit searches the recommendation style information for the characteristics matched with the face and style characteristics recognized in the face recognition unit and the style recognition unit in the recommendation style table according to the characteristics. Here, at least one of the hair style information, makeup style information, and recommendation product information is included in the recommendation style information. The recommendation unit may receive a style preference from the user and search the recommendation style information matched with the received style preference and the characteristics. Further, in the case in which a plurality of recommendation style information is searched, the recommendation unit may prioritize the plurality of searched recommendation style information according to a matched ratio with the characteristics.

FIG. 4 shows an exemplary process to provide trendy new hair recommendations
  Capture 3D model of head (350)
  Remove current hair (352)
  Select hair styles from new trends (354)
  Morph or project hair onto the 3D model of head (356)
  Allow user to iterative change hair styling until satisfied with new hairdo (358)
  Allow user to select from a library of wardrobes to provide realistic simulation (360)
  Share desired hair style with professional to achieve desired hairdo (362)
  Health The 3D camera tracks movements and a 3-D scanner analyzes the viewer's physique. Body recognition software analyzes the body shape to determine weight loss or gain. The smart mirror can provide clothing/jewelry/hair styling suggestions along with augmented reality view of the suggestions so that the user can visualize the impact of the clothing or jewelry or styling. Facial recognition software inspects the face shape to determine health. The smart mirror can provide make-up suggestions along with augmented reality view of the applied suggestions so that the user can visualize the impact of the makeup. The smart mirror can provide non-surgical body augmentation suggestions such as breast/buttock augmentations along with augmented reality view of the body enlargements or size reduction so that the user can visualize the impact of the body enhancement, along with clothing or jewelry or hair styling changes.

Built-in sensors in combination with mobile phone usage pattern and social network communications can detect signs of stress and other mental/emotional health states of the user. The mirrors could also be combined with other health-related apps to keep track of calorie count, vital signs, fitness level and sleep quality. By extrapolating from the user's current behaviors, vitals and bone and muscle structure, the augmented-reality mirror can forecast the user's future health. The camera can measure breathing activity and/or heart rate of the user in front of the mirror or alternatively the system can bounce WiFi off the chest to detect breathing activity. The mirror highlights hard-to-see changes in the body, such as increased fatigue, minute metabolic imbalances and more. A DNA analyzer can receive swipes from tongue, ear, and saliva, bodily fluids to capture genetic data at a high frequency and such data can be correlated with the fitness wearable devices for signs of health problems. Additionally, the data can be analyzed at a metropolitan level for public health purposes.

FIG. 5 shows an exemplary process to recommend cosmetic enhancements for women, and the process can be applied to men to improve muscular physique appearance
  Capture 3D model of user (370)
  Isolate breast or butt region (372)
  Model shape and size of breast or butt increase due to implant (374)
  Morph or project the shape/size of breast or butt increase onto the 3D model of user (376)

Allow user to iterative change breast/butt shapes/sizes until satisfied with new shape (378)

Allow user to select from a library of wardrobes to provide realistic simulation (380)

Send desired shape and provide feedback to plastic surgeon to implement desired shape and size (382)

The mirror becomes a personalized medical kiosk supporting method for using the mirror/personal medical kiosk advance healthcare delivery wherein users and physicians can engage in real-time interactive consultations, providing convenient and affordable healthcare services. The mirror/personal medical kiosk includes the latest technologies in medical devices, video conferencing, and VoIP telephony so that the mirror/personal medical kiosk can extend traditional healthcare to convenient retail pharmacy locations or other locations in a user's neighborhood, therein enabling a user to see a medical provider and obtain a prescription, if required, in a fast and convenient manner.

Some advantageous aspect of the mirror/personal medical kiosk and medical method are:

User Portal (Cloud Based).
Provider Portal (Cloud Based).
Integrated Care Station.
Facilitates Efficient Delivery of Basic Healthcare Delivery.
Automates All Aspects of a Check Up.
Easy Check-In.
Vital Signs Capture.
Prescription Generation.
Post Care and Outcomes.
Convenient Locations Where Consumers Want To Be.
Video playback of the recorded session between the user and medical provider.

The mirror/personal medical kiosk and medical method can be used to provide primary and/or urgent care services in four (4) simple steps:

Step 1—User begins/completes check-in process via web portal or at the mirror/personal medical kiosk. The user can optionally begin the check-in via web portal and then later complete check-in process at the mirror/personal medical kiosk; however, this is not required. A medical provider can send a reminder to user regarding an appointment and/or begin the check-in process for a user (e.g., follow-up appointment, etc.); however, this is not required.

Step 2—Medical provider receives eligible request and accepts and/or is assigned to user.

Step 3—User visits the mirror/personal medical kiosk and has a private appointment with a doctor via the User Screen.

Step 4—Visit is completed.

The mirror/personal medical kiosk and/or medical provider can then provide additional care/services that include: prescription, billing information, education, referrals, follow up and/or EMR/PHR entry. The medical provider can cause the mirror/personal medical kiosk to printout a prescription and/or directly send the prescription request to a pharmacy. The mirror/personal medical kiosk can print out a bill after the medical services are provided and/or accept payment prior to or after medical services are provided. The mirror/personal medical kiosk can be designed to accept and/or process medical insurance information provided by the user. The mirror/personal medical kiosk can print out and/or display education materials/information relevant to/requested by the user and/or provided by the medical provider. The mirror/personal medical kiosk and/or medical provider and/or attendant can schedule a follow-up visit for the user. Email, twitter, Facebook, test, and/or mail reminders can be sent to the user regarding scheduled and/or follow-up visits. The medical provider and/or attendant can schedule a visit with another medical provider and/or admit the user to the hospital, contact an ambulance, etc. during or after the visit to the mirror/personal medical kiosk. A visit summary can be printed out and/or sent to the user. As can be appreciated, the mirror/personal medical kiosk and method for using the mirror/personal medical kiosk can have other or additional features.

Advantageous portal features of the mirror/personal medical kiosk and associated medical method are:

Practice Management Engine.
Appointments Scheduling Engine.
Online Eligibility, Claims, and Billing Engine.
ePrescribing with Alerts and Reminder Engine.
Medical Records Interface and Access.
Personal Health Record (PHR).
Electronic Medical Record (EMR).
Rules-Based Care Plans.
Rules-Based Education.
Check In Pathway to Care Engine.
Secure Video Conferencing Engine.
Documentation Module.
Appointment Storage and Analysis.
Education and Post Care.

Some non-limiting advantages to users by use of the mirror/personal medical kiosk and medical method include Convenient, Closer to home, Saves time, Language and culture friendly, Better Access, Personal doctor available while traveling, Larger selection of doctors, Not limited by doctor's visitation schedule, More Accurate, Review record of appointment, Automatic data entry into PHR, Less Exposure to Illness.

Some non-limiting advantages to medical providers by use of the mirror/personal medical kiosk and medical method are: Higher Revenues. More appointments/day. Less traveling. More Accurate. Review record of appointment. Automatic data entry into EMR/HER. Integrated Care. Referral and transfer. Load Balancing. Appointment load can be shared with other doctors regardless of location.

The mirror/personal medical kiosk of the present invention is an Integrated Care Terminal that is a highly equipped doctor's office that is built and designed to deliver urgent and minor medical care in the field utilizing a centralized team of doctors for the evaluation and treatment of users. The mirror/personal medical kiosk can be fitted with the latest FDA approved medical devices used by doctors today. Employing the latest technology that is used in physician offices and emergency rooms, the mirror/personal medical kiosk is able to allow users to obtain appropriate care in locations that are convenient, accessible, and more affordable.

The interior of the mirror/personal medical kiosk can contain one or more of the following integrated medical devices:

Thermometer (e.g., temperature taken via ear, temperature taken via ear, IR thermometer to scan head or other area of body, etc.).
Scale built into the user seat or floor for measuring the user's weight.
Otoscope—for examining the middle ear, exterior ear, nasal passages, mouth and throat.
Oximeter which measures the blood oxygen saturation.
Stethoscope for evaluation of heart, lung and bowel sounds.
Blood Pressure Cuff to measure blood pressure.

EKG which provides a snapshot of the heart rhythm and data regarding stress or injury to the heart muscle.

Spirometer and transducer for measuring lung function.

Blood glucose measuring device or monitor.

Retinal scan device (e.g., Itronix retinal scan device, etc.).

Dermascope, or Derma-Camera.

A medical attendant (e.g., medical assistant, nurse assistant, nurse, nurse practitioner, physician, etc.) who resides outside the mirror/personal medical kiosk can be responsible for answering user questions, assisting with user registration/payment, thoroughly clean the mirror/personal medical kiosk after each use, and restock and/or reset the mirror/personal medical kiosk after each use. The cleaning of the mirror/personal medical kiosk can include sanitizing the seat, touch screen, floor, walls, seat, and all instruments as well as ensuring the mirror/personal medical kiosk is free of debris and any user belongings. The mirror/personal medical kiosk can also be designed to be automatically sterilized after one or more users use the mirror/personal medical kiosk by utilizing a chemical mist sterilization technology and/or UV sterilization technology. The medical attendant can also ensure that any insurance forms required by the user/user for reimbursement are provided via a printer or some other means contained in the exterior and/or interior of the mirror/personal medical kiosk.

The mirror/personal medical kiosk can also contain one or more computers, which are connected to the internet and powers the one or more monitors and/or other type of equipment in the mirror/personal medical kiosk; however, this is not required. The exterior monitor on the mirror/personal medical kiosk can be used for user registration and appointment selection that can be conducted in a touch screen format.

The method for providing medical services via a mirror/personal medical kiosk regarding protocols for scheduling, diagnosing, delivering and documenting tele-medicine primary care can include:

a. Medical Provider Application—this application is used by the medical provider to provide clinical services. The application contains all that the medical provider requires to diagnose, deliver care and document the clinical episode. It runs on the physician's computer and can be integrated with the leading EMR applications.

b. User Application—this application is used by the user to register with a mirror/personal medical kiosk and also captures the user's medical history and/or vitals. It includes all the information required to administer clinical services to the user. This includes financial/billing information and a Healthspot Electronic Medical Record (EMR), which can be accessed by the user and the medical providers.

c. Integrated videoconferencing software—this application supports the live user-clinician interaction required for delivery of the clinical services. It uses a secure connection to the servers and the provider via an internet connection. The software shares the information from the following devices:

Thermometer—(e. g., temperature taken via ear, temperature taken via ear, IR thermometer to scan head or other area of body, etc.

Scale built into the user seat or floor for measuring the user's weight.

Otoscope—for examining the middle ear, exterior ear, nasal passages, mouth and throat.

Oximeter which measures the blood oxygen saturation.

Stethoscope for evaluation of heart, lung and bowel sounds.

Blood Pressure Cuff to measure blood pressure.

EKG which provides a snapshot of the heart rhythm and data regarding stress or injury to the heart muscle.

Spirometer and transducer for measuring lung function.

Blood Glucose measurement device and/or monitor to measure blood glucose levels.

Retinal scan device to view structures in the eye.

Dermascope, or Derma-Camera to view the skin and/or throat.

Blood analyzer to measure different chemicals in the blood (e.g., glucose, serum albumin, creatinine, etc.) and/or other characteristics of the blood (e.g., blood cell count, enzyme levels, ion levels, measure ability of blood to clot, etc.).

DNA Sequencer/Mass Spectrometer

Because of the many germs and other contaminants that will be inside the mirror/personal medical kiosk, a sterilization technology can be used in the mirror/personal medical kiosk, One type of sterilization system that can be used is a built-in sanitizing misting system that dispenses from a series of misters between every appointment. Another or additional sterilization system that can be used is a UV lighting system that can be blasted between appointments. The one or more cleaning/sanitizing systems can be used to clean the air in the mirror/personal medical kiosk, clean one or more surfaces of the mirror/personal medical kiosk (e.g., floor, bench, display screen, cabinet surfaces, chair, etc.) and/or a portion of all of the surfaces of a medical device. Other techniques and technologies can also or alternatively be used. The attendant can have the ability to activate one or more sterilization systems (e.g., via button, computer, etc.). The attendant can be required to keep track of records about the sanitization process and can ensure that the doors to the mirror/personal medical kiosk are closed/locked during the sterilization process.

Video/Audio Conferencing—The user will communicate with the medical provider via video and audio conferencing technology. This environment can make the user feel as close to the medical provider as actually being present as possible. A two-way glass can be used to place the camera in the center of the monitor to keep the user looking head on, versus the Skype and current video conferencing solutions that keep users looking at the camera and back to the monitor.

Video Playback—The recorded medical session can be partially or fully reviewed by the user to enable the user to again listen to information, instructions and/or advise from the medical provider. As can be appreciated, the video playback feature can also or alternatively be used for auditing purposes, compliance purposes, security purposes, quality control purposes, etc.

Mirror Learning Machine

The mirror can identify new fashion styles by learning from the user's preferences and/or social network information. For example the system can learn that the user prefers certain celebrities or friends' style and apply this style to the user's fashion style. In some example embodiments, a system and method is shown for fashion matching that interprets a user's style or fashion and finds a match given a set of fashion items. A fashion is a style of dress, while a fashion item includes an article of clothing, jewelry, or anything that is used to denote a style of dress. In addition to the user's existing style and wardrobe, the mirror can add potentially interesting items or styles to the digital closet for the user by automatically retrieving style information from other social networking sites such as Facebook, Twitter, Pinterest, LinkedIn, Instagram and other such social sites for the purpose of more meaningful fashion and style match.

Some examples are, the system may retrieve and store user habits, i.e., TV shows, radio programs, songs, record albums, particular artists and actors and movies the user likes as well as user preferences, geographical location, school, other network affiliation, age, likes, recent activity, images viewed, searches etc. and much more variety of information via social network APIs. To incentivize the user to upload more images of themselves thereby building a large database, the system may assign points to the user each time the user interacts with the system. Some examples of system interaction are: a user uploads their own image with a new outfit, the user uploads another user's image and labels it and links it with that user's profile name.

The mirror can be assisted with a number of learning machines, including neural networks, case-based reasoning, Bayesian networks (including hidden Markov models), or fuzzy systems. The Bayesian networks may include: machine learning algorithms including—supervised learning, unsupervised learning, semi-supervised learning, reinforcement learning, transduction, learning to learn algorithms, or some other suitable Bayesian network. The neural networks may include: Kohonen self-organizing network, recurrent networks, simple recurrent networks, Hopfield networks, stochastic neural networks, Boltzmann machines, modular neural networks, committee of machines, Associative Neural Network (ASNN), holographic associative memory, instantaneously trained networks, spiking neural networks, dynamic neural networks, cascading neural networks, neuro-fuzzy networks, or some other suitable neural network. Further, the neural networks may include: machine learning algorithms including—supervised learning, unsupervised learning, semi-supervised learning, reinforcement learning, transduction, learning to learn algorithms, or some other suitable learning methods.

The system may use knowledge-based components such as a knowledge-based repository (KB). The repository may include clinical information. For example, it may include that "eating salt-rich food causes blood pressure to increase." The information may be stored in a variety of formats based on the type of inference employing them. The knowledge-based repository may act as a repository for some or all of the referenced knowledge. For example, it can include reference values for certain consents and variables used for inference. Accordingly, one or more layers (e.g. a hierarchical pattern processing layer or Pattern Engine) may subscribe to information from the knowledge-based repository. For example, one or more of the services may query the knowledge-based repository when making an inference.

In one embodiment, the knowledge-based repository may aggregate relevant clinical and/or behavioral knowledge from one or more sources. In an embodiment, one or more clinical and/or behavioral experts may manually specify the required knowledge. In another embodiment, an ontology-based approach may be used. For example, the knowledge-based repository may leverage the semantic web using techniques, such as statistical relational learning (SRL). SRL may expand probabilistic reasoning to complex relational domains, such as the semantic web. The SRL may achieve this using a combination of representational formalisms (e.g., logic and/or frame based systems with probabilistic models). For example, the SRL may employ Bayesian logic or Markov logic. For example, if there are two objects—'Asian male' and 'smartness', they may be connected using the relationship 'asian males are smart'. This relationship may be given a weight (e.g., 0.3). This relationship may vary from time to time (populations trend over years/decades). By leveraging the knowledge in the semantic web (e.g., all references and discussions on the web where 'asian male' and 'smartness' are used and associated) the degree of relationship may be interpreted from the sentiment of such references (e.g., positive sentiment: TRUE; negative sentiment: FALSE). Such sentiments and the volume of discussions may then be transformed into weights. Accordingly, although the system originally assigned a weight of 0.3, based on information from semantic web about Asian males and smartness, may be revised to 0.9.

In an embodiment, Markov logic may be applied to the semantic web using two objects: first-order formulae and their weights. The formulae may be acquired based on the semantics of the semantic web languages. In one embodiment, the SRL may acquire the weights based on probability values specified in ontologies. In another embodiment, where the ontologies contain individuals, the individuals can be used to learn weights by generative learning. In some embodiments, the SRL may learn the weights by matching and analyzing a predefined corpora of relevant objects and/or textual resources. These techniques may be used to not only to obtain first-order waited formulae for clinical parameters, but also general information. This information may then be used when making inferences.

For example, if the first order logic is 'obesity causes hypertension, there are two objects involved: obesity and hypertension. If data on users with obesity and as to whether they were diagnosed with diabetes or not is available, then the weights for this relationship may be learnt from the data. This may be extended to non-clinical examples such as person's mood, beliefs etc.

The pattern recognizer may use the temporal dimension of data to learn representations. The pattern recognizer may include a pattern storage system that exploits hierarchy and analytical abilities using a hierarchical network of nodes. The nodes may operate on the input patterns one at a time. For every input pattern, the node may provide one of three operations: 1. Storing patterns, 2. Learning transition probabilities, and 3. Context specific grouping.

A node may have a memory that stores patterns within the field of view. This memory may permanently store patterns and give each pattern a distinct label (e.g. a pattern number). Patterns that occur in the input field of view of the node may be compared with patterns that are already stored in the memory. If an identical pattern is not in the memory, then the input pattern may be added to the memory and given a distinct pattern number. The pattern number may be arbitrarily assigned and may not reflect any properties of the pattern. In one embodiment, the pattern number may be encoded with one or more properties of the pattern.

In one embodiment, patterns may be stored in a node as rows of a matrix. In such an embodiment, C may represent a pattern memory matrix. In the pattern memory matrix, each row of C may be a different pattern. These different patterns may be referred to as C-1, C-2, etc., depending on the row in which the pattern is stored.

The nodes may construct and maintain a Markov graph. The Markov graph may include vertices that correspond to the store patterns. Each vertex may include a label of the pattern that it represents. As new patterns are added to the memory contents, the system may add new vertices to the Markov graph. The system may also create a link between to vertices to represent the number of transition events between the patterns corresponding to the vertices. For example, when an input pattern is followed by another input pattern j for the first time, a link may be introduced between the vertices i and j and the number of transition events on that link may be set to 1. System may then increment the number of transition counts on the link from i and j whenever a pattern from i to pattern j is observed. The system may normalize the Markov graph such that the links estimate the probability of a transaction. Normalization may be achieved by dividing the number of transition events on the outgoing links of each vertex by the total number of transition events from the vertex. This may be done for all vertices to obtain a normalized Markov graph. When normalization is completed, the sum of the transition probabilities for each node should add to 1. The system may update the Markov graph continuously to reflect new probability estimates.

The system may also perform context-specific grouping. To achieve this, the system may partition a set of vertices of the Markov graph into a set of temporal groups. Each temporal group may be a subset of that set of vertices of the Markov graph. The partitioning may be performed such that the vertices of the same temporal group are highly likely to follow one another.

The node may use Hierarchical Clustering (HC) to for the temporal groups. The HC algorithm may take a set of pattern labels and their pair-wise similarity measurements as inputs to produce clusters of pattern labels. The system may cluster the pattern labels such that patterns in the same cluster are similar to each other.

In one embodiment, the probability of a transition between two patterns may be used as the similarity between those patterns for the HC algorithm. The similarity metric may be used to cluster medical patterns that are likely to follow one another into the same cluster. The HC algorithm may be configured such that patterns that are unlikely to follow each other fall into different clusters. A cluster of a set of patterns that are likely to follow each other in time may be referred to as a temporal group. The HC algorithm may start with all store patterns and separate clusters and then recursively merge clusters with the greatest similarity. This may be used to obtain a treelike structure (e.g. a dendrogram) with a single cluster (which may contain all patterns) at the top of the tree and the individual patterns at the bottom (e.g. each pattern in its own cluster). The system may achieve the desired clustering for temporal grouping (e.g. somewhere between the bottom and a top of the dendrogram) by defining a suitable criteria. For example, one criterion could be to cut the tree at a level where the size of the largest cluster does not exceed a particular value. The node may have a design perimeter that sets the maximum number of clusters or temporal groups of the node. The desired temporal groups may be achieved by selecting a level of the dendrogram that gives the number of temporal groups closest to and less than the configured maximum number of temporal groups. These temporal groups may be updated as the Markov transition probabilities are updated. These steps may be performed periodically during the learning process. The learning process may be stopped once the temporal groups have sufficiently stabilized.

Once a node has completed its learning process, it may be used for sensing and/or inference. The characteristics of the input to the node in sensing may be identical to those used during learning. For example, objects may move under the field of view of the node and the node may see portions of those objects. The resulting patterns may be used as inputs to the node.

A node used for sensing and/or inference may produce an output for every input pattern. A node may also use a sequence of patents to produce an output. In one embodiment, it can be assumed that the outputs are produced based on instantaneous inputs. Under this assumption, the Markov graph may not be used during the sensing phase. For example, it may be discarded once the temporal groups within the node are completed.

For every input pattern, the node may produce an output factor that indicates the degree of membership of the input pattern and each of its temporal groups. However, the current input pattern may not perfectly match any of the patterns stored in memory. Accordingly, in one embodiment, the closeness of the input pattern to every pattern stored in memory will be determined. For example, let di be the distance of the ith stored pattern from the input pattern. The larger this distance is, the smaller the match between the input pattern and the stored pattern becomes. Assuming that the probability that an input pattern matches a stored pattern falls off as a Gaussian function of the Euclidean distance, the probability that the input pattern matches the ith stored pattern can be calculated as being proportional to e−d2i/α, where a is a parameter of the node. Calculating this for every stored pattern may give the closeness of the current input pattern to all the vertices of the Markov graph.

Degree of membership of the input pattern in each temporal group may be determined by the maximum of its closeness to each of the vertices within the temporal group. This results in a length equal to the number of temporal groups, with each component of the factor indicating the degree of membership of the input pattern in the corresponding temporal group. This factor may then be used normalize the sum to unity. These normalized memberships may be used as estimates of probability of membership in each temporal group. This normalized degree of membership may also be used as an output of the node. The output may be a histogram giving estimates of probability of membership of the current input pattern and each of the temporal groups of the node.

As data is fed into the pattern recognizer, the transition probabilities for each pattern and pattern-of-patterns may be updated based on the Markov graph. This may be achieved by updating the constructed transition probability matrix. This may be done for each pattern in every category of patterns. Those with higher probabilities may be chosen and placed in a separate column in the database called a prediction list.

Logical relationships among the patterns may be manually defined based on the clinical relevance. This relationship is specified as first-order logic predicates along with probabilities. These probabilities may be called beliefs. In one embodiment, a Bayesian Belief Network (BBN) may be used to make predictions using these beliefs. The BBN may be used to obtain the probability of each occurrence. These logical relationships may also be based on predicates stored the knowledge base.

The pattern recognizer may also perform optimization for the predictions. In one embodiment, this may be accomplished by comparing the predicted probability for a relationship with its actual occurrence. Then, the difference between the two may be calculated. This may be done for p occurrences of the logic and fed into a K-means clustering algorithm to plot the Euclidean distance between the points. A centroid may be obtained by the algorithm, forming the optimal increment to the difference. This increment may then be added to the (p+1)th occurrence. Then, the process may be repeated. This may be done until the pattern recognizer predicts logical relationships up to a specified accuracy threshold. Then, the results may be considered optimal.

When a node is at the first level of the hierarchy, its input may come directly from the data source, or after some preprocessing. The input to a node at a higher-level may be the concatenation of the outputs of the nodes that are directly connected to it from a lower level. Patterns in higher-level nodes may represent particular coincidences of their groups of children. This input may be obtained as a probability distribution function (PDF). From this PDF, the probability that a particular group is active may be calculated as the probability of the pattern that has the maximum likelihood among all the patterns belonging to that group.

The system can use an expert system that can assess hypertension in according with the guidelines. In addition, the expert system can use diagnostic information and apply the following rules to assess hypertension:

Hemoglobin/hematocrit: Assesses relationship of cells to fluid volume (viscosity) and may indicate risk factors such as hypercoagulability, anemia.

Blood urea nitrogen (BUN)/creatinine: Provides information about renal perfusion/function.

Glucose: Hyperglycemia (diabetes mellitus is a precipitator of hypertension) may result from elevated catecholamine levels (increases hypertension).

Serum potassium: Hypokalemia may indicate the presence of primary aldosteronism (cause) or be a side effect of diuretic-therapy.

Serum calcium: Imbalance may contribute to hypertension.

Lipid panel (total lipids, high-density lipoprotein [HDL], low-density lipoprotein [LDL], cholesterol, triglycerides, phospholipids): Elevated level may indicate predisposition for/presence of atheromatous plaques.

Thyroid studies: Hyperthyroidism may lead or contribute to vasoconstriction and hypertension.

Serum/urine aldosterone level: May be done to assess for primary aldosteronism (cause).

Urinalysis: May show blood, protein, or white blood cells; or glucose suggests renal dysfunction and/or presence of diabetes.

Creatinine clearance: May be reduced, reflecting renal damage.

Urine vanillylmandelic acid (VMA) (catecholamine metabolite): Elevation may indicate presence of pheochromocytoma (cause); 24-hour urine VMA may be done for assessment of pheochromocytoma if hypertension is intermittent.

Uric acid: Hyperuricemia has been implicated as a risk factor for the development of hypertension.

Renin: Elevated in renovascular and malignant hypertension, salt-wasting disorders.

Urine steroids: Elevation may indicate hyperadrenalism, pheochromocytoma, pituitary dysfunction, Cushing's syndrome.

Intravenous pyelogram (IVP): May identify cause of secondary hypertension, e.g., renal parenchymal disease, renal/ureteral-calculi.

Kidney and renography nuclear scan: Evaluates renal status (TOD).

Excretory urography: May reveal renal atrophy, indicating chronic renal disease.

Chest x-ray: May demonstrate obstructing calcification in valve areas; deposits in and/or notching of aorta; cardiac enlargement.

Computed tomography (CT) scan: Assesses for cerebral tumor, CVA, or encephalopathy or to rule out pheochromocytoma.

Electrocardiogram (ECG): May demonstrate enlarged heart, strain patterns, conduction disturbances. Broad, notched P wave is one of the earliest signs of hypertensive heart disease.

The system may also be adaptive. In one embodiment, every level has a capability to obtain feedback information from higher levels. This feedback may inform about certain characteristics of information transmitted bottom-up through the network. Such a closed loop may be used to optimize each level's accuracy of inference as well as transmit more relevant information from the next instance.

The system may learn and correct its operational efficiency over time. This process is known as the maturity process of the system. The maturity process may include one or more of the following flow of steps:

a. Tracking patterns of input data and identifying predefined patterns (e.g. if the same pattern was observed several times earlier, the pattern would have already taken certain paths in the hierarchical node structure).

b. Scanning the possible data, other patterns (collectively called Input Sets (IS)) required for those paths. It also may check for any feedback that has come from higher levels of hierarchy. This feedback may be either positive or negative (e.g., the relevance of the information transmitted to the inferences at higher levels). Accordingly, the system may decide whether to send this pattern higher up the levels or not, and if so whether it should it send through a different path.

c. Checking for frequently required ISs and pick the top 'F' percentile of them.

d. Ensuring it keeps this data ready.

In one embodiment, information used at every node may act as agents reporting on the status of a hierarchical network. These agents are referred to as Information Entities (In En). In En may provide insight about the respective inference operation, the input, and the result which collectively is called knowledge.

This knowledge may be different from the KB. For example, the above described knowledge may include the dynamic creation of insights by the system based on its inference, whereas the KB may act as a reference for inference and/or analysis operations. The latter being an input to inference while the former is a product of inference. When this knowledge is subscribed to by a consumer (e.g. administering system or another node in a different layer) it is called "Knowledge-as-a-Service (KaaS)"

One embodiment processes behavior models are classified into four categories as follows:
a. Outcome-based;
b. Behavior-based;
c. Determinant-based; and
d. Intervention-based.

One or more of the following rules of thumb may be applied during behavioral modeling:
One or more interventions affect determinants;
One or more determinants affect behavior; and
One or more behaviors affect outcome.

A behavior is defined to be a characteristic of an individual or a group towards certain aspects of their life such as health, social interactions, etc. These characteristics are displayed as their attitude towards such aspects. In analytical terms, a behavior can be considered similar to a habit. Hence, a behavior may be observed for a given data from a user. An example of a behavior is dietary habits.

Determinants may include causal factors for behaviors. They either cause someone to exhibit the same behavior or cause behavior change. Certain determinants are quantitative but most are qualitative. Examples include one's perception about a food, their beliefs, their confidence levels, etc.

Interventions are actions that affect determinants. Indirectly they influence behaviors and hence outcomes. System may get both primary and secondary sources of data. Primary sources may be directly reported by the end-user and AU. Secondary data may be collected from sensors such as their mobile phones, cameras, microphone, as well as those collected from general sources such as the semantic web.

These data sources may inform the system about the respective interventions. For example, to influence a determinant called forgetfulness which relates to a behavior called medication, the system sends a reminder at an appropriate time, as the intervention. Then, feedback is obtained whether the user took the medication or not. This helps the system in confirming if the intervention was effective.

The system may track a user's interactions and request feedback about their experience through assessments. The system may use this information as part of behavioral modeling to determine if the user interface and the content delivery mechanism have a significant effect on behavior change with the user. The system may use this information to optimize its user interface to make it more personalized over time to best suit the users, as well as to best suit the desired outcome.

The system also may accommodate data obtained directly from the end-user, such as assessments, surveys, etc. This enables users to share their views on interventions, their effectiveness, possible causes, etc. The system's understanding of the same aspects is obtained by way of analysis and service by the pattern recognizer.

Both system-perceived and end user-perceived measures of behavioral factors may be used in a process called Perception Scoring (PS). In this process, hybrid scores may be designed to accommodate both above mentioned aspects of behavioral factors. Belief is the measure of confidence the system has, when communicating or inferring on information. Initially higher beliefs may be set for user-perceived measures.

Over time, as the system finds increasing patterns as well as obtains feedback in pattern recognizer, the system may evaluate the effectiveness of intervention(s). If the system triggers an intervention based on user-perceived measures and it doesn't have significant effect on the behavior change, the system may then start reducing its belief for user-perceived measures and instead will increase its belief for system-perceived ones. In other words, the system starts believing less in the user and starts believing more in itself. Eventually this reaches a stage where system can understand end-users and their behavioral health better than end-users themselves. When perception scoring is done for each intervention, it may result in a score called Intervention Effectiveness Score (IES).

Perception scoring may be done for both end-users as well as AU. Such scores may be included as part of behavior models during cause-effect analysis.

Causes may be mapped with interventions, determinants, and behavior respectively in order of the relevance. Mapping causes with interventions helps in back-tracking the respective AU for that cause. In simple terms, it may help in identifying whose actions have had a pronounced effect on the end-user's outcome, by how much and using which intervention. This is very useful in identifying AUs who are very effective with specific interventions as well as during certain event context. Accordingly, they may be provided a score called Associated User Influence Score. This encompasses information for a given end-user, considering all interventions and possible contexts relevant to the user's case.

The system may construct one or plans including one or more interventions based on analysis performed, and may be implemented. For example, the system may analyze eligibility of an intervention for a given scenario, evaluating eligibility of two or more interventions based on combinatorial effect, prioritizing interventions to be applied, based on occurrence of patterns (from pattern recognizer), and/or submitting an intervention plan to the user or doctor in a format readily usable for execution.

This system may rely on the cause-effect analysis for its planning operations. A plan consists of interventions and a respective implementation schedule. Every plan may have several versions based on the users involved in it. For example, the system may have a separate version for the physician as compared to a user. They will in turn do the task and report back to the system. This can be done either directly or the system may indirectly find it based on whether a desired outcome with the end user was observed or not.

The methodology may be predefined by an analyst. For every cause, which can be an intervention(s), determinant(s), behavior(s) or combinations of the same, the analyst may specify one or more remedial actions. This may be specified from the causal perspective and not the contextual perspective.

This approach uses the idea of situation-aware metadata description framework meaning that context specific information for all possible contexts specified in the meta data during system design. This process may be done for every cause, thereby specifying what remedial actions are more appropriate for it and for what context.

Accordingly, a set of remedial actions may be confirmed by determining which users should participate in the intervention plan and how. For example, if a physician had a high score for improving confidence of a user, the intervention plan may consider that fact and include one of the interventions to be motivational interviewing of the user by that physician, provided the cause-effect analysis confirms it with a closely associated cause.

The system may optimize its plan to ensure that it reflects a smooth transition between plans (current versus new) and hence interventions to the end user. The rules for such optimizations may be manually specified by the analyst during the design.

The system may include selecting appropriate presentation mode (e.g. web or mobile) as well as device (e.g. phone or tablet) based on the intervention specified, mapping rules to each intervention based on plan, operating both proactively (based on predefined plan) and reactively (feedback-based inference engine), obtaining feedback about the end-user from system usage and self-reporting, facilitating data to the pattern recognizer and hence made the overall end-to-end system a reflexive feedback system, and/or calling the pattern recognizer on-demand. In the use case, the user may be presented with articles related to the consumption of carbohydrates, given one or more carbohydrate-counting goals, and/or receive one or more notifications to perform a task, such as instructions to reduce salt in the diet, pick up medication or exercise.

There may be a communication component within every presentation channel that accepts its version of the plan through a secured communication protocol. There may also be an execution component within every presentation layer that will take care of starting the new plan at a calculated period before the completion of the current plan. This ensures that the transition between plans is smooth enough for the users to not experience a drastic change in interventions. Also, the execution component may also suppress certain flows of delivering content in the inference engine based on the new plan. This ensures that the users are not sent contents from two plans which may look confusing. Considering the context, either the new plan or the current plan may be preferred over the other. This component also may manage between both plans simultaneously, if necessary.

Every presentation channel may be associated with a presentation device. The capabilities and various sensory data input options of the device may be used by inference engine. The device-specific version of the plan is meant to address this issue. In certain cases, such as mobile phones, handheld devices, etc., where camera and microphone is available, a specific pattern recognition engine takes specific samples of pictorial, video and auditory data, using camera and microphone, and then compare it with predefined categories of emotions. Hence, it may perform a pattern classification operation. The engine may be pre-trained with example data in these formats for those respective categories. The pattern recognition mechanism may be similar to the one performed by pattern recognizer. But in this engine, the focus may be on only sensory inputs and basic classification. Thus, it may not have any hierarchical layers of computation making it much simpler and more specific. After classification, it may compare the classification between the three sensory data sources and confirm the emotional state of the end user using suitable algorithms. This feature becomes a valuable source of information that may be used by different services for making psychological and behavioral inferences.

Accordingly, the system may send a variety of data and information to pattern recognizer and other services, as feedback, for these services to understand about the users. This understanding may affect their next set of plans which in turn becomes an infinite cyclic system where system affects the users while getting affected by them at the same time. Such a system is called a reflexive-feedback enabled system. The system may user both positive and negative reflexive-feedback, though the negative feedback aspect may predominantly be used for identifying gaps that the system needs to address.

The system may provide information, such as one or more newly identified patterns, to an analyst (e.g., clinical analyst or doctor). In the use case, the doctor may be presented with one or more notifications to address the relationship between carbohydrates and the medication that the user is taking.

One embodiment of the system operation includes receiving feedback relating to the plan, and revising the plan based on the feedback; the feedback being one or more user behaviors that occur after the plan; the revised plan including one or more additional interventions selected based on the feedback; the one or more user behaviors that occur after the plan include a behavior transition; determining one or more persons to associate with the identified intervention; automatically revising probabilities from the collected information; storing the revised probabilities, wherein the revised probabilities are used to determine the plan; and/or automatically make one or more inferences based on machine learning using one or more of the clinical information, behavior information, or personal information.

Hypertension metrics may be one type of metrics utilized within the principles of the present disclosure. A hypertension score can be based on any type of alpha-numeric or visual analog scale. Hypertension scales may or may not be clinically validated and may use any scale (e.g. 1-100, 1-10, 1-4), picture, symbol, color, character, number, sound, letter, or written description of hypertension to facilitate the communication of a user's hypertension level. The type of hypertension scale used may be determined according to a user's and/or healthcare provider's preferences, and may also be determined based on the needs of a user including, for example, the user's age and/or communication capability. In further embodiments, the selected hypertension scale(s) may be determined by a service provider, such as, e.g., an organization implementing the principles of the present disclosure via a suitable software program or application.

Another metric may include a functionality score. A functionality score can be based on any type of alpha-numeric or visual analog scale. Non-limiting examples include the American Chronic Pain Association Quality of Life (ACPA QoL) Scale, Global Assessment of Functioning (GAF) Scale, and Short Form SF-36 Health Survey. Functionality scales may or may not be clinically validated and may use any picture, symbol, color, character, number, sound, letter, written description of quality of life, or physical functioning to facilitate communication of a user's functionality level. The functionality score may be, e.g., based on an assessment of a user's ability to exercise as well as perform daily tasks and/or perform routine tasks such as, e.g., getting dressed, grocery shopping, cooking, cleaning, climbing stairs, etc. In some embodiments, the selected functionality scale(s) may be determined by a service provider, such as, e.g., an organization implementing the principles of the present disclosure via a suitable software program or application.

A further metric may include a user's medication usage. Medication use encompasses pharmacologic and therapeutic agents used to treat, control, and/or alleviate hypertension, including prescription drugs as well as over-the-counter medications, therapeutic agents, and other non-prescription agents. Medication use may include different classes of pharmacologic agents. Medication use can be reported in any appropriate units, such as number of doses taken, percentage of treatment plan completed, frequency of doses, and/or dose strength; and may also specify additional information such as the type of formulation taken and the route of administration (oral, enteral, topical, transdermal, parenteral, sublingual etc.). Molecular alternatives (e.g., acid, salt, solvate, complex, and pro-drug forms, etc.) and formulations (e.g., solid, liquid, powder, gel, and suspensions, etc.) are further contemplated. Reported medication use may, for example, include the number of doses and types of medication taken since a previous reported medication use, and may also indicate the number of closes and types of medication taken within a period of time, such as within, the previous 2 hours, 4 hours, 6 hours, 12 hours, 18 hours, 24 hours, 36 hours, or 48 hours. In some embodiments, for example, medication use may be reported in terms of dosage units recommended by a manufacturer or healthcare provider for a given medication (e.g., minimum, maximum, or range of appropriate unit dosage per unit time).

Reported medication use may allow for tracking compliance with a treatment regime. For example, a record of reported medication use may assist a healthcare provider in evaluating medication efficacy, adjusting dosage, and/or adding other medications as necessary.

In some embodiments of the present disclosure, a user or healthcare provider may create a user profile comprising, e.g., identifying, characterizing, and/or medical information, including information about a user's medical history, profession, and/or lifestyle. Further examples of information that may be stored in a user profile includes diagnostic information such as family medical history, medical symptoms, duration of hypertension, localized vs. general hypertension, etc. Further contemplated as part of a user profile are non-pharmacologic treatment(s) (e.g., chiropractic, radiation, holistic, psychological, acupuncture, etc.), lifestyle characteristics (e.g., diet, alcohol intake, smoking habits), cognitive condition, behavioral health, and social well-being.

A user profile may, for example, be stored in a database and accessible for analysis of the user's reported hypertension metrics. In some embodiments, a user profile may be created before collecting and/or transmitting a set of hypertension metrics to be received by a server and/or database In other embodiments, a user profile may be created concurrently with, or even after transmitting/receiving one or more hypertension metrics. In some embodiments a user profile may be used to establish one or more hypertension metric e and/or reference values. A user profile may, for example, allow for setting threshold values or ranges, wherein reported hypertension metrics that fall outside of those limits trigger an alert to be sent to the user or a healthcare provider. Threshold values, limits, or ranges may also be set without reference to a user profile. In some embodiments, one or more target value(s) (e.g., hypertension metric value(s)) may be set to determine how the reported hypertension metrics compare with the target value(s).

The methods and systems disclosed herein may rely on one or more algorithm(s) to analyze one or more of the described metrics. The algorithm(s) may comprise analysis of data reported in real-time, and may also analyze data reported in real-time in conjunction with auxiliary data stored in a hypertension management database. Such auxiliary data may comprise, for example, historical user data such as previously-reported hypertension metrics (e.g., hypertension scores, functionality scores, medication use), personal medical history, and/or family medical history. In some embodiments, for example, the auxiliary data includes at least one set of hypertension metrics previously reported and stored for a user. In some embodiments, the auxiliary data includes a user profile such as, e.g., the user profile described above. Auxiliary data may also include statistical data, such as hypertension metrics pooled for a plurality of users within a similar group or subgroup. Further, auxiliary data may include clinical guidelines such as guidelines relating to hypertension management, including evidence-based clinical practice guidelines on the management of acute and/or chronic hypertension or other chronic conditions.

Analysis of a set of hypertension metrics according to the present disclosure may allow for calibration of the level, degree, and/or quality of hypertension experienced by providing greater context to user-reported data. For example, associating a hypertension score of 7 out of 10 with high functionality for a first user, and the same score with low functionality for a second user may indicate a relatively greater debilitating effect of hypertension on the second user than the first user. Further, a high hypertension score reported by a user taking a particular medication such as opioid analgesics may indicate a need to adjust the user's treatment plan. Further, the methods and systems disclosed herein may provide a means of assessing relative changes in a user's distress due to hypertension over time. For example, a hypertension score of 5 out of 10 for a user who previously reported consistently lower hypertension scores, e.g., 1 out of 10, may indicate a serious issue requiring immediate medical attention.

Any combination(s) of hypertension metrics may be used for analysis in the systems and methods disclosed. In some embodiments, for example, the set of hypertension metrics comprises at least one hypertension score and at least one functionality score. In other embodiments, the set of hypertension metrics may comprise at least one hypertension score, at least one functionality score, and medication use. More than one set of hypertension metrics may be reported and analyzed at a given time. For example, a first set of hypertension metrics recording a user's current status and a second set of hypertension metrics recording the user's status at an earlier time may both be analyzed and may also be used to generate one or more recommended actions.

Each hypertension metric may be given equal weight in the analysis, or may also be given greater or less weight than other hypertension metrics included in the analysis. For example, a functionality score may be given greater or less weight with respect to a hypertension score and/or medication use. Whether and/or how to weigh a given hypertension metric may be determined according to the characteristics or needs of a particular user. As an example, User A reports a hypertension score of 8 (on a scale of 1 to 10 where 10 is the most severe hypertension) and a functionality score of 9 (on a scale of 1 to 10 where 10 is highest functioning), while User B reports a hypertension score of 8 but a functionality score of 4. The present disclosure provides for the collection, analysis, and reporting of this information, taking into account the differential impact of one hypertension score on a user's functionality versus that same hypertension score's impact on the functionality of a different user.

Hypertension metrics may undergo a pre-analysis before inclusion in a set of hypertension metrics and subsequent application of one or more algorithms. For example, a raw score may be converted or scaled according to one or more algorithm(s) developed for a particular user. In some embodiments, for example, a non-numerical raw score may be converted to a numerical score or otherwise quantified prior to the application of one or more algorithms. Users and healthcare providers may retain access to raw data (e.g., hypertension metric data prior to any analysis)

Algorithm(s) according, to the present disclosure may analyze the set of hypertension metrics according to any suitable methods known in the art. Analysis may comprise, for example, calculation of statistical averages, pattern recognition, application of mathematical models, factor analysis, correlation, and/or regression analysis. Examples of analyses that may be used herein include, but are not limited to, those disclosed in U.S. Patent Application Publication No. 2012/0246102 A1 the entirety of which is incorporated herein by reference.

The present disclosure further provides for the determination of an aggregated hypertension assessment score. In some embodiments, for example, a set of pairs metrics may be analyzed to generate a comprehensive and/or individualized assessment of hypertension by generating a composite or aggregated score. In such embodiments, the aggregated score may include a combination of at least one hypertension score, at least one functionality score, and medication use. Additional metrics may also be included in the aggregated score. Such metrics may include, but are not limited to, exercise habits, mental well-being, depression, cognitive functioning, medication side effects, etc. Any of the aforementioned types of analyses may be used in determining an aggregated score.

The algorithm(s) may include a software program that may be available for download to an input device in various versions. In some embodiments, for example, the algorithm(s) may be directly downloaded through the Internet or other suitable communications means to provide the capability to troubleshoot a health issue in real-time. The algorithm(s) may also be periodically updated, e.g., provided content changes, and may also be made available for download to an input device.

The methods presently disclosed may provide a healthcare provider with a more complete record of a user's day-to-day status. By having access to a consistent data stream of hypertension metrics for a user, a healthcare provider may be able to provide the user with timely advice and real-time coaching on hypertension management options and solutions. A user may, for example, seek and/or receive feedback on hypertension management without waiting for an upcoming appointment with a healthcare provider or scheduling a new appointment. Such real-time communication capability may be especially beneficial to provide users with guidance and treatment options during intervals between appointments with a healthcare provider. Healthcare providers may also be able to monitor a user's status between appointments to timely initiate, modify, or terminate a treatment plan as necessary. For example, a user's reported medication use may convey whether the user is taking too little or too much medication. In some embodiments, an alert may be triggered to notify the user and/or a healthcare provider of the amount of medication taken, e.g., in comparison to a prescribed treatment plan. The healthcare provider could, for example, contact the user to discuss the treatment plan. The methods disclosed herein may also provide a healthcare provider with a longitudinal review of how a user responds to hypertension over time. For example, a healthcare provider may be able to determine whether a given treatment plan adequately addresses a user's needs based on review of the user's reported hypertension metrics and analysis thereof according to the present disclosure.

Analysis of user data according to the methods presently disclosed may generate one or more recommended actions that may be transmitted and displayed on an output device. In some embodiments, the analysis recommends that a user make no changes to his/her treatment plan or routine. In other embodiments, the analysis generates a recommendation that the user seek further consultation with a healthcare provider and/or establish compliance with a prescribed treatment plan. In other embodiments, the analysis may encourage a user to seek immediate medical attention. For example, the analysis may generate an alert to be transmitted to one or more output devices, e.g., a first output device belonging to the user and a second output device belonging to a healthcare provider, indicating that the user is in need of immediate medical treatment. In some embodiments, the analysis may not generate a recommended action. Other recommended actions consistent with the present disclosure may be contemplated and suitable according to the treatment plans, needs, and/or preferences for a given user.

The present disclosure further provides a means for monitoring a user's medication use to determine when his/her prescription will run out and require a refill. For example, a user profile may be created that indicates a prescribed dosage and frequency of administration, as well as total number of dosages provided in a single prescription. As the user reports medication use, those hypertension metrics may be transmitted to a server and stored in a database in connection with the user profile. The user profile stored on the database may thus continually update with each added metric and generate a notification to indicate when the prescription will run out based on the reported medication use. The notification may be transmitted and displayed on one or more output devices, e.g., to a user and/or one or more healthcare providers. In some embodiments, the one or more healthcare providers may include a pharmacist. For example, a pharmacist may receive notification of the anticipated date a prescription will run out in order to ensure that the prescription may be timely refilled.

User data can be input for analysis according to the systems disclosed herein through any data-enabled device including, but not limited to, portable/mobile and stationary communication devices, and portable/mobile and stationary computing devices. Non-limiting examples of input devices suitable for the systems disclosed herein include smart phones, cell phones, laptop computers, netbooks, personal computers (PCs), tablet PCs, fax machines, personal digital assistants, and/or personal medical devices. The user interface of the input device may be web-based, such as a web page, or may also be a stand-alone application. Input devices may provide access to software applications via mobile and wireless platforms, and may also include web-based applications.

The input device may receive data by having a user, including, but not limited to, a user, family member, friend, guardian, representative, healthcare provider, and/or caregiver, enter particular information via a user interface, such as by typing and/or speaking. In some embodiments, a server may send a request for particular information to be entered by the user via an input device. For example, an input device may prompt a user to enter sequentially a set of hypertension metrics, e.g., a hypertension score, a functionality score, and information regarding use of one or more medications (e.g., type of medication, dosage taken, time of day, route of administration, etc.). In other embodiments, the user may enter data into the input device without first receiving a prompt. For example, the user may initiate an application or web-based software program and select an option to enter one or more hypertension metrics. In some embodiments, one or more hypertension scales and/or functionality scales may be preselected by the application or software program. For example, a user may have the option of selecting the type of hypertension scale and/or functionality scale for reporting hypertension metrics within the application or software program. In other embodiments, an application or software program may not include preselected hypertension scales or functionality scales such that a user can employ any hypertension scale and/or functionality scale of choice.

The user interface of an input device may allow a user to associate hypertension metrics with a particular date and/or time of day. For example, a user may report one or more hypertension metrics to reflect a user's present status. A user may also report one or more hypertension metrics to reflect a user's status at an earlier time.

User data may be electronically transmitted from an input device over a wired or wireless medium to a server, e.g., a remote server. The server may provide access to a database for performing an analysis of the data transmitted, e.g., set of hypertension metrics. The database may comprise auxiliary data for use in the analysis as described above. In some embodiments, the analysis may be automated, and may also be capable of providing real-time feedback to users and/or healthcare providers.

The analysis may generate one or more recommended actions, and may transmit the recommended action(s) over at wired or wireless medium for display on at least one output device. The at least one output device may include, e.g., portable/mobile and stationary communication devices, and portable/mobile and stationary computing devices. Non-limiting examples of output devices suitable for the systems disclosed herein include smart phones, cell phones, laptop computers, netbooks, personal computers (PCs), tablet PCs, fax machines, personal digital assistants, and/or personal medical devices. In some embodiments, the input device is the at least one output device. In other embodiments, the input device is one of multiple output devices. In some embodiments of the present disclosure, the one or more recommended actions are transmitted and displayed on each of two output devices. In such an example, one output device may belong to a user and the other device may belong to a healthcare provider.

The present disclosure also contemplates methods and systems in a language suitable for communicating with the user and/or healthcare provider, including languages other than English.

A user's medical data may be subject to confidentiality regulations and protection. Transmitting, analyzing, and/or storing information according to the methods and systems disclosed herein may be accomplished through secure means, including HIPPA-compliant procedures and use of password-protected devices, servers, and databases.

One embodiment shares data with different health portals such as Apple's Healthkit®, Samsung's Health database, and the US Government Blue Button, which is a nationally recognized symbol indicating to consumers that they can get their own health records electronically from doctors, hospitals, and other health care providers, such as pharmacies and health insurance plans. With electronic access to their health records, consumers can check them for accuracy and completeness, share them with people they trust—in case of emergency or to coordinate care among different providers—and reference them as needed. Health records may include clinical information from doctors and hospitals, health insurance claims, prescription histories, and lab/diagnostic test results. BlueButton.js parses and generates complex health data formats like C-CDA to allow the BP devices to empower users with access to their health records.

The systems and methods presently disclosed may be especially beneficial in outuser, home, and/or on-the-go settings. The systems and methods disclosed herein may also be used as an inuser tool and/or in controlled medication administration such as developing a personalized treatment plan.

In addition to monitoring health parameters, the system can include interventional devices such as a defibrillator. The defibrillator function is enabled by providing electrical energy of a selected energy/power level/voltage/current level or intensity delivered for a selected duration upon sensing certain patterns of undesirable heart activity wherein said undesirable heart activity necessitates an external delivery of a controlled electrical energy pulse for stimulating a selected heart activity. The defibrillator function is enabled by an intelligent defibrillator appliance that operates in a manner similar to the functions of an intelligent ECG appliance with the additional capability of providing external electrical stimuli via for example a wireless contact system pasted on various locations of the torso. The electrical stimuli are delivered in conjunction with the intelligent defibrillator device or the mobile device performing the additional functions of an intelligent defibrillator appliance. The control actions for providing real time stimuli to the heart of electrical pulses, is enabled by the intelligent defibrillator appliance by itself or in conjunction with an external server/intelligent appliance where the protocols appropriate for the specific individual are resident. The defibrillation actions are controlled in conjunction with the real time ECG data for providing a comprehensive real time solution to the individual suffering from abnormal or life threatening heart activity/myocardial infraction. Additionally, by continuously wearing the paste on wireless contacts that can provide the electrical impulse needed, the individual is instantaneously able to get real time attention/action using a specifically designed wearable intelligent defibrillator appliance or a combination of an intelligent ECG plus defibrillator appliance. Further the mobile device such as a cellular telephone or other wearable mobile devices can be configured with the appropriate power sources and the software for performing the additional functions of an intelligent defibrillator appliance specifically tailored to the individual.

The cellular telephone/mobile device can receive signals from the ECG machine/appliance or as an intermediary device that transmits/receives the ECG data and results from a stationary or portable ECG appliance. The ability of the individual to obtain an ECG profile of the heart at a selected time and in a selected location is critical to getting timely attention and for survival. Getting attention within 10 to 20 minutes of a heart attack is crucial beyond that the chances for survival diminish significantly. The smart phone helps the user to quickly communicate his/her location and or discover the location of the nearest health care facility that has the requisite cardiac care facilities and other facilities. The mobile device that the individual is carrying on the person is enabled to provide the exact location of the individual in conjunction with the global positioning system. In addition the system is enabled to provide the directions and estimated travel time to/from the health care facility to the specific mobile device/individual.

Yet other intervention can include music, image, or video. The music can be synchronized with respect to a blood pulse rate in one embodiment, and in other embodiments to biorhythmic signal—either to match the biorhythmic signal, or, if the signal is too fast or too slow, to go slightly slower or faster than the signal, respectively. In order to entrain the user's breathing, a basic melody is preferably played which can be easily identified by almost all users as corresponding to a particular phase of respiration. On top of the basic melody, additional layers are typically added to make the music more interesting, to the extent required by the current breathing rate, as described hereinabove. Typically, the basic melody corresponding to this breathing includes musical cords, played continuously by the appropriate instrument during each phase. For some applications, it is desirable to elongate slightly the length of one of the respiratory phases, typically, the expiration phase. For example, to achieve respiration which is 70% expiration and 30% inspiration, a musical composition written for an E:I ratio of 2:1 may be played, but the expiration phase is extended by a substantially-unnoticed 16%, so as to produce the desired respiration timing. The expiration phase is typically extended either by slowing down the tempo of the notes therein, or by extending the durations of some or all of the notes.

Although music for entraining breathing is described hereinabove as including two phases, it will be appreciated by persons skilled in the art that the music may similarly include other numbers of phases, as appropriate. For example, user may be guided towards breathing according to a 1:2:1:3 pattern, corresponding to inspiration, breath holding (widely used in Yoga), expiration, and post-expiratory pause (rest state).

In one embodiment, the volume of one or more of the layers is modulated responsive to a respiration characteristic (e.g., inhalation depth, or force), so as to direct the user to change the characteristic, or simply to enhance the user's connection to the music by reflecting therein the respiration characteristic. The 3D camera can detect breathing activity from chest movement and can provide instructions to reduce stress as detected by the facial expression or body slouching or low energy voice. The system can instruct the user to practice a yoga-like breathing and relaxation to reduce stress. Alternatively or additionally, parameters of the sound by each of the musical instruments may be varied to increase the user's enjoyment. For example, during slow breathing, people tend to prefer to hear sound patterns that have smoother structures than during fast breathing and/or aerobic exercise.

Further alternatively or additionally, random musical patterns and/or digitized natural sounds (e.g., sounds of the ocean, rain, or wind) are added as a decoration layer, especially for applications which direct the user into very slow breathing patterns. The inventor has found that during very slow breathing, it is desirable to remove the user's focus from temporal structures, particularly during expiration.

Still further alternatively or additionally, the server maintains a musical library, to enable the user to download appropriate music and/or music-generating patterns from the Internet into device. Often, as a user's health improves, the music protocols which were initially stored in the device are no longer optimal, so the user downloads the new protocols, by means of which music is generated that is more suitable for his new breathing training.

In one embodiment, the DNA sequencer can analyze a polynucleotide comprising nucleotides by making electrical measurements during translocation though a nanopore. Nanopores can determine the identity of the polynucleotide or to estimate the identity of individual nucleotides in the polynucleotide for sequencing purposes. This is because the method is label-free, provides measurements dependent on small numbers or even single molecules, and generates an electric signal that is highly scalable. In a measurement system utilizing a nanopore, some property of the system depends on the nucleotides in the nanopore, and electrical measurements of that property are taken. For example, a measurement system can be created by placing a nanopore in an insulating membrane and measuring voltage-driven ion flow through the nanopore in the presence of nucleotides of the polynucleotide. Depending on the nature of the nanopore, information about the nucleotides may be revealed by distinctive ion current signatures, such as the duration and extent of current block and the variance of current levels. Such types of measurement system using a nanopore has considerable promise, particularly in the field of sequencing a polynucleotide such as DNA or RNA, and has been the subject of much recent development. In one exemplary setup, a lipid membrane separates two aqueous chambers, containing an electrolyte such as KCl. Electrodes are placed in each aqueous reservoir, a potential was applied across the membrane and the ionic current between the two chambers was monitored. A 10× concentration stock solution containing the DNA analyte and the Phi29 DNAP is added to the solution. Enzyme-DNA binding events with multiple current states occur as the DNA unzipped through the pore. Runs are obtained at constant applied potential, occasionally reversing the potential to unblock the pore. Multiple DNA molecules can be moved through the nanopore over the duration of the run. Typical run conditions were: MS-(B1)8, 400 mM KCl, 10 mM Hepes, pH 8.0, 1 mM EDTA, 1 mM DTT, +180 mV. The final concentration of DNA analyte was run at 100 nM with 200 nM of Phi29 DNAP. Current levels were extracted from the raw data to generate an event trace. The levels from multiple molecules were aligned together to form a consensus plot of that molecule. Once the changes in current level have been detected, and the data is thus reduced to a sequence of discrete states, alignment of the states found for each DNA capture sequence can be performed to produce a single consensus sequence for the strand. A number of alignment methods exist that can be used for this purpose, including the Needleman-Wunsch and the Smith-Waterman algorithms, both based on the principles of Dynamic Programming. In cases where the number of possible states is small and each state is constrained to allow only a small subset of permitted subsequent states, more highly optimized heuristic or probabilistic methods can used.

Figure 6:
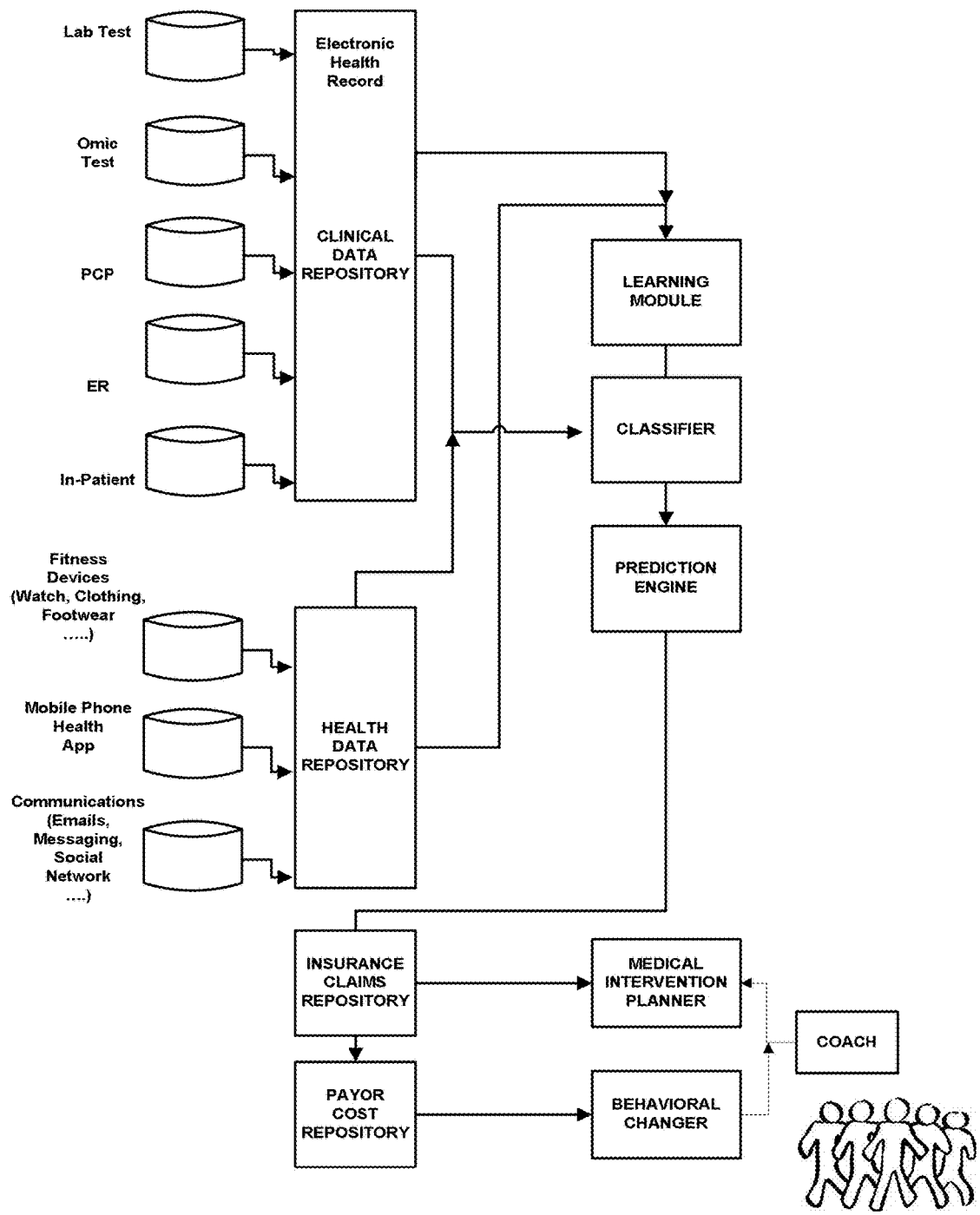
FIG. 6 shows an exemplary system for receiving health information from the mirrors and for mining health data as part of precision medicine.

FIG. 6 shows an exemplary system for mining health data for precision medicine. In this system, medical grade data from the mirror system of FIG. 1, and lab test equipment data are stored in a database. Omic test equipment also generates data that is stored in another database. EHR data from primary care physician (PHP), emergency room physicians (ER), and in-patient care data is also stored in a database. These databases form a clinical data repository that contains medical diagnosis and treatment information. The clinical data is high grade medical information that is secured by patient privacy laws such as HIPPA. One exemplary process for improving healthcare using precision medicine includes:
  obtain clinical data from mirror and 3d party laboratory test equipment
  obtain clinical data from one or more omic test equipment
  obtain clinical data from a primary care physician database
  obtain clinical data from a specialist physician database
  obtain clinical data from an emergency room database
  obtain clinical data from an in-patient care database
  save the clinical data into a clinical data repository
  obtain health data from fitness devices and from mobile phones
  obtain behavioral data from social network communications and mobile device usage patterns
  save the health data and behavioral data into a health data repository separate from the clinical data repository
  mine the clinical data repository and health data repository for patients sharing similarity with the subject, including one or more similar biomarkers associated with health conditions
  identify at least one similar health conditions and identifying one or more corrective actions recorded in the repository and the result of each action for the one or more health conditions;
  present the corrective action and result to the subject and recommending an action to reduce risk from the predicted health condition
  monitor the health condition using updates in the clinical data repository and health data repository In another embodiment for cost effective health maintenance, the system includes a method of insuring a subject for cancer, by:
  enrolling the subject into a cost-saving program;
  receiving a body sample during routine periodic examinations and characterizing the subject's omic information with a DNA sequencer; and
  using historical omic information to detect an occurrence of a disease such as cancer before the subject is suspected of having the disease; and
  proactively recommending early treatments based on the omic information received at each time interval to cost-effectively control disease.

Another exemplary process for applying the agents of FIG. 1A to a weight loss treatment scenario. The general goals of weight loss and management are: (1) at a minimum, to prevent further weight gain; (2) to reduce body weight; and (3) to maintain a lower body weight over the long term. The initial goal of weight loss therapy is to reduce body weight by approximately 10 percent from baseline. If this goal is achieved, further weight loss can be attempted, if indicated through further evaluation. A reasonable time line for a 10 percent reduction in body weight is 6 months of therapy. For overweight patients with BMIs in the typical range of 27 to 35, a decrease of 300 to 500 kcal/day will result in weight losses of about ½ to 1 lb/week and a 10 percent loss in 6 months. For more severely obese patients with BMIs>35, deficits of up to 500 to 1,000 kcal/day will lead to weight losses of about 1 to 2 lb/week and a 10 percent weight loss in 6 months. Weight loss at the rate of 1 to 2 lb/week (calorie deficit of 500 to 1,000 kcal/day) commonly occurs for up to 6 months. After 6 months, the rate of weight loss usually declines and weight plateaus because of a lesser energy expenditure at the lower weight.

After 6 months of weight loss treatment, efforts to maintain weight loss should be put in place. If more weight loss is needed, another attempt at weight reduction can be made. This will require further adjustment of the diet and physical activity prescriptions.

Dietary Therapy: A diet that is individually planned and takes into account the patient's overweight status in order to help create a deficit of 500 to 1,000 kcal/day should be an integral part of any weight loss program. Depending on the patient's risk status, the low-calorie diet (LCD) recommended should be consistent with the NCEP's Step I or Step II Diet. Besides decreasing saturated fat, total fats should be 30 percent or less of total calories. Reducing the percentage of dietary fat alone will not produce weight loss unless total calories are also reduced. Isocaloric replacement of fat with carbohydrates will reduce the percentage of calories from fat but will not cause weight loss. Reducing dietary fat, along with reducing dietary carbohydrates, usually will be needed to produce the caloric deficit needed for an acceptable weight loss. When fat intake is reduced, priority should be given to reducing saturated fat to enhance lowering of LDL-cholesterol levels. Frequent contacts with the practitioner during dietary therapy help to promote weight loss and weight maintenance at a lower weight.

An increase in physical activity is an important component of weight loss therapy, although it will not lead to substantially greater weight loss over 6 months. Most weight loss occurs because of decreased caloric intake. Sustained physical activity is most helpful in the prevention of weight regain. In addition, it has a benefit in reducing cardiovascular and diabetes risks beyond that produced by weight reduction alone. For most obese patients, exercise should be initiated slowly, and the intensity should be increased gradually. The exercise can be done all at one time or intermittently over the day. Initial activities may be walking or swimming at a slow pace. The patient can start by walking 30 minutes for 3 days a week and can build to 45 minutes of more intense walking at least 5 days a week. With this regimen, an additional expenditure of 100 to 200 calories per day can be achieved. All adults should set a long-term goal to accumulate at least 30 minutes or more of moderate-intensity physical activity on most, and preferably all, days of the week. This regimen can be adapted to other forms of physical activity, but walking is particularly attractive because of its safety and accessibility. Patients should be encouraged to increase "every day" activities such as taking the stairs instead of the elevator. With time, depending on progress and functional capacity, the patient may engage in more strenuous activities. Competitive sports, such as tennis and volleyball, can provide an enjoyable form of exercise for many, but care must be taken to avoid injury. Reducing sedentary time is another strategy to increase activity by undertaking frequent, less strenuous activities.

The communication system is used to provide Behavior Therapy. The system automatically sends messages using rule-based agents to communicate with patients. The agents can use learning principles such as reinforcement provide tools for overcoming barriers to compliance with dietary therapy and/or increased physical activity to help patient in achieving weight loss and weight maintenance. Specific communication message include self-monitoring of both eating habits and physical activity, stress management, stimulus control, problem solving, contingency management, cognitive restructuring, and social support through the social network system.

Pharmacotherapy can be used if behavior therapy does not work. In carefully selected patients, appropriate drugs can augment LCDs, physical activity, and behavior therapy in weight loss. Drugs such as sibutramine and orlistat can be used as long as potential side effects with drugs are considered. With sibutramine, increases in blood pressure and heart rate may occur. Sibutramine should not be used in patients with a history of hypertension, CHD, congestive heart failure, arrhythmias, or history of stroke. With orlistat, fat soluble vitamins may require replacement because of partial malabsorption. Weight loss surgery is one option for weight reduction in a limited number of patients with clinically severe obesity, i.e., BMIs>=40 or >=35 with comorbid conditions. Weight loss surgery should be reserved for patients in whom efforts at medical therapy have failed and who are suffering from the complications of extreme obesity. Gastrointestinal surgery (gastric restriction [vertical gastric banding] or gastric bypass is an intervention weight loss option for motivated subjects with acceptable operative risks. An integrated program must be in place to provide guidance on diet, physical activity, and behavioral and social support both prior to and after the surgery.

The agents are adaptive to the patient and allow for program modifications based on patient responses and preferences. For example, the agent can be modified for weight reduction after age 65 to address risks associated with obesity treatment that are unique to older adults or those who smoke.

The event handler can be coded to:
Receive message from patient or doctor (20)
Determine user treatment modality (22)
For each modality
Determine relevant rules (26)
For each rule
Determine responsive agent(s) (30)
For each agent
Execute agent program (34)
Get input from service provider if needed (36)
Format & send the message for the patient's mobile device (38)

The system processes a communication from a patient according to one or more treatment scenarios. Each treatment scenario is composed of one or more rules to be processed in a sequence that can be altered when invoking certain agents.

The if then rules can be described to the system using a graphical user interface that runs on a web site, a computer, or a mobile device, and the resulting rules are then processed by a rules engine. In one embodiment, the if then rules are entered as a series of dropdown selectors whose possible values are automatically determined and populated for user selection to assist user in accurately specifying the rules.

In one embodiment, the rules engine is Jess, which is a rule engine and scripting environment written entirely in Sun's Java language by Ernest Friedman-Hill at Sandia National Laboratories in Livermore, Calif. With Jess, the system can "reason" using knowledge supplied in the form of declarative rules. Jess is small, light, and one of the fastest rule engines available. Jess uses an enhanced version of the Rete algorithm to process rules. Rete is a very efficient mechanism for solving the difficult many-to-many matching problem (see for example "Rete: A Fast Algorithm for the Many Pattern/Many Object Pattern Match Problem", Charles L. Forgy, Artificial Intelligence 19 (1982), 17-37.) Jess has many unique features including backwards chaining and working memory queries, and of course Jess can directly manipulate and reason about Java objects. Jess is also a powerful Java scripting environment, from which you can create Java objects, call Java methods, and implement Java interfaces without compiling any Java code.

The user can dynamically create an if/then/else statement. A dropdown selector can be used to select a column, then a dropdown to select the conditional operator (=, >, <, !=, among others) and then a text box in which to enter a column, text or number value. The system can add multiple conditions. The rules can be saved as serialized object in a database. After entering parameter values, a new set of rules can be generated and inserted within the current active scenario. The corresponding rules can then be modified directly by accessing the individual agents within the rules.

In one embodiment, the agent can be self-modifying. The agent receives parameters from its callers. The agent in turn executes one or more functions. It can include an adaptive self-modifying function, and the third-party extension interfaces. The adaptive self-modifying function is capable of modifying the agent parameters and/or the agent function at run time, thereby changing the behavior of the agent.

An exemplary modality of the rules engine can be used to serve obese patients that the doctor can review and approve. In this scenario, the engine executes 3 master agents: blood pressure master agent (50), diabetic master agent (52), and weight loss agent (54). The blood pressure master agent in turn invokes the following agents:
  If blood pressure is between 130-139/85-89 mm Hg then run agent high_blood_pressure
  If blood pressure is between 140-159/90-99 mm Hg then run agent stage 1_blood_pressure
  If blood pressure is above 159/99 mm Hg then run agent drug_treatment_for_blood_pressure For the above example, high normal blood pressure of between 130-139/85-89 mm Hg is included in the risk stratification. In patients with high normal blood pressure with no or only one concurrent risk factor that does not include diabetes, target organ, or clinical cardiac disease, the agent high_blood_pressure suggests to the patient to use lifestyle modification to lower blood pressure. Lifestyle modification includes changes to the patient's dieting and exercising habits. With a risk factor of target organ or clinical cardiac disease, diabetes and/or other risk factors, the agent can recommend drug therapy, no matter what the patient's blood pressure is. The agent for patients with stage 1 blood pressures of between 140-159/90-99 mm Hg who have no other risk factors will suggest the patient try lifestyle modifications for a year before drug therapy is used. But if these patients have one risk factor other than diabetes, target organ, or clinical cardiac disease, their lifestyle modification should be tried for only 6 months before initiation therapy. For patients with blood pressure above 150/100 mm Hg, the agent reminds the patient to have drug therapy in addition to lifestyle modifications.

The diabetic master agent in turn invokes the following agents:
  Monitoring agent: Make sure doctor orders the key tests at the right times.
  Dieting planning agent: Work with a dietitian to develop a great eating plan.
  Glucose Testing Agent: Check blood glucose at correct intervals.
  Exercise agent: Monitor exercise to help heart.
  Medication compliance agent: check that insulin is taken at correct time.
  Foot care agent: Check your feet with your eyes daily.
  Eye care agent: remind patient to get periodic eye exam.

The weight loss agent considers the patient's BMI, waist circumference, and overall risk status including the patient's motivation to lose weight. The weight loss agent in turn call the following agents:
  Body Mass Index agent: The BMI, which describes relative weight for height, is significantly correlated with total body fat content. The BMI should be used to assess overweight and obesity and to monitor changes in body weight. In addition, measurements of body weight alone can be used to determine efficacy of weight loss therapy. BMI is calculated as weight (kg)/height squared (m2). To estimate BMI using pounds and inches, use: [weight (pounds)/height (inches)2]×703. Weight classifications by BMI, selected for use in this report, are shown below:

| CLASSIFICATION OF OVERWEIGHT AND OBESITY BY BMI | | |
|---|---|---|
| | Obesity Class | BMI (kg/m$^2$) |
| Underweight | | <18.5 |
| Normal | | 18.5-24.9 |
| Overweight | | 25.0-29.9 |
| Obesity | I | 30.0-34.9 |
| | II | 35.0-39.9 |
| Extreme Obesity | III | ≥40 |

A conversion table of heights and weights resulting in selected BMI units is

| SELECTED BMI UNITS CATEGORIZED BY INCHES (CM) AND POUNDS (KG). | | | |
|---|---|---|---|
| Height in inches (cm) | BMI 25 kg/m$^2$ | BMI 27 kg/m$^2$ | BMI 30 kg/m$^2$ |
| | Body weight in pounds (kg) | | |
| 58 (147.32) | 119 (53.98) | 129 (58.51) | 143 (64.86) |
| 59 (149.86) | 124 (56.25) | 133 (60.33) | 148 (67.13) |
| 60 (152.40) | 128 (58.06) | 138 (62.60) | 153 (69.40) |
| 61 (154.94) | 132 (59.87) | 143 (64.86) | 158 (71.67) |
| 62 (157.48) | 136 (61.69) | 147 (66.68) | 164 (74.39) |
| 63 (160.02) | 141 (63.96) | 152 (68.95) | 169 (76.66) |
| 64 (162.56) | 145 (65.77) | 157 (71.22) | 174 (78.93) |
| 65 (165.10) | 150 (68.04) | 162 (73.48) | 180 (81.65) |
| 66 (167.54) | 155 (70.31) | 167 (75.75) | 186 (84.37) |
| 67 (170.18) | 159 (72.12) | 172 (78.02) | 191 (86.64) |
| 68 (172.72) | 164 (74.39) | 177 (80.29) | 197 (89.36) |
| 69 (175.26) | 169 (76.66) | 182 (82.56) | 203 (92.08) |
| 70 (177.80) | 174 (78.93) | 188 (85.28) | 207 (93.90) |
| 71 (180.34) | 179 (81.19) | 193 (87.54) | 215 (97.52) |
| 72 (182.88) | 184 (83.46) | 199 (90.27) | 221 (100.25) |
| 73 (185.42) | 189 (85.73) | 204 (92.53) | 227 (102.97) |
| 74 (187.96) | 194 (88.00) | 210 (95.26) | 233 (105.69) |

SELECTED BMI UNITS CATEGORIZED
BY INCHES (CM) AND POUNDS (KG).

| | | | |
|---|---|---|---|
| 75 (190.50) | 200 (90.72) | 216 (97.98) | 240 (108.86) |
| 76 (193.04) | 205 (92.99) | 221 (100.25) | 246 (111.59) |

| | |
|---|---|
| Metric conversion formula = weight (kg)/height (m)$^2$ | Non-metric conversion = [weight (pounds)/height (inches)$^2$] × 704.5 |
| Example of BMI calculation: A person who weighs 78.93 kilograms and is 177 centimeters tall has a BMI of 25: weight (76.93 kg)/ height (177 m)$^2$ = 25 | Example of BMI calculation: A person who weighs 164 pounds and is 68 inches (or 5'8") tall has a BMI of 25: (weight (164 pounds)/height (68 inches)) × 704.5 = 25 |

Waist Circumference agent: The presence of excess fat in the abdomen out of proportion to total body fat is an independent predictor of risk factors and morbidity. Waist circumference is positively correlated with abdominal fat content. It provides a clinically acceptable measurement for assessing a patient's abdominal fat content before and during weight loss treatment. The sex-specific cutoffs noted on the next page can be used to identify increased relative risk for the development of obesity-associated risk factors in most adults with a BMI of 25 to 34.9 kg/m2: These waist circumference cutpoints lose their incremental predictive power in patients with a BMI>=35 kg/m2 because these patients will exceed the cutpoints noted above. The disease risk of increased abdominal fat to the disease risk of BMI is as follows:

CLASSIFICATION OF OVERWEIGHT AND OBESITY BY BMI,
WAIST CIRCUMFERENCE AND ASSOCIATED DISEASE RISKS

| | | | Disease Risk* Relative to Normal Weight and Waist Circumference | |
|---|---|---|---|---|
| | BMI (kg/m$^2$) | Obesity Class | Men ≤102 cm (≤40 in) Women ≤88 cm (≤35 in) | >102 cm (>40 in) >88 cm (>35 in) |
| Underweight | <18.5 | | — | — |
| Normal | 18.5-24.8 | | — | — |
| Overweight | 25.0-29.9 | | Increased | High |
| Obesity | 30.0-34.9 | I | High | Very High |
| | 35.0-39.9 | II | Very High | Very High |
| Extreme Obesity | ≥40 | III | Extremely High | Extremely High |

These categories denote relative risk, not absolute risk; that is, relative to risk at normal weight. They should not be equated with absolute risk, which is determined by a summation of risk factors. They relate to the need to institute weight loss therapy and do not directly define the required intensity of modification of risk factors associated with obesity.

Risk Status agent is used for assessment of a patient's absolute risk status and in turn uses the following agents:

Disease condition agent: determine existence of coronary heart disease (CHD), other atherosclerotic diseases, type 2 diabetes, and sleep apnea.

Obesity-associated disease agent: determines gynecological abnormalities, osteoarthritis, gallstones and their complications, and stress incontinence.

Cardiovascular risk factors agent: cigarette smoking, hypertension (systolic blood pressure >=140 mm Hg or diastolic blood pressure >=90 mm Hg, or the patient is taking antihypertensive agents), high-risk LDL-cholesterol (>=160 mg/dL), low HDL-cholesterol (<35 mg/dL), impaired fasting glucose (fasting plasma glucose of 110 to 125 mg/dL), family history of premature CHD (definite myocardial infarction or sudden death at or before 55 years of age in father or other male first-degree relative, or at or before 65 years of age in mother or other female first-degree relative), and age (men >=45 years and women >=55 years or postmenopausal). Patients can be classified as being at high absolute risk if they have three of the aforementioned risk factors. Patients at high absolute risk usually require clinical management of risk factors to reduce risk. Patients who are overweight or obese often have other cardiovascular risk factors. Methods for estimating absolute risk status for developing cardiovascular disease based on these risk factors are described in detail in the National Cholesterol Education Program's Second Report of the Expert Panel on the Detection, Evaluation, and Treatment of High Blood Cholesterol in Adults (NCEP's ATP II) and the Sixth Report of the Joint National Committee on Prevention, Detection, Evaluation, and Treatment of High Blood Pressure (JNC VI). The intensity of intervention for cholesterol disorders or hypertension is adjusted according to the absolute risk status estimated from multiple risk correlates. These include both the risk factors listed above and evidence of end-organ damage present in hypertensive patients. Approaches to therapy for cholesterol disorders and hypertension are described in ATP II and JNC VI, respectively. In overweight patients, control of cardiovascular risk factors deserves equal emphasis as weight reduction therapy. Reduction of risk factors will reduce the risk for cardiovascular disease whether or not efforts at weight loss are successful.

Other risk factors can be considered as rules by the agent, including physical inactivity and high serum triglycerides (>200 mg/dL). When these factors are present, patients can be considered to have incremental absolute risk above that estimated from the preceding risk factors. Quantitative risk contribution is not available for these risk factors, but their presence heightens the need for weight reduction in obese persons.

One embodiment determines high interest disease- and drug-related variants in the patent's genome and identifies top diseases with the highest probabilities. For each disease, the system determines the pretest probability according to the patient age, gender, and ethnicity. The system then determines the independent disease-associated SNVs used to calculate the subject's disease probability. For each disease, for example type 2 diabetes, the system determines probability using independent SNVs, a likelihood ratio (LR), number of studies, cohort sizes, and the posttest probability. Blood pressure and blood glucose trend measurements are also determined.

A patient motivation agent evaluates the following factors: reasons and motivation for weight reduction; previous history of successful and unsuccessful weight loss attempts; family, friends, and work-site support; the patient's understanding of the causes of obesity and how obesity contributes to several diseases; attitude toward physical activity; capacity to engage in physical activity; time availability for weight loss intervention; and financial considerations. In addition to considering these issues, the system can heighten a patient's motivation for weight loss and prepare the patient for treatment through normative messaging and warnings. This can be done by enumerating the dangers accompanying persistent obesity and by describing the strategy for clinically assisted weight reduction. Reviewing the patients' past attempts at weight loss and explaining how the new treatment plan will be different can encourage patients and provide hope for successful weight loss.

In an exemplary system for providing precision medicine, historical data from a large population is received and provided to a learning engine. The learning engine clusters the population into groups of similar characteristics and then creates a social network of patients who share enough health/medical similarity that they are apt to share many medical issues. Thus a user's likelihood of contracting a disease might be evaluated by knowing the disease status of other users in the same influence cluster or neighborhood, whether they are closely connected to that user or not.

The system, generally denoted by reference numeral 100, comprises one or more central processing units CP1 . . . CPn, generally denoted by reference numeral 110. Embodiments comprising multiple processing units 110 are preferably provided with a load balancing unit 115 that balances processing load among the multiple processing units 110. The multiple processing units 110 may be implemented as separate processor components or as physical processor cores or virtual processors within a single component case. In a typical implementation the computer architecture 100 comprises a network interface 120 for communicating with various data networks, which are generally denoted by reference sign DN. The data networks DN may include local-area networks, such as an Ethernet network, and/or wide-area networks, such as the internet. In some implementations the computer architecture may comprise a wireless network interface, generally denoted by reference numeral 125. By means of the wireless network interface, the computer 100 may communicate with various access networks AN, such as cellular networks or Wireless Local-Area Networks (WLAN). Other forms of wireless communications include short-range wireless techniques, such as Bluetooth and various "Bee" interfaces, such as XBee, ZigBee or one of their proprietary implementations. Depending on implementation, a user interface 140 may comprise local input-output circuitry for a local user interface, such as a keyboard, mouse and display (not shown). The computer architecture also comprises memory 150 for storing program instructions, operating parameters and variables. Reference numeral 160 denotes a program suite for the server computer 100. Reference number 115-135 denotes an optional interface by which the computer obtains data from external sensors, analysis equipment or the like.

In some embodiments the data processing system is coupled with equipment that determines an organism's genotype from an in-vitro sample obtained from the organism. In other embodiments the genotypes are determined elsewhere and the data processing system may obtain data representative of the genotype via any of its data interfaces.

One exemplary sensor communicating with one of the interfaces 115-135 receives a biologic sample from an individual such as a bodily fluid (such as urine, saliva, plasma, or serum) or feces or a tissue sample (such as a buccal tissue sample or buccal cell). The biologic sample can then be used to perform a genome scan. For example, DNA arrays can be used to analyze at least a portion of the genomic sequence of the individual. Exemplary DNA arrays include GeneChip® Arrays, GenFlex® Tag arrays, and Genome-Wide Human SNP Array 6.0 (available from Affymetrix, Santa Clara, Calif.). In other examples, DNA sequencing with commercially available next generation sequencing (NGS) platforms is generally conducted: DNA sequencing libraries are generated by clonal amplification by PCR in vitro; then the DNA is sequenced by synthesis, such that the DNA sequence is determined by the addition of nucleotides to the complementary strand rather through chain-termination chemistry; next, the spatially segregated, amplified DNA templates are sequenced simultaneously in a massively parallel fashion without the requirement for a physical separation step. For microbiome analysis, cotton swabs are applied to forehead, behind ears, nose, among others, and fecal samples are analyzed using DNA sequencing machines. In certain embodiments, whole or partial genome sequence information is used to perform the genome scans. Such sequences can be determined using standard sequencing methods including chain-termination (Sanger dideoxynucleotide), dye-terminator sequencing, and SOLiD™ sequencing (Applied Biosystems). Whole genome sequences can be cut by restriction enzymes or sheared (mechanically) into shorter fragments for sequencing. DNA sequences can also be amplified using known methods such as PCR and vector-based cloning methods (e.g., *Escherichia coli*).

In some embodiments, at least a portion of an individual's genetic material (e.g., DNA, RNA, mRNA, cDNA, other nucleotide bases or derivative thereof) is scanned or sequenced using, e.g., conventional DNA sequencers or chip-based technologies, to identify the presence or absence of one or more SNPs or CNPs or copy number polymorphisms ("CNPs") and their corresponding alleles.

One embodiment performs exome sequencing (also known as Whole Exome Sequencing or WES), which is a technique for sequencing all the protein-coding genes in a genome (known as the exome). It consists of first selecting only the subset of DNA that encodes proteins (known as exons), and then sequencing that DNA using any high throughput DNA sequencing technology. There are 180,000 exons, which constitute about 1% of the human genome, or approximately 30 million base pairs. Exome data relates with genetic variation that is responsible for both Mendelian and common diseases such as Miller syndrome and Alzheimer's disease without the high costs associated with whole-genome sequencing.

The sensors connecting to interfaces 115-135 can also include fitness sensors such as wearable watches/clothing/shoes that monitor activity, heart rate, ECG, blood pressure, blood oxygen level, among others. The sensors 115-135 can also detect purchase activities and on-line activities that reflect the user's health habits. For example, the sensors can be a data feed that picks up data relating to grocery purchases, food expenses, restaurant spending.

In yet other examples, the sensors connecting to interfaces 115-135 can be sensors in a phone. For example, in depression sensor, the phone can detect a person's activity and correlate to depression: people who stuck to a regular pattern of movement tended to be less depressed as people with mental health problems in general have disrupted circadian rhythms and a depressed mood may pull a user off her routine. Depressed people also spends more time on their phones or browsing aimlessly, as depressed people tend to start avoiding tasks or things they have to do, particularly when they're uncertain.

In addition to sensor captured healthcare data, healthcare data refers to any data related or relevant to a patient. Healthcare data may include, but is not limited to, fitness data and healthcare-related financial data. Clinical data, as used herein, refers to any healthcare or medical data particular to a patient. In embodiments, clinical data can be medical care or healthcare data resulting from or associated with a health or medical service performed in association with a clinician in a healthcare environment (e.g., lab test, diagnostic test, clinical encounter, ecare, evisit, etc.). Clinical data may include, but is not limited to, a health history of a patient, a diagnosis, a clinician assessment, clinician narrative, a treatment, a family history (including family health history and/or family genetics), an immunization record, a medication, age, gender, date of birth, laboratory values, diagnostics, a test result, an allergy, a reaction, a procedure performed, a social history, an advanced directive, frequency and/or history of healthcare facility visits, current healthcare providers and/or current healthcare provider location, preferred pharmacy, prescription benefit management data, an alert, claims data, a vital, data traditionally captured at the point of care or during the care process, a combination thereof, and the like. In the same or alternative embodiments, the clinical data may include medical compliance information. In certain embodiments, medical compliance information refers to a level of compliance of a particular patient with one or more prescribed medical treatments, such as medications, diet, physical therapy, follow up healthcare visits, and the like. In one or more embodiments, the clinical data may include data obtained from the natural language processing of one or more clinical assessments and/or clinical narratives.

In certain embodiments, healthcare-related financial data can refer to any financial information relevant to a patient, such as insurance data, claims data, payer data, etc. Such healthcare data (e.g., clinical data and healthcare-related financial data) may be submitted by a patient, a care provider, a payer, etc. In certain embodiments where the healthcare data is being submitted by anyone other than the patient, the patient may be required to approve of such submission and/or may opt-in to or opt-out of having such healthcare data being submitted.

One embodiment uses local storage on the mobile phone of data collected by other devices and an app is provided to interpret sensor data. The phones have fingerprint sensor security, and the mobile app is the point of aggregation for all the user's different health data. The health data is captured by the footwear and also by third party sensors (Nike+®, Withings Scale, Fitbit Flex® etc) and the data from all fitness hardware into a cohesive whole.

In one embodiment, sensors in the clothing or shoes or worn by the user can communicate with a mobile phone and transmit user activity or inactivity to networks that allow information access and provide support on the back end. Having a network or backbone that a much broader population base can seamlessly connect to will fuel more meaningful data comparisons and analysis and distill useful information. The network can then aggregate data from the footwear with other health information—data from across a certain geography or specific diagnosis, for example—to create a more complete picture of group health.

Creating healthcare communities from which to collect data is a way to crowd source valuable healthcare information. By bringing together people with a common interest such as weight loss, the footwear devices serve as a mechanism to build engagement and at the same time compile information. In one embodiment, the information is used by health payors or insurers to prompt patients to change their lifestyles. The more employers, insurance companies, or healthcare payors know about a population's health, the more steps they can take to keep them healthy. For instance, patient data entered into electronic health records at practices and hospitals could reveal allergies, health histories, and medication use. Combined with information collected through the footwear, providers will have more complete and essentially real-time data to treat and manage the health of individual patients, as well as patient populations. The cumulative sum of data captured from many individuals about a health condition or population can be used to move the population to healthier conditions. In one embodiment, health plans can offer incentives to members willing to sign up for designated footwear health programs and join in a "game" to be fit.

The system reduces healthcare costs by identifying trends and commonalities among certain populations—thereby enabling better preventive care. In addition to engaging patients and aiding personal wellness, they can move healthcare beyond individual monitoring and treatment toward more effective population health management.

By engaging and empowering patients to take an active role in data collection, the footwear applies inconspicuous foot data with analytics to improve health. One embodiment uses Google Maps to display health activity traffic; showing healthcare patterns based on real time reporting of anonymous data from healthcare footware devices. Healthcare organizations can tap the power of that data to engage patients and develop more effective and more personalized approaches to care, thereby lowering the overall cost of care.

The system identifies pre-detectable characteristics of a health condition, such that future incidents of the health condition may be predicted, i.e., before the health condition occurs for disease prevention. One implementation includes capturing data from mobile fitness devices and establishing a plurality of health related characteristics associated with the population including walking status, weight, calorie burn. The characteristics include a plurality of pre-detectable characteristics with a relationship between the health related characteristics and at least one health condition, and analyzing at least a portion of said population in response to the relationship.

Another embodiment includes establishing at least one pre-detectable characteristic associated with a health condition, applying an intervention in response to the characteristic, monitoring a success characteristic of the intervention, and determining a cause of the success characteristic.

Another embodiment builds a repository of health related characteristics associated with the population, the characteristics including a plurality of pre-detectable characteristics; and a processor configured to receive the health related characteristics, establish a relationship between the health related characteristics and at least one health condition, and analyzing at least a portion of the population in response to said relationship.

A population, as used herein, is any group of members. The population may include a high level of members, for example a group including one or more of the five kingdoms of living things, or a subgroup, for example a group including humans of a certain age range. The population may include living and/or dead members. The analysis may include predicting a likelihood of a member developing the health condition, in response to the relationship. The health condition may be any type of physical or mental health condition, disease, and/or ailment. In addition, the analysis may include predicting the incidence of the health condition. The analysis may also include performing a simple yes/no prediction regarding whether a member will likely develop the health condition. The analysis may be used to enable the management of a health care program, such as a program associated with a corporation, or a program offered to the public by a health care consultant or provider. If the analysis is associated with a corporation's healthcare program, the population may include some or all of the employees and retirees of the corporation, and associated spouses and dependents. The population may include other associated groups of the corporation, such as consultants, contractors, suppliers and/or dealers. The population may include participants from multiple corporations and/or the general public. If the health care program is offered to the public, the population may include members of the public, organizations, and/or corporations.

The health related characteristics may include a plurality of health characteristics, lifestyle characteristics and/or family health characteristics associated with the members of the population. Health characteristics may include characteristics indicative of a specific member's health. For example, lifestyle characteristic may include weight, heart rate, walking gait, sitting gait, running gait, exercise or activity as detected by accelerometers, diet, and other factors detectable by fitness devices such as watches, phones, or foot sensors detailed above. For other example, health characteristic may include medical characteristics (e.g., what medical visits, processes, procedures, or test have been performed associated with the member, the number of days the member has spent in a medical facility (e.g., a hospital), the number of visits the person has made to a doctor, etc.), drug characteristics (e.g., what type and amount of drugs are being consumed), a death characteristic (e.g., information associated with a death certificate), an absenteeism characteristic, disability characteristics, characteristics associated with existing health conditions, etc. Family health characteristics associated with the member may include information associated with the family medical history of a specific member. For example, a history of a particular health risk within the family, e.g., heart failure, cancer, high blood pressure, diabetes, anxiety, stress, etc. Lifestyle characteristic may include a specific member's behavior characteristic(s), of which some or all may be modifiable lifestyle characteristics. A modifiable lifestyle characteristic may include an exercise characteristic (e.g., does the member exercise, how often, what is the exercise, etc.) and/or a nutrition characteristic (e.g., what types of food does the member eat, and how often). Nutrition characteristics may also include the amount of salt consumed during a designated period (e.g., a day), and the amount of fat and/or saturated fat consumed during a designated period. In addition, modifiable lifestyle characteristics may include whether the member drinks alcohol (and if so how much), a drug intake characteristic, (i.e., does the member take drugs, and if so how often, what kind, and how much), a weight characteristic (e.g., what does the member weigh, what is the member's desired weight, is the member on a diet, what is the member's weight indicator e.g., obese, slightly overweight, underweight, normal, etc.), a smoking characteristic (does the member smoke and if so how much), a safety characteristic (what are the member's driving characteristics e.g., does the member where seat belts, have one or more infractions associated with driving under the influence, or speeding tickets, etc.). In addition, modifiable lifestyle characteristics may include a hypertension characteristic, a stress characteristic, a self-care characteristic, a self-efficacy characteristic, a readiness to change characteristics, and a prophylactic aspirin therapy characteristic.

In one embodiment, the health related characteristics may also include one or more of the following: demographic characteristics, the member's location or geography, age, gender, employment status, employment type, and/or work characteristics of the member. The health-related characteristics may be obtained through one or more of several sources, such as medical claims, drug claims, and/or self-reported characteristics (or data). In one embodiment, self-reported characteristics may be collected from the population. The amount and type of self-reported characteristics collected associated with the population is implementation dependent and may vary based upon the participation of the population, the relevance of the information to the different members of the population, and the analysis to be performed. Therefore the self-reported characteristics established may be associated with a subset, or portion, of the established population, or the entire population. The self-reported characteristics may include one or more health characteristics, family health characteristics, and lifestyle characteristics associated with a member of the population. The self-reported characteristics, also referred to as self-assessments, may be obtained through the use of one or more health related questionnaires submitted to the member. Examples of questionnaires include physical questionnaires, electronic questionnaires (e.g., located on a health related web-site), questionnaires filled out during a phone or personal interview, etc. The responses to the questionnaires may include a member's self assessed health related characteristics. The characteristics may include a self-efficacy characteristic and/or a readiness to change characteristic. A readiness to change characteristic is a characteristic indicative of a members readiness to change one or more behaviors, activities, or characteristics. A self-efficacy characteristic, as will be discussed, includes an indication of a member's belief in their ability to succeed in changing a lifestyle characteristic. For example the self-assessment questionnaire may specifically ask the member: does the member believe they can change their lifestyle or a specific aspect of their lifestyle, is the member willing to attempt to change an aspect of their lifestyle and if so, how successful do they think they will be, how important do they think it is to change one or more specified lifestyles, etc. Alternatively, one or more questions may be asked of which the answers may provide indirect indicators of whether the person actually does believe they can change aspects of their lifestyle, and also whether the member is actually ready to change a particular aspect of their lifestyle.

In one embodiment, the health related characteristics of the population are associated with self-reported biometric characteristics. For example, the sources of the health related characteristics may be self-reported biometric sources. That is, the sources of the health related characteristics are sources other than the direct physical examination of a member (e.g., where members provide a biological sample etc). The distinction is based on the issue that due to the size of the population, it may not be possible to analyze all of the members by having detailed examinations (e.g., blood samples, urine samples, etc.) of all, or even a substantial portion of the population. Therefore, in one embodiment, the health analysis is based on information that is obtained second-hand, without having physically examined a specific member to directly obtain the desired health related characteristics. Of course, if the described analysis indicates a particular member needs to be physically examined based on likelihood of occurrence of a health condition, which examination may occur. In one embodiment, the health related characteristics may relate to non-intrusive characteristics, i.e., characteristics that do not directly involve the physical examination or taking of biological samples of a member by a physician. For example, a blood sample may be considered intrusive data because it involves the taking of a sample from a member.

The collected health related characteristics may be stored in a repository. The duration of storage is implementation dependent, but in general the more information available for analysis, the more accurate the results will be. Therefore, a historical repository of five to ten years may be established. In some embodiments, characteristics may be available throughout the working career of the members, e.g., if their employer collects self-reported information, medical and/or drug claims. The historical repository aids analysis in several ways, including reducing the impact of recall bias. Recall bias is what may happen when a member acquires a particular health condition, and then attempts to recall what factors may have contributed to the condition. The members recollection may be biased by any number of issues including their ability to accurately remember all the desired information. Therefore a historical repository aids in providing accurate information for analysis.

The established health related characteristics may be used to analyze the health of the population. In one embodiment, as illustrated in a second control block 104, a prevalence of a health condition within the population may be established. The prevalence of a condition may be described as the current existence of a condition. The prevalence of a health condition among a population may be described as the number or percentage of members that have a specific health condition. Establishing the prevalence of a condition in a population may include determining which members currently have a specific health condition. The prevalence of a health condition may be established by analyzing the health related characteristics associated with one or more members of the population and responsively establishing whether one or more members has the condition. For example, the prevalence may be established by analyzing information associated with medical claims and/or drug claims associated with the population.

Medical claims may include any type of health related correspondence between a health analyst or provider (e.g., doctor, physician, medical laboratory, hospital, medical support group such as x-ray providers, etc.), and a member of the population and/or a health care insurer, provider, or manager, for the member (e.g., corporation (employer) or third party insurer/manager, etc.). In one embodiment, the healthrelated correspondence may include health codes such as E/M (Evaluation and Management) codes, Current Procedural Terminology (CPT) codes, and International Classification of Diseases (ICD) codes. ICD codes provide coded information associated with the treatment, health, and/or a condition of a member. These codes may include information associated with the professional services performed, the specific procedure(s) performed, and why the procedure(s) was performed. Therefore, analysis of ICD, CPT, and/or E/M codes may be used to establish whether a member has a particular health condition.

A drug claim may include any type of medication related correspondence between a medication provider (e.g., doctor, pharmacist, etc.), and a member of the population and/or a health care insurer, provider, or manager for the member (e.g., corporation (employer) or third party insurer/manager, etc.). In one embodiment, the correspondence may include codes or identification systems such as Group Product Index (GPI). The GPI provides a numbering system associated with the medication a member receives, and/or medication prescribed for a member. The GPI enables the identification of the type of drug, manufacturer, strength, associated dosage, and associated medication form (e.g., pill, tablet, liquid, etc.).

In one embodiment, information associated with at least one medical and/or drug claim may be used to determine the prevalence of a condition, e.g., whether a member has one or more specific health conditions. For example, if a medical claim indicates a particular procedure has been performed, then that procedure may be correlated to one or more potential health conditions associated with that procedure. Analogously, if a drug claim indicates that a member is being prescribed and/or receiving a particular medication, then that medication may be correlated to one or more potential health conditions associated with that medication. In this manner, the information associated with the medical and/or drug claims may be analyzed to establish a prevalence of a condition. The analysis may be performed on each member of the population, or a subset thereof.

In one embodiment, information associated with multiple medical and/or drug claims may be analyzed based on established criteria, to establish the prevalence of a health condition. For example, multiple medical and/or drug claims may be cross checked with each other to establish the prevalence of a health condition. An individual medical or drug claim may contain erroneous or misleading information. For example, there may be instances where a medical procedure is performed to test for a health condition, without definitively establishing the condition exists in the member. Analysis of the resulting medical claim may lead someone to erroneously believe the person had the health condition (e.g., based on the types of procedures being performed). Therefore, using one medical or drug claim may not provide an accurate indication of the presence of a health condition. Additional medical claims and/or drug claims may be analyzed to establish one or more healthrelated characteristics of a member, such as the prevalence of a health condition. In one embodiment, multiple medical and/or drug claims, separated by a time period (e.g., a minimum duration) may be analyzed. The separation in time increases the confidence level regarding the determination that a particular health claim, or health related characteristic, exists. For example, two claims of the same type (e.g., two medical claims or two drug claims), separated in time by at least three months, may be analyzed to determine if a member has a health condition. If the first claim indicates a condition exists, and a second claim indicates the same condition exists, then the member may be assumed to have the condition associated with the medical claims. The two claims may sequentially occur, or be separated by one or more other medical and/or drug claims. In addition, a claim of one type (e.g., medical claim) may be cross checked with a claim of another type (e.g., drug claim). If the two claims correlate, then the member may be considered to have the particular condition. The two different types of claims may also be separated by a designated time period, e.g., three months, to further establish that the condition actually exists. In one embodiment, the time separation is established such that the two claims represent independent indicators, as opposed to two claims associated with the same medical event (medical checkup or medication collection). Additional criteria may include that the claims being correlated should occur within a particular time period of each other. For example, if two claims indicating a particular health condition are separated by five years in time, there is a chance that the claims were inaccurate anomalies as opposed to indications of the existence of the health condition. Therefore, a maximum duration between claims being cross checked may be established (e.g., one year). In one embodiment, the maximum duration between cross checked claims may be dependent upon the condition at issue. For example, some health conditions may be more likely to have multiple claims occur within a specific time duration. While other health conditions may not manifest themselves in multiple medical claims in that same specified time duration. Therefore, the duration between claims may be implementation and health condition dependent.

When claims are received, they may be manually or automatically analyzed. For example, when a claim is received, it may be analyzed to establish associated health characteristics. The health characteristics may then be cross checked with information from other claims in an attempt to verify one or more of the health characteristics. The analysis may include correlating the claim with a table of potential health characteristics associated with claim information. The information may be compared with previous claim information to determine if prior claims indicated the same, or similar health related characteristics. If the cross check indicates one or more prior claims indicated the same health related characteristic, then the member may be assumed to have the health related characteristic (e.g., the health condition). If no prior claim information correlates with the current claim information, then the current claim information, and the correlated health related characteristics may be store to be compared with future claims that are to be receive. In one embodiment, if a strong correlation exists between the health related characteristics associated with multiple claims, and a sufficient time period exists between the claims, then the member may be determined to have the characteristics. Alternatively, machine learning such as classical, Bayesian, and/or statistical analysis techniques may be used to correlate and cross check one or more medical and/or drug claims with one or more health related characteristics and/or health conditions. For example, neural networks may be trained to associate information associated with medical and/or drug claims with particular health related characteristics and/or health condition. Then when a claim is received, it may be analyzed to establish potential health related characteristics and/or health conditions. The neural network may be able to provide a weighted analysis such that the results have an associated confidence factor. If multiple claims separated in time indicate the same or similar health related characteristics, the resulting neural network analysis may provide a higher confidence indicator than if just one claim indicated the characteristics. Therefore, as prevalent health conditions are established based on medical and/or drug claims, the claims may be further analyzed to establish a relationship capable of automatically detecting a prevalence based on the available medical and/or drug claims.

In one embodiment, the medical and/or drug claims may be analyzed as they are received. Alternatively, there may be a repository of one or more previous medical and/or drug claims associated with the member(s). For example, repositories may be created that include a members historical health related characteristics over a time period (e.g., the last five-ten years). These repositories may be maintained by the health care provider, insurer, analyzer, and/or manager. These repositories may be analyzed to establish a prevalence of a condition among the population.

In one embodiment, self-reported characteristics may be analyzed to establish the prevalence of a condition, e.g., among one or more members of a population and/or the population as a whole. For example, a member may specifically indicate that they have a particular condition such as high blood pressure, diabetes, smoking, overweight, among others. Alternatively the analysis of one or more of the family history, lifestyle, or health characteristics indicated through the self assessments may indicate that the member likely has a particular condition. In this case additional follow-up may be performed with the member to determine if they actually have the condition, or know that they have the condition. In one embodiment, a relationship may be established to determine the existence of a condition among a particular member and/or among the population.

In one embodiment, medical claims, drug claims, and self-reported characteristics may be used to establish the prevalence of a particular condition among the population. Alternatively, as indicated above, the prevalence of a condition may be established based on one or more of the sources of information (e.g., medical claims, drug claims, and/or self-reported characteristics). The prevalence may be established manually or through an automated process such as the use of statistical analysis techniques as mentioned above. The decision of what information (or sources of information) to use may be based on what information is available for the population, or for a particular portion of the population. For example, some portions of the population may not have a historical data base of information available for analysis. In addition, some portions of the population may not have associated medical claims, drug claims and/or self-reported characteristics. Therefore the type and amount of information to be analyzed to establish the prevalence of a disease is implementation dependent and may be based in part on the type of information available for a particular population, or portion thereof.

A relationship may be established between the health related characteristics and one or more health conditions. In one embodiment, the relationship is established in response to the prevalence of the health condition. The relationship may then be modified based on future occurrences, or rates of occurrences of the condition. Alternatively, the relationship may be established by analyzing future occurrences or rates of occurrence of the condition without accounting for an initial prevalence of the condition. In one embodiment, as described below, the relationship may be used to predict an incident or occurrence of a disease, e.g., an occurrence of a disease among a particular member or among a population in general. Information gained from establishing the prevalence of the condition may be used to establish the relationship. For example, the health related characteristics associated with the members determined to have a particular condition may be analyzed to establish a relationship associated with a likelihood of developing the condition. In one embodiment, the predictive relationship is different than the analysis to determine the prevalence of a condition because the prevalence analysis may be used to establish who has the condition. However, the occurrence predictor may be used to establish the health related characteristics that are needed to predict the likelihood of developing the health condition. In one embodiment, all of the health related information associated with a member having a condition, or all of the health related information believed to be potentially relevant to a health condition that a member has, may be analyzed to establish the relationship. The health related information to be analyzed may be historical data that pre-dates the incidence of the health condition.

The analysis and associated relationship may indicate the pre-detectable characteristics associated with a health condition. Pre-detectable characteristics are characteristics that impact the chance of acquiring risk factors associated with a condition. A pre-detectable characteristic may be associated with more than one risk factor and/or more than one health condition. A heart attack is an example of a health condition. Risk factors associated with a heart attack may include obesity, age, and gender. A risk factor may be described as one form of a heath related characteristic that is a known, believed, or hypothesized to be an indicator of acquiring a health condition, or increasing the risk of acquiring the health condition. Risk factors usually have one or more pre-detectable characteristics associated with them. Pre-detectable characteristics associated with obesity, or being overweight, include dietary characteristics, such as the amount of saturated fat, fiber, and calories consumed during a time period. By reducing the amount of saturated fat consumed (a pre-detectable characteristic), the chances of acquiring the associated risk factor may be reduced (e.g., reduced chance of being overweight). If the chances of acquiring a risk factor is reduced or eliminated, then the chances of acquiring an associated health condition (e.g., the heart attack) are also reduced or possibly eliminated. As will be discussed, one embodiment of the present disclosure is associated with identifying pre-detectable characteristics associated with a health condition, and then predicting an incident of the condition associated with a particular member based on the particular health related characteristics associated with that member. Intervention recommendations may then be tailored to the particular pre-detectable characteristics exhibited by the particular member. In one embodiment, the collected health related characteristics may be detailed and extensive in order to acquire the desired information that may be associated with possible pre-detectable characteristics. By the nature of the analysis being performed, the pre-detectable characteristics may not be initially known. Therefore, monitoring of future occurrences of the condition, and analysis of the associated health-related characteristics enables the predictive relationship to evolve as new information is available.

The details of the establishment of the relationship will be described below. However, in general, the health related information associated with the population will be analyzed to establish the relationship. The analysis may include the use of statistical analysis techniques such as classical, Bayesian, and/or machine learning analysis techniques to analyze the health related information. For example, neural networks may be trained using all the health related characteristics of the members having a particular condition. Then, the health-related characteristics of a member of the population may be delivered to the neural network for analysis. The resulting analysis may provide a weighted answer indicative of the likelihood the person will acquire the condition. In addition, review of the neural network may provide insight into which health characteristics are more relevant to acquiring the condition. These characteristics may then be reviewed to establish the pre-detectable characteristics associated with the condition. For example, the relevant health related characteristic may be a pre-detectable characteristic, or may have associated pre-detectable characteristics. Therefore, depending on the specific implementation used, the analysis may be able to indicate the health related characteristics that are most relevant to the prediction of a particular health condition.

The relationship may be used to analyze the population with respect to the health condition. For example, the relationship may be used to predict the likelihood of developing a condition associated with the population, or a portion thereof. As such, the relationship may be used to predict a future incident or occurrence of the health condition. In one embodiment, the health related information associated with one of the members of the population may be analyzed using the established relationship. The analysis may indicate, or predict, whether the member will develop a particular disease, which may include the likelihood the member will develop the particular disease. The analysis may be used to predict the occurrence of the disease based upon the established pre-detectable characteristics. In addition, this analysis, or information resulting from the analysis may be used to predict an incidence of the health condition, e.g., over a specified period of time, how many members will develop the disease, or what is the likelihood of a particular portion of the population developing the disease over a specified time period.

In one embodiment, depending on the health condition associated with the analysis, the analysis may also establish a predicted time period in which the incident may occur (e.g, the next year, next five years, next ten years, etc.). In addition, the analysis may establish a stage of the condition associated with a particular member. For example, some conditions may have definable stages of the onset of the disease.

In one embodiment, a likelihood of developing the condition may be established based upon the analysis. For example, some analytic techniques produce information associated with the likelihood of having the incidence, e.g, a confidence level. Therefore, the analysis may include classifying all or a portion of the population with respect to one or more conditions, based on the likelihood of the particular members having an incidence of the disease, based on the particular stages of the condition the population members fall within, and/or based on the predicted time period associated with the incidence. In this manner the population may be classified, or ranked, with respect to the likelihood of developing a condition, the time period in which the development may occur, and/or the stage of the condition the member is in. As described below, this classification, or ranking of the population, or a portion thereof, with respect to one or more conditions enables, specific interventions to be applied to specific members based on predicted risk, and also enables the management of the population as a whole, and the intervention and associated cost, etc. Therefore, the population may be analyzed to establish a likelihood of developing of one or more conditions, among one or more members of the population.

An intervention may be recommended in response to the likelihood of developing the health condition. Factors that may be used to select the appropriate intervention include the predicted likelihood the member will develop the health condition and the pre-detectable characteristics the member exhibits that are associated with the condition. For example, the more likely the person is to acquire a particular condition, the more aggressive the intervention recommendation may be. Other health related characteristics may also be used to determine the appropriate intervention, such as the self-efficacy characteristic and/or readiness to change characteristic associated with the member, and the likelihood of success of the intervention. The cost of the intervention may also be a factor in intervention selection. The role of intervention cost may be based on the premise that there is a finite amount of money available to administer health care interventions to the population. Therefore, one use of the analysis may be to determine how the interventions may be applied in a cost effective manner, while providing the best benefit for the population. For example, given the choice between recommending an intervention that is 60% effective and an intervention that cost twice as much, but is only 62% effective, the decision may be to apply the less expensive, yet effective intervention, and use the "savings" in other areas of the health care program.

One implementation may include the step of establishing a success characteristic associated with the intervention. The success characteristic may include a characteristic associated with the success of the intervention, e.g., did the intervention succeed (or assist in succeeding) the prevention or delay of the incidence of the health condition. The success characteristic may include characteristics associated with whether the intervention was used, to what degree the intervention was used, why the intervention was, or was not used, and how effective was the intervention in light of how much it was used. Some of these success characteristics may be established shortly after recommending the intervention (e.g., was the intervention used and why or why not, to what degree the intervention was used, if not used what would it take to motivate the member to use, etc.), while other success characteristics may not be established for a period of time (e.g., if used, how successful was the intervention).

Success characteristics may be collected in several ways. Fitness sensors on the phone, watch, or foot can detect changes leading to/from success and provide appropriate warnings to the user or an assigned health coach. The characteristics may also be collected through medical and/or drug related information. For example, an intervention may include a recommendation that the member visit a medical provider (e.g., doctor), have a medical test performed, and/or be prescribed a particular drug. The members medical and/or drug claims may be monitored to determine if the recommendation was followed. For example, if over a particular time period, e.g., three months, there is no indication from reviewing medical claims, that the member visited a medical provider, then the assumption may be made that the member did not follow the recommendation. In light of this, a health care counselor or provider may be notified, and the member contacted to verify they did not follow the recommendation, and determine why the recommendation was not followed (if indeed it wasn't). This may be done by monitoring claims either manually or in an automated fashion, e.g., through the use of a computer program. For example, once an intervention is recommended, a computer related program may be configured to automatically review medical, drug claims, and/or self assessment characteristics to monitor characteristics of whether the recommended intervention was performed. In addition to fitness device reporting or through claims reporting, the success characteristics may be collected through self-reported data (e. g., targeted questionnaires, interviews, one on one phone calls such as counseling phone calls, etc.). For example, if a particular intervention recommended a medical visit, the targeted questionnaire or counseling call may specifically inquire as to whether the medical visit was made, and why or why wasn't the visit made.

In one example, the success characteristics may include information indicative of a persons self-efficacy, and/or readiness to change. For example, if the established predictive relationship indicates that a particular member is at risk for a heart attack, and part of the pre-detectable characteristics associated with a heart attack is that the member is eating too much saturated fat, an intervention recommendation may include recommending a change in lifestyle, e.g., increased exercise such as running, walking, or swimming. The success characteristics may indicate that the person did not engage in any exercise (e.g., on a subsequent self assessment). Upon further follow up (e.g., within the same questionnaire or counseling session, or in a later one), the member may indicate that they don't enjoy exercising and/or they don't perceive the need to do so. Alternatively, the member may indicate that they tried running, but their knees hurt, so they stopped, and/or they did not have access to a swimming pool. That is, while they are willing to engage in a recommended intervention, the specific intervention recommended did not work for them. Alternatively, the member may indicate that while they enjoy working out, they do not have time outside of their work and family activities to engage in the recommended intervention. The measured characteristics may also indicate that the recommended intervention was followed. In this case, information may be obtained regarding why the recommendation was followed.

The success characteristics may be used in several ways. In one embodiment, analysis may be performed with the success characteristics to establish a relationship capable of indicating or predicting a members engagement of an intervention, or willingness to engage in a particular intervention, or in any intervention. For example, the health related information, including the success characteristics, associated with members who have been recommended a particular intervention, may be analyzed. The analysis may result in a relationship that is able to establish the likelihood a particular member will follow a particular recommendation, based upon the specific health related information associated with the member. In one embodiment, the success characteristics may be used to establish a relationship capable of indicating or predicting a particular member's engagement of any recommendation, or willingness to engage in any intervention. In one embodiment, the analysis may include establishing a relationship capable of predicting a member's readiness to change stage. That is, in one embodiment, readiness to change categories may include a pre-contemplation, preparation, and action stages. If a member is in a pre-contemplation stage, they may not be willing to engage in any intervention. In the preparation stage, a member may be willing to pursue a particular intervention, but not just any intervention, or they may be willing to pursue interventions, but have not started. In the action stage, the member may be ready to take action in the appropriate intervention. By classifying a member into a readiness to change category, interventions may be further tailored for the individual member. For example, if a member is in the pre-contemplation stage, then the selected intervention may include additional counseling and/or educational literature associated with the seriousness of the potential condition, and the risk associated with this particular member of acquiring the condition if no action is taken. In addition, the intervention associated with the preparation category may include customizing the proposed intervention to the interventions the member is more likely to pursue. In this manner, self-efficacy and readiness to change characteristics associated with a particular intervention, may be analyzed with other self-efficacy and readiness to change characteristics associated with other interventions, and applied to the population as a whole where appropriate. That is, some established self-efficacy and readiness to change characteristics may be generalized (e.g., by creating a predictive relationship) and applied to the whole population to predict a particular members likelihood to engage in a particular intervention, or an any intervention. The analysis may include using statistical analysis (e.g., neural networks, regression analysis, etc.) to establish a relationship that is able to predict a members willingness or ability to pursue a particular intervention. In this manner a relationship may be developed and used in future instances such that when a member is predicted to have an incidence of a condition, the recommended intervention may be based upon indirect indicators of a members self-efficacy or readiness to change, as well as direct indicators (e.g., specific questions such as: are you willing to reduce your smoking).

For example, potential interventions may include an exercise regimen, a dietary regimen or a medication, to reduce the risk of a condition. The exercise regimen may indicate the highest success rate if followed, the medication the lowest success rate if followed. In addition, the member may provide strong direct indications of self-efficacy and readiness to change characteristics. However, the established participation predictive relationship may indicate that members with similar health characteristics (e.g., job requiring long hours, area of the country not conducive to exercise during the winter, and number of dependents in the family), that the member is not likely to follow through on an exercise regiment (e.g., due to time constraints from the job and family and inclement weather). However, based on the other members, it may be predicted that this member is most likely to follow through a dietary change. Therefore, the intervention may be targeted to either changing the dietary habits of the individual.

In addition, the analysis of the success characteristics and associated health related characteristics may include establishing a relationship able to indicate a potential success of a particular intervention. For example, the success of an intervention may be established by monitoring/analyzing the health related information for an extended period of time. The health related information, including characteristics indicative of the incidence of the health condition may be monitored after the intervention is applied, and compared to health related characteristics expected if the intervention had not been applied (e.g., whether an incidence of the health condition would occur, when it would occur, when the stages of the incidence (if any) would occur. In addition, the health related characteristics may be analyzed to determine if any immediate changes in health care characteristics occurred. For example, if the health condition is a heart attack, and one of the pre-detectable characteristics associated with heart attacks is a members consumption of high saturated fats, then one intervention recommendation may be a dietary program. The health care characteristics may be monitored to determine if the dietary program was successful in reducing the members saturated fat consumption, and/or whether the dietary program was successful in eliminating or delaying the incidence of the health condition. Therefore the success of the intervention may be monitored with respect to eliminating or delaying the health condition, and/or eliminating or reducing a cause associated with the health condition. The results of the intervention monitoring and associated health related characteristics may be used to further refine the decision process regarding which intervention to recommend.

The health related characteristics, including the success characteristics, may be used to select one or more interventions for a particular member at risk of a particular condition. In addition, the health related characteristics may be used to establish a relationship that associates one or more interventions with particular health related characteristics and a health condition. The success characteristics may indicate that interventions have varying degrees of success based upon the health related characteristics such as the physical characteristics of the individual engaged in the intervention, the thoroughness of the use of the intervention, the willingness of the person to pursue, etc. For example, assume there are two potential interventions for a health condition. Assume intervention 1, if followed 100%, is 90% effective, and if followed 50% is 30% effective. In addition, assume intervention 2, if followed 100% is 60% effective, and if followed 50% is 45% effective. Depending on the health related characteristics of a particular member, the best chance of preventing or delaying the condition (or eliminating a cause of the condition) may lie with pursuing intervention 2. For example, if the self-efficacy characteristic, or readiness to change characteristic is low, this may be an indication that the member won't follow through completely with the recommendation. Therefore, the second intervention may be pursued that may have a better impact than the first intervention given that neither intervention is used completely. Therefore, a relationship may be developed that is able to predict the effectiveness of a particular intervention in general, e.g., if the intervention is used X %, then it will be Y % effective. This information may be used to make an intervention recommendation to a member or, to engage in further correspondence (interviews, follow-up questionnaires, etc.) with the member. For example, the member may be notified of the preferred intervention, but of the concerns that they are not going to fully engage the intervention. If they don't fully engage the intervention then there is an alternative intervention that is preferred. In addition, a relationship may be established to predict the usage of an intervention by a particular member, based upon the health related characteristics of the member. The relationship may also be able to predict the success of a particular intervention based on the predicted use of a member (e.g., based on the members self-efficacy, readiness to change, and or other health related characteristics). In addition, interventions may have varying success among different members, even if pursued to the same degree. Therefore, the recommendations may be modified based on any previous engagement by the member in an activity related to an intervention. For example, health related characteristics associated with the member and the activity the member engaged in may be used to tailor the specific recommendation provided.

In one embodiment, the success characteristics associated with a particular member may be used to further refine, or establish, a recommended intervention for the member. In addition, the success characteristics may be used to refine the analysis (e.g., relationship) that correlates a member of a population with a particular intervention, based on the health related characteristics of the member.

A relationship is established between the health related characteristics and a health condition. The type of analysis used to establish the relationship is implementation dependant and may vary as a function of the data available information being requested (e.g., explain the similarities/dissimilarities of the health related characteristics of members having the condition, predict future incidences, or both). The analysis may be dependent on the number of dependent variables (e.g., the health condition(s) associated with data) and/or independent variables (e.g., health related characteristics) that are being analyzed in the relationship and/or the objective of the analysis being performed. For example, the analysis may include the use of statistical analysis techniques such as classical, Bayesian, and/or machine learning techniques. Classical analysis techniques may include multivariate statistical techniques simple regression, multiple regression, factor analysis, item analysis multivariate analysis of variance, discriminant analysis, path analysis, cluster analysis, multidimensional scaling, rule induction, and/or least squares estimation. In one embodiment, multiple regression may be used to determine the relationship between one dependent variable (e.g., whether a person has diabetes) and multiple independent variables (i.e., multiple other health related characteristics, such as weight, gender, age, dietary habits, walking/running/exercise, etc.). Other techniques, such as in factor analysis, cluster analysis, and multivariate techniques may be used when the desired relationship is associated with multiple dependent variables and multiple independent variables. Generic model-fitting or classification algorithms e.g., neural networks (e.g., back propagation, feed-forward networks, etc.), meta-learning techniques such as boost, etc., may be applied for predictive data mining. Predictive data mining techniques may be desired when the accuracy of a prediction is of higher priority, regardless of whether or not the models or techniques used to generate the prediction is interpretable or open to simple explanation. That is, data mining techniques may be desired when the objective is to predict the future occurrence of a health condition, as opposed to analyze the existing relationship among the health related characteristics that leads to the health condition. As mentioned, the selection of the particular analysis technique(s) is implementation dependent and may be based on factors such as user preference, the data to analyze, and the number of dependent and/or independent variables, the objectives of the analysis. Therefore, in one embodiment of the present disclosure, the person analyzing the health of the population may specify the analysis techniques to be used, or the analysis system may automatically determine the appropriate technique(s) to use.

In one embodiment, data analysis using deep neural network techniques may be used to establish a predictive relationship between the health related characteristics and one or more health conditions. For example, the health related characteristics associated with members known to have a particular health condition, may be used to "train" the neural network. There are several types of neural network models. The selection of which model or combination to use may be implementation dependent, and implementation accuracy may vary based on model used, data analyzed, and desired objective of the model. In one embodiment, the model used is a back propagation network. The back propagation network may receive the health related characteristics associated with the members known to have a particular health condition, along with the characteristics of members known not to have the characteristic. The resulting "trained" neural network may then be able to receive the health related characteristics of a member to predict whether they will acquire the health condition. In one embodiment, the neural network output is a number (e.g., between zero and one), that may be used to indicate that the member has a determined likelihood of having an incidence of the condition (e.g., 75%), if they do not already have it. As was discussed above, the resulting likelihood of occurrence may be used to rank the population in terms of likelihood of acquiring the condition. This ranking may then be used to prioritize intervention strategies.

In addition to establishing a likelihood of occurrence of the health condition, the internal organization of the neural network may be analyzed to determine which health related characteristics where most relevant to the condition. For example, a back propagation network includes multiple weighted interconnections between the input factors and the output. The weighted interconnections may be reviewed and correlated with the input health related characteristics. In this manner, the characteristics having more relevance (e.g., a higher weighting value) may be identified. These relevant characteristics may then be reviewed to establish the pre-detectable characteristics of associated with the health condition. For example, the established health related characteristics may already be pre-detectable characteristics (e.g., the amount of salt consumed per day, the amount of saturated fat consumed per day). However, if the established health related characteristics are not pre-detectable characteristics, then further analysis may be performed to break the characteristics into the pre-detectable characteristics. For example, if being overweight is established as a relevant health related characteristic, then further analysis may be performed to determine what pre-detectable characteristics lead to being overweight, and which of these pre-detectable characteristics did members being analyzed exhibit. In one embodiment, all of the factors associated with being overweight may be treated as being relevant. Alternatively, the potential pre-detectable characteristics are used to further refine the relationship to establish which of the pre-detectable characteristics plays a role in being overweight, when overweight is a factor in having a particular health condition, e.g., diabetes.

In one embodiment, if multiple regression is the analysis technique used, an equation associated with the relationship may be: $Y = b1 \times 1 + b2 \times 2 + \ldots bnXn + c$, where the b's are the regression coefficients, representing the amount the dependent variable Y (e.g., likelihood of contracting a health condition) changes when the independent variable (the X's, e.g., the health related characteristics) change 1 unit. The c is the constant, where the regression line intercepts the y axis, representing the amount the dependent variable Y will be when all the independent variables are 0. In one embodiment, a determination may be made regarding whether any transformation (e.g., log functions, square roots, etc.) are needed to the proposed relationship (or equation). For example, should the log of a health related characteristic be used in the relationship, should the square root of a health related characteristic be used in the relationship, etc. As will be discussed, the form of the equation, e.g., whether one or more transformations are used, may be determined by the user, by the analysis system, or a combination thereof.

In one embodiment, different relationships may be created, e.g., using different transformations or different health related characteristics for the multiple regression analysis, and analyzed to determine which relationships perform better than others. Goodness of Fit analysis techniques such as $R2$, RMS, P Value, F ratios, standard error, etc., may be used to establish performance characteristics of the relationships. For example, techniques such as $R2$, which establish the percent of variance in the dependent variable (e.g., the part characteristic cost), explained collectively by the independent variables (e.g. the other part characteristics). By using $R2$, for example, an assessment may be made regarding which relationship best explains the variance in the dependent variable in response to the independent variables. RMS provides an indication of which model best predicts future aspects of a part, or part to be designed.

In one embodiment, a threshold level of desired performance may be established for the relationship. If the relationship does not meet the threshold level of desired performance, then the user may be notified that the established relationship does not meet the desired level of accuracy, the desired level of ability to explain the variance in the dependent variable in response to the independent variables, or desired level of ability to predict future characteristics of the part. If multiple relationships are being compared with each other, and none of them exceed the desired level of success, then the user may be notified of which relationship performed best, but that none of them met the desired threshold. If multiple relationships are tested and one or more exceed the threshold, the best one may be selected, or they may all be provided to the user for selection.

One method for performing population health management includes establishing a plurality of health related characteristics associated with the population; establishing a relationship between the health related characteristics and at least one health condition; and analyzing at least a portion of said population in response to said relationship. The system can predict a likelihood of at least one of said members developing said at least one health condition, in response to said relationship and/or the members health related characteristics. The system can determine a prevalence of a health condition within said population in response to said health related characteristics. The plurality of health related characteristics associated with said population can be done by establishing a plurality of self-reported characteristics associated with at least a portion of said population. A prevalence of the health condition can be determined by: establishing a plurality of claims associated with at least one of said members, said claims including at least one of a drug claim and a medical claim; cross checking said plurality of claims (such as over a period of time, or over a number of tests); and establishing said prevalence in response to said cross checked claims. The system includes predicting a member's likelihood of developing a condition with a stage of said condition in response to said prediction. The system can predict a time period associated with said development. The system can classify said population in response to said prediction, and then prioritize treatment of the population in response to said prediction.

The system can recommend an intervention in response to said predicted likelihood of development. This can be done by establishing a plurality of intervention recommendations associated with said condition; establishing a success characteristics of said recommended intervention; establishing at least one of a readiness to change characteristic and a self-efficacy characteristic of said member; and recommending said intervention in response to said plurality of intervention recommendations, associated intervention success characteristics, and member health related characteristics, said health characteristics including said self-efficacy and said readiness to change characteristic.

The system can monitor failure/successful characteristic of said intervention, and determining causes resulting in said success characteristic. The system can capture a plurality of self-reported data associated with at least a portion of said population having said condition. The self-reported data includes at least one of a lifestyle characteristic, a family history characteristic, and a health characteristic. The predictive relationship can be done by establishing at least one objective of said relationship; dynamically selecting a statistical analysis technique in response to said objective; and establishing said relationship in response to said statistical analysis technique. The predictive relationship can be applied to at least a portion of said population; and predicting a likelihood of developing said condition in response to said application.

The system can be configured to analyze the health of a population having multiple members. In one embodiment, the method includes the steps of establishing a plurality of health related characteristics associated with the population, the characteristics including a plurality of pre-detectable characteristics, establishing a relationship between the health related characteristics and the health condition, and predicting an incident of the health condition associated with at least one of the members, in response to the relationship. The health condition may be any type of physical or mental health condition, disease, and/or ailment. For exemplary purposes the method and system will be discussed as they may relate to the health condition diabetes. A repository of health related characteristics associated with a population may be collected. The health related characteristics may be collected through sources such as medical claims, drug claims, and self-reported information. The characteristics may include health characteristics, lifestyle characteristics, and family history characteristics. The characteristics may include the amount of saturated fat, unsaturated fat, fiber, salt, alcohol, cholesterol, etc. that a member consumes in a give time period. The characteristics may include weight characteristic, such as a member's weight, BMI (Body Mass Index), abdominal girth, etc. The characteristics may also include the person's blood pressure, standing heart rate, exercise habits (type and duration), and whether the member has hypertension. The health related characteristics of the population may be analyzed to establish the prevalence of diabetes among the population. For example, a medical claim having an ICD code with the prefix 250 is an indicator that the member may have diabetes. In addition, drug claims having a medication code descriptive of an anti-diabetes medication are indicators that the member has diabetes. The medical and/or drug claims are analyzed to determine if two claims indicating a member may have diabetes, and that are separated by at least three months, occur. If two claims meeting the criteria are identified, then the member is determined to have diabetes. For example, if two separate ICD codes occur, separated by at least three months, or one such ICD code occurs and one drug code for anti diabetes medication occur, e.g., separated by at least three months, then the member may be determined to have diabetes.

Once the population has been analyzed to establish who has diabetes, the historical health related characteristics of the diabetics are then used to establish a relationship between diabetes and the health related characteristics. For example, the health related characteristics are used to establish a neural network model, or regression model. The trained neural network and/or regression model will then be able to predict the likelihood a member of the population will acquire diabetes. In one embodiment, the neural network will also be able to establish who has, or may acquire, the related diabetic characteristics of metabolic syndrome and or glucose intolerance. Alternatively, these may be inputs to the neural network if available.

The established relationship may be reviewed to determine what the pre-detectable characteristics associated with diabetes are. For example, it may be determined that salt intake, consumption of saturated fats, and alcohol consumption are three leading pre-detectable characteristics of acquiring diabetes. In addition, it may be determined that smoking is not a pre-detectable characteristic associated with diabetes. The population may then be reviewed using the established relationship. The health related characteristics of each member of the population not known to have diabetes may be analyzed using the relationship. The analysis may indicate the likelihood the person will acquire diabetes (e.g., 75% likely). In addition, the pre-detectable characteristics associated with diabetes that are exhibited by the person may be identified. In this manner, the likelihood of the acquiring diabetes may be established along with what pre-detectable characteristics are the primary contributors to this particular member having diabetes.

Once the population's health related characteristics are analyzed, the population may be ranked by the individual member's likelihood of acquiring diabetes. In this manner, the type of intervention may be recommended based on the risk of acquiring diabetes, and the pre-detectable characteristics the member exhibits. In one embodiment, the interventions may be recommended by using another relationship (or an elaboration of the predictive relationship) to automatically make the recommendation based on the health related characteristics of the member, which may include the likelihood of acquiring diabetes and specific pre-detectable characteristics exhibited, self-efficacy and readiness to change characteristics of the member, etc. In one embodiment, the intervention may include additional questionnaires or interviews to acquire more specific information associated with diabetes from the individual. Other forms of intervention include one on one counseling to convince the member of the seriousness of diabetes, the risk of acquiring diabetes associated with them, the ability to delay or prevent the onset of diabetes by changing specified lifestyle characteristics, and the specific actions the member may take to modify specific aspects of their lifestyle associated with the pre-detectable characteristics. For example, if dietary issues are causing the member to be overweight, the intervention may include, suggested changes to dietary consumption, cookbooks directed towards the desired diet, or even corporate sponsored diet counseling or involvement in a commercial diet control program. The specific intervention recommended may be based on the likelihood of acquiring diabetes the person has, the members willingness to change their diet and belief that they will be successful in long term dietary change, and how much of a factor dietary issues were in establishing this particular members likelihood of acquiring diabetes.

Once the intervention recommendation is provided additional monitoring may occur to determine if the member followed through with the recommendation (including why they did or didn't follow through), whether the intervention helped reduce the targeted characteristic (e.g., the targeted pre-detectable characteristic), and when the intervention did reduce the targeted characteristics, whether the ultimate occurrence of diabetes was either delayed (which may be a subjective determination) or prevented altogether. The results of this monitoring may then be used to update the established relationships. In addition, as incidents of diabetes occur, the health related characteristics of effected member may be used to further refine the established predictive relationship. In this manner, the health of the population may be analyzed and managed relative to diabetes.

The system can receive data from electronic medical records (EMRs), activity data from patient watches and wearable devices, population demographic information from govt databases, consumer profile information from credit card companies or consumer sales companies, provider (doctor, dentist, caregiver) entered information, one or more output registry databases. The EMRs may span multiple applications, multiple providers, multiple patients, multiple conditions, multiple venues, multiple facilities, multiple organizations, and/or multiple communities. Embodiments of the EMRs may include one or more data stores of healthcare records, which may include one or more computers or servers that facilitate the storing and retrieval of the healthcare records. In some embodiments, one or more EMRs may be implemented as a cloud-based platform or may be distributed across multiple physical locations. Example embodiments of the EMRs may include hospital, ambulatory, clinic, health exchange, and health plan records systems. The EMRs may further include record systems, which store real-time or near real-time patient (or user) information, such as wearable, bedside, or in-home patient monitors, for example. It is further contemplated that embodiments of the EMRs may use distinct clinical ontologies, nomenclatures, vocabularies, or encoding schemes for clinical information, or clinical terms. Further, in some embodiments, the EMRs may be affiliated with two or more separate health care entities and/or venues that use two or more distinct nomenclatures.

In embodiments, the EMRs described herein may include healthcare data. As used herein, healthcare data refers to any healthcare or medical care data related or relevant to a patient. Healthcare data may include, but is not limited to, clinical data and healthcare-related financial data. Clinical data, as used herein, refers to any healthcare or medical data particular to a patient. In embodiments, clinical data can be medical care or healthcare data resulting from or associated with a health or medical service performed in association with a clinician in a healthcare environment (e.g., lab test, diagnostic test, clinical encounter, ecare, evisit, etc.). Clinical data may include, but is not limited to, a health history of a patient, a diagnosis, a clinician assessment, clinician narrative, a treatment, a family history (including family health history and/or family genetics), an immunization record, a medication, age, gender, date of birth, laboratory values, diagnostics, a test result, an allergy, a reaction, a procedure performed, a social history, an advanced directive, frequency and/or history of healthcare facility visits, current healthcare providers and/or current healthcare provider location, preferred pharmacy, prescription benefit management data, an alert, claims data, a vital, data traditionally captured at the point of care or during the care process, a combination thereof, and the like. In the same or alternative embodiments, the clinical data may include medical compliance information. In certain embodiments, medical compliance information refers to a level of compliance of a particular patient with one or more prescribed medical treatments, such as medications, diet, physical therapy, follow up healthcare visits, and the like. In one or more embodiments, the clinical data may include data obtained from the natural language processing of one or more clinical assessments and/or clinical narratives.

In certain embodiments, healthcare-related financial data can refer to any financial information relevant to a patient, such as insurance data, claims data, payer data, etc. Such healthcare data (e.g., clinical data and healthcare-related financial data) may be submitted by a patient, a care provider, a payer, etc. In certain embodiments where the healthcare data is being submitted by anyone other than the patient, the patient may be required to approve of such submission and/or may opt-in to or opt-out of having such healthcare data being submitted.

In embodiments, activity data can refer to health actions or activities performed by a patient outside of, or remote from, a healthcare environment. Embodiments of activity data may include one or more data stores of activity data, which may include one or more computers or servers that facilitate the storing and retrieval of the activity data. In some embodiments, the activity data may be implemented as a cloud-based platform or may be distributed across multiple physical locations. Example embodiments of the activity data may include nutrition information and/or exercise information for a patient. In certain embodiments, at least a portion of the activity data may be recorded utilizing a personal fitness tracker, a smart phone, and/or an application provided by a smart phone. In various embodiments, the activity data may include data obtained from a patient's car. For example, in such embodiments, the activity data include data on the amount of driving the patient does versus the amount of walking the patient does.

In one or more embodiments, the activity data may be submitted by a patient, a third party associated with a personal fitness tracker and/or smart phone (such as a software developer or device manufacturer), a care provider, a payer, etc. In certain embodiments where the activity is being submitted by anyone other than the patient, the patient may be required to approve of such submission and/or may opt-in to or opt-out of having such healthcare data being submitted.

The patient and/or population demographic information may include age, gender, date of birth, address, phone number, contact preferences, primary spoken language, technology access (e.g., internet, phone, computer, etc.), transportation (e.g., common modes of transportation), education level, motivation level, work status (student, fulltime, retired, unemployed, etc.), and/or income. In certain embodiments, the patient and/or population demographic information may include community resource information, which may include, but is not limited to, fitness facility information, pharmacy information, food bank information, grocery store information, public assistance programs, homeless shelters, etc. In embodiments, the motivation level can include the level of motivation a particular patient has for maintaining their health, which may be derived from other information (e.g., data from personal fitness tracker, indication the patient regularly visits a clinician for checkups, consumer profile information, etc.). Embodiments of the patient and/or population demographic information may include one or more data stores of demographic information which may include one or more computers or servers that facilitate the storing and retrieval of the demographic information. In some embodiments, the patient and/or population demographic information may be implemented as a cloud-based platform or may be distributed across multiple physical locations. In embodiments, the patient and/or population demographics may be obtained through any source known to one skilled in the art. For example, in certain embodiments, at least a portion of the patient and/or population demographic information may be submitted by a third party that relies on census data. In various embodiments, the patient and/or population demographic information may be obtained from more than one source. In one embodiment, the patient may submit any or all of the patient and/or population demographic information. In certain embodiments, all or a portion of the patient and/or population demographic information may be anonymized using techniques known to one skilled in the art.

In one or more embodiments, the consumer profile information may include any or all of the spending habits of one or more patients within a population. For instance, in certain embodiments, the consumer profile information may include information associated with grocery store purchases, athletic or exercise equipment purchases, restaurant purchases, and/or purchases of vitamins and/or supplements. Embodiments of the consumer profile information may include one or more data stores of consumer profile information which may include one or more computers or servers that facilitate the storing and retrieval of the consumer profile information. In some embodiments, the consumer profile information may be implemented as a cloud-based platform or may be distributed across multiple physical locations. In one embodiment, a patient may provide the consumer profile information, for example, by linking checking account and/or checking account purchase information to at least a portion of the population health management system and/or to a health insurance carrier.

The care provider information may include any information relating to a particular care provider or healthcare facility. In one embodiment, the care provider information may include information relating to the number of healthcare providers and their specialties at a particular care provider location. In the same or alternative embodiments, the care provider information may include information relating to non-personnel type resources at a particular care provider location, such as the amount and types of medications and/or the amount and types of surgical or other medical equipment. In one embodiment, the care provider information may include one or more of address and contact information, accepted payer information, status on accepting new patients, transactional systems, primary spoken language, hospital affiliations, and/or care delivery models. In embodiments, the care provider information may include information relating to the availability of any or all resources at a particular healthcare facility including personnel and/or non-personnel resources. Embodiments of the care provider information may include one or more data stores of care provider information which may include one or more computers or servers that facilitate the storing and retrieval of the care provider information. In some embodiments, the care provider information may be implemented as a cloud-based platform or may be distributed across multiple physical locations. In one embodiment, the care provider information can be provided by a healthcare provider, and/or a third party, such as an insurance provider or management entity.

Information in the output registry databases may be categorized or classified according to, for example, claims, diagnoses, wellness, satisfaction, population directories, and the like. In various embodiments, each output registry may be used by, for example, a healthcare organization to manage the health of a population segment. In one or more embodiments, each output registry may be condition specific. By way of example, a healthcare organization or clinician may manage diabetic patients within a proscribed geographic area. The condition in this example is diabetes mellitus and the output registry may help the healthcare organization manage a population segment with this condition. The output registry may, in one aspect, include identified patients within a population segment who have this condition or have risk factors that may lead to the development of diabetes, for example. The output registry may further include grouped patients within an identified segment by degree of severity or risk, such as those grouped by the grouping component of the population health server. The grouped patients in an output registry may facilitate the generation of interventions or action workflows designed to reduce disease severity or risk and to improve outcome. Additional uses for the output registries are to measure outcomes related to treatment interventions and also to attribute patients within the identified segment to appropriate healthcare providers (e.g., primary care physicians, care managers health coaches, specialists such as endocrinologists, podiatrists, and the like).

In embodiments, the plurality of EMRs may be associated with a plurality of healthcare providers, a plurality of patients, a plurality of medical conditions, a plurality of healthcare venues and/or facilities, a plurality of organizations, and/or a plurality of communities. In certain embodiments, in addition to or in place of the healthcare data, the system can receive activity data from fitness devices, demographic information, e.g., the patient and/or population demographic information; consumer information, e.g., the consumer profile information; and provider information, e.g., the care provider information.

The system can identify a population of patients based on a set of criteria, which may, in one example, be received from a clinician device such as a blood pressure unit, among others. In one or more embodiments, the set of criteria may include one or more medical conditions. In the same or alternative embodiments, the set of criteria may include demographic information of one or more patients, such as age, gender, race, and/or location of residence. In one or more embodiments, the system may utilize any or all of the information and data such as: healthcare data, e.g., the healthcare data present in one or more EMRs; activity data; demographic information, e.g., the patient and/or population demographic information; consumer profile information; and care provider information.

In certain embodiments, to identify as many people as possible in a population that may have or have a particular medical condition of interest, the system may utilize clinical data, such as lab test results, in combination with other healthcare data. In such embodiments, the particular medical condition can be any condition where specific types of clinical information, e.g., lab test results, may be used to identify one or more patients that have or may have that condition. Exemplary conditions may include, but are not limited to, diabetes and heart disease. For example, in embodiments, the system may utilize diagnostic information, medication information, and/or one or more lab test results to identify a patient as having or potentially having diabetes. In such embodiments, by using information from one or more lab test results, the system may identify one or more patients that have diabetes or may have diabetes, even if they have not been formally diagnosed with diabetes or have not been prescribed diabetes medication. In the same or alternative embodiments, the system may utilize lab test results in combination with other healthcare data to identify pre-condition patients, which may allow early intervention to prevent a patient from developing a particular condition.

In one or more embodiments, the system can identify subsets of a population not based on a medical condition. For instance, in such embodiments, the system can identify subsets of a population based on aspects of one or more patients in a population of patients, e.g., age, gender, primary spoken language, income level, healthcare motivation level, education level, technology access (e.g., phone, computer, etc.), contact preferences, work status (student, full-time, unemployed, retired, etc.), healthcare facility visit history and frequency, advanced directives, and/or consumer profile information.

In various embodiments, the system can identify subsets of a population based on non-medical aspects of patients, specific care provider information, and/or population and/or community based resources in order to enable actions and care planning, measure compliance, improve care transitions, optimize utilization of resources, and contain costs.

In one or more embodiments, the system can group a population of patients based on a clinically relevant data from the EMRs. For example, in embodiments, the clinical data may include one or more of medication information, laboratory values, diagnostics, clinical narratives, and clinician assessments. In the same or alternative embodiments, the clinical data may include data obtained from the natural language processing of one or more clinical assessments and/or clinical narratives. In certain embodiments, the system can group a population of patients based on diagnostic codes, intervention codes, insurance claims, and/or medication information associated with each patient. The system can also group patients using substantially similar attributes can include one or more of disease risk levels and/or scores, one or more disease stages, and/or one or more healthcare objectives. For example, in certain embodiments, the system can group a population of patients, such as a population of patients identified as having or potentially having diabetes, into at least two groups corresponding to Type I and Type II diabetes.

The system can group based on venue location, specialty, spoken language, readmission rate, medical and/or prescription compliance level, socioeconomic status, address, employment status, marital status, education level, age, sex, dependents, race, ethnicity, insurance status, and primary spoken language, associated healthcare support system, and/or utilization level of healthcare facilities (including pharmacies). The grouping can finely classify individual patients as having a low, medium, or high medication compliance risk based on information related to the ability to access a pharmacy, the ability to pay for medications, and/or the presence of medication gaps in the healthcare record. In other embodiments, individual patients may be grouped based on the number of appointments made, the number of appointments scheduled, the number of appointments attended, the number of missed appointments, the type of appointment, the date and time of the appointment, the visit location, the venue, and whether or not the patient acknowledged the appointment (e.g., was the patient aware of the appointment). The system can predict patients as having a low, medium, or high level of compliance with filling prescriptions based, at least in part, on the number of prescriptions written, the number of prescriptions filled, and the date and time the prescriptions were filled.

The information includes genetic data. The system can model diseases as the result of multiple genetic mutations interacting with environmental factors, diet and lifestyle choices, microbiome differences and metabolic responses.

In one embodiment, the medical data includes sequenced body fluid samples containing circulating tumor cells (CTCs) and cell-free DNA (cfDNA). CTCs have an intact, viable nucleus; express cytokeratins, which demonstrate epithelial origin; have an absence of CD45, indicating the cell is not of hematopoietic origin; and have morphology consistent with cancer, often larger cells with irregularity cell or subcellular morphology. Cytokeratin negative (CK-) CTCs are cancer stem cells or cells undergoing epithelial mesenchymal transition (EMT). CK-CTCs may be the most resistant and most prone to metastasis; express neither cytokeratins nor CD45; have morphology similar to a cancer cell; and have gene or protein expression or genomics associated with cancer. Apoptotic CTCs are traditional CTCs that are undergoing apoptosis (cell death). Measuring traditional CTC to apoptotic CTCs ratio from baseline to therapy provides clues to a therapy's efficacy in targeting and killing cancer cells. Small CTCs are cells that are cytokeratin positive and CD45 negative but have a size and shape similar to white blood cells. Importantly, small CTCs have cancer specific biomarkers that identify them as CTCs. Small CTCs have been implicated in progressive disease and differentiation into small cell carcinomas which often require a different therapeutic course. CTC Clusters are made up of two or more individual circulating tumor cells bound together. The CTC cluster can be made up of traditional, small or CK-CTCs. CTC clusters have cancer specific biomarkers that identify them as CTCs and are associated with increased metastatic risk and poor prognosis.

In another embodiment, the medical data is captured from sequenced from microvesicles isolated from a sample taken of a bodily fluid from a subject. As used herein, a "bodily fluid" refers to a sample of fluid isolated from anywhere in the body of the subject, preferably a peripheral location, including but not limited to, for example, blood, plasma, serum, urine, sputum, spinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, bronchoalveolar lavage (BAL), cyst fluid, tumor cyst fluid, amniotic fluid and combinations thereof. Preferably, the bodily fluid is plasma, serum, cerebrospinal fluid, ascites fluid, bronchoaveolar lavage, or cyst fluid. In some embodiments, it is preferable that the bodily fluid sample is within the range of 2-20 ml. In some aspects, it may be preferable to use a larger volume of sample for increased accuracy in detecting rare genetic mutations, such as the BRAF mutation described herein. In some aspects, the bodily fluid sample is within the range of 1 to 25 ml, for example, from 2 to 25 ml, from 2 to 20 ml, from 2 to 15 ml, from 2 to 10 ml, from 4 to 25 ml, from 4 to 20 ml, from 4 to 15 ml, from 4 to 10 ml, from 6 to 25 ml, from 6 to 20 ml, from 6 to 15 ml, from 6 to 10 ml, from 8 to 25 ml, from 8 to 20 ml, from 8 to 15 ml, from 10 to 25 ml, from 10 to 20 ml, from 10 to 15 ml, from 15 to 25 ml or from 15 to 20 ml.

Following the isolation of microvesicles from a biological sample, nucleic acid may be extracted from the isolated or enriched microvesicle fraction. Nucleic acid molecules can be isolated from a microvesicle using any number of procedures, which are well-known in the art, the particular isolation procedure chosen being appropriate for the particular biological sample. The extracted nucleic acids can be DNA and/or RNA. In some embodiments, the DNA is extracted. In some embodiments, RNA is extracted. In some embodiments, both DNA and RNA are extracted. The RNA can be messenger RNA, transfer RNA, ribosomal RNA, small RNAs, non-coding RNAs.

In one embodiment, the extracted nucleic acid is RNA. RNAs are then preferably reverse-transcribed into complementary DNAs before further amplification. Such reverse transcription may be performed alone or in combination with an amplification step. One example of a method combining reverse transcription and amplification steps is reverse transcription polymerase chain reaction (RT-PCR). The analysis of nucleic acids present in the microvesicles is quantitative and/or qualitative. For quantitative analysis, the amounts (expression levels), either relative or absolute, of specific nucleic acids of interest within the microvesicles are measured with methods known in the art (described below). For qualitative analysis, the species of specific nucleic acids of interest within the microvesicles, whether wild type or variants, can be identified.

The system can capture 'omics data, including genomics, transcriptomics, proteomics, and metabolomics data, to understand the biology of an organism and its response to environmental stimuli or genetic perturbation. Metabolome refers to the complete set of small-molecule metabolites (such as metabolic intermediates, hormones and other signaling molecules, and secondary metabolites) found in a sample. Analytes in a metabolomic sample comprise highly complex mixture. This complex mixture can be simplified prior to detection by separating some analytes from others. For analysis by mass spectrometry the analytes are transferred to the gas phase using electron ionization (EI), chemical ionization (CI), or electrospray ionization (ESI), among others. Identification leverages the distinct patterns in which analytes fragment which can be thought of as a mass spectral fingerprint; libraries exist that allow identification of a metabolite according to this fragmentation pattern. Alternatively, nuclear magnetic resonance (NMR) spectroscopy does not rely on separation of the analytes, and the sample can thus be recovered for further analyses.

Once metabolic composition is determined, data reduction techniques can be used to elucidate patterns and connections. A principal component analysis (PCA) can be used to efficiently reduce the dimensions of a dataset to a few which explain the greatest variation. When analyzed in the lower-dimensional PCA space, clustering of samples with similar metabolic fingerprints can be detected. This clustering can elucidate patterns and assist in the determination of disease biomarkers—metabolites that correlate most with class membership. Metabolic profiling (especially of urine or blood plasma samples) detects the physiological changes caused by toxic insult of a chemical (or mixture of chemicals). In many cases, the observed changes can be related to specific syndromes, e.g. a specific lesion in liver or kidney. Metabolomics can be used for determining the phenotype caused by a genetic manipulation, such as gene deletion or insertion. Nutrigenomics is a generalised term which links genomics, transcriptomics, proteomics and metabolomics to human nutrition. In general a metabolome in a given body fluid is influenced by endogenous factors such as age, sex, body composition and genetics as well as underlying pathologies. Metabolomics can be used to determine a biological endpoint, or metabolic fingerprint, which reflects the balance of all these forces on an individual's metabolism. The system can also be used to study environmental metabolomics to characterize the interactions of organisms with their environment.

In one embodiment, metabolites and immune cell function correlating with exercise can be tracked. Blood draws and resting echocardiogram are taken. The patient exercises on a treadmill for approximately 15 minutes, followed by another echocardiogram. After the exercise and echocardiograms, periodic blood draws are done over the course of several hours. The metabolites with elevated levels are correlated with echocardiogram, electrocardiogram, VO2 max testing, and vascular ultrasound evaluation to identify metabolites associated with exercise and they are tracked over time to predict the patient's fitness level.

The system can monitor disease (e.g. cancer) progression or recurrence in a subject. These methods include isolating microvesicles from a bodily fluid of an individual and analyzing nucleic acid within the microvesicles to create a genetic profile of the microvesicles. The presence/absence of a certain genetic aberration/profile is used to indicate the presence/absence of the disease (e.g. cancer) in the subject. For example, the process includes detecting the presence or absence of one or more mutations in the extracted DNA and RNA, and the presence of the one or more mutations in the extracted DNA and RNA indicates the presence of a disease or other medical condition in the subject or a higher predisposition of the subject to develop a disease or other medical condition.

The liquid biopsy process is performed periodically over time, and the results reviewed, to monitor the progression or regression of the disease, or to determine recurrence of the disease. Put another way, a change in the genetic profile indicates a change in the disease state in the subject. The period of time to elapse between sampling of microvesicles from the subject, for performance of the isolation and analysis of the microvesicle, will depend upon the circumstances of the subject, and is to be determined by the skilled practitioner. For example, a gene which is targeted by the therapy can be monitored for the development of mutations which make it resistant to the therapy, upon which time the therapy can be modified accordingly. The monitored gene may also be one which indicates specific responsiveness to a specific therapy.

The data processed by the system of FIG. 11 is reflective of a large population by including participants from diverse social, racial/ethnic, and ancestral populations living in a variety of geographies, social environments, and economic circumstances, and from all age groups and health statuses. One embodiment applies precision medicine treatment to many diseases, including common diseases such as diabetes, heart disease, Alzheimer's, obesity, and mental illnesses like depression, bipolar disorder, and schizophrenia, as well as rare diseases. Importantly, the system can focus on ways to increase an individual's chances of remaining healthy throughout life.

In an implementation, social network information may be maintained in a computer graph structure with nodes and edges such that each node represents a user or an organization in the network and each edge represents a known direct connection between two nodes. A number of attributes described within social networks may be stored in a database, associated with each user (also referred to herein as nodes) and strength of influence (also referred to herein as edges or distances). In some embodiments, the engine may be further configured to determine distances to one or more of the patient members closest to a current patient's biological data with a diameter of at least one grouping and to indicate that the new patient is associated with the grouping based on the comparison. In various embodiments, the engine is further configured to determine if the distance to one or more of the patient members closest to the new patient's filtered biological data is greater than a diameter of each grouping and to indicate that the new patient is not associated with each grouping based on the comparison. The medical characteristic may comprise a clinical outcome.

In one implementation, nodes may comprise attributes that include but are not limited to: a unique identifier assigned such as a user's name, address and/or other items of information; unique identifiers for the node in each external social network containing the node, statistical summaries of the node's network, and pointers to the user's medical data. In an implementation, edges of the social network may comprise attributes that include but are not limited to the unique identifiers of the two nodes that are connected by the edge, the source of the node's information (i.e. the external social network), the assigned social influence from the first node to the second node, and the assigned social influence from the second node to the first node, and statistical summaries of the edge's contribution to the network.

The above mentioned examples are not intended to be limiting, and it is intended that any medical data is included within the scope of this disclosure. In an implementation, a user may be able to designate which health provider sites or medical sites that may be desirable to obtain information from, or the sites may be automatically selected. The social health content may be presented to the user or alternatively to a health professional for assessment. For example, a user may be presented with a list of all of her medical connections from her health history sites. In such an example the user may wish to select all of the available connections, or may wish to limit the selection to only a certain number of connections. A user may be asked to assign a strength of influence (for example, a numerical value) for each of the connections received from the social networks. In an implementation, the method will receive user influence information (data) by asking the user to assign a strength of influence for a connection that represents the user's similarity to another user. Likewise, the method will receive user influence information (data) by asking the user to assign a strength of influence for a connection that represents the medical influence that any other user may have over the user herself. The strength of influence information may be recorded into memory as an influence metric. Influence metrics may be discussed in the terms of distance, even though an actual distance may not exist between the points of social data used in the method. A list of recommendations may be created for the user base on his medical neighborhood and the behavior of others within the health/medical neighborhood. For example, if influential patients of the neighborhood are using and talking about certain medication or treatment modalities, it is likely that the user may desire to apply the same medication/treatment. As such, a timely recommendation from a research would prove beneficial to both the treating professional and the patient/user.

Exemplary systems and methods for disease management are provided. In various embodiments, a method comprises identifying similar patient clusters, generating groups and interconnections of the groups, each group having one or more members that share medical similarities, each interconnection interconnecting groupings that share at least one common member, determining whether a new member shares medical similarities with the one or more members of each group and associating the new member with one or more groups. The similarities may represent similarities of measurements of gene expressions or similarities of sequencing.

In one embodiment, the system includes cluster the data based on a metric, and display the groupings and the interconnections based on the clusters. The filtering function may be a density estimation function. The metric may be a Pearson correlation.

Additionally, the system can monitor biomarkers for individual diseases such as high blood pressure or diabetes. A biomarker is "a characteristic that is objectively measured and evaluated as an indicator of normal biological processes, pathogenic processes, or pharmacologic responses to a therapeutic intervention." A biomarker may be measured on a biosample (as a blood, urine, or tissue test), it may be a recording obtained from a person (blood pressure, ECG, or Holter), or it may be an imaging test (echocardiogram or CT scan). Biomarkers can indicate a variety of health or disease characteristics, including the level or type of exposure to an environmental factor, genetic susceptibility, genetic responses to exposures, markers of subclinical or clinical disease, or indicators of response to therapy. Thus, a simplistic way to think of biomarkers is as indicators of disease trait (risk factor or risk marker), disease state (preclinical or clinical), or disease rate (progression). 16 Accordingly, biomarkers can be classified as antecedent biomarkers (identifying the risk of developing an illness), screening biomarkers (screening for subclinical disease), diagnostic biomarkers (recognizing overt disease), staging biomarkers (categorizing disease severity), or prognostic biomarkers (predicting future disease course, including recurrence and response to therapy, and monitoring efficacy of therapy). In one embodiment, blood testing is done to determine different components of the immune system as well as lipids and glucose metabolism. An ultrasound image is created by placing a transducer which sends sound waves and receives reflections from inside the body. Those reflections are computerized to recreate a picture of the arteries of the neck. The thickness of the carotid artery called intima-media thickness is a reflection of early cholesterol build-up in the carotid arteries. The ultrasound of the femoral arteries is also done to measure arterial stiffness, a good measure of vascular health. Ultrasound of the abdominal aorta is used to screen for abdominal aortic aneurysms.

The endothelium is the inner lining of blood vessels. The endothelium regulates blood flow and maintains vessel health. Several studies have shown that endothelial dysfunction is a risk factor for cardiovascular disease. Peripheral arterial tonometry is a method to assess endothelial function using a device positioned at the fingertips and a blood pressure cuff (response after deflation of the blood pressure cuff).

An echocardiogram is a diagnostic test which generates images of the heart by bouncing high frequency sound off the structures of the heart and recording the returned echoes and processing them into images. The sound is transmitted and received with a transducer placed upon the chest.

For example, biomarkers for use in distinguishing, or aiding in distinguishing, atherosclerotic subjects from non-atherosclerotic subjects include 3-methylhistidine, p-cresol sulfate, mannose, glucose, and/or gluconate, and combinations thereof. In one aspect biomarkers for use in methods relating to atherosclerosis using plasma samples from a subject include one or more of 3-methylhistidine, p-cresol sulfate, mannose, glucose, gluconate, among others. In one embodiment, cardiovascular disease (CVD) biomarkers are processed by the system. For example, CVD related biomarkers can be tracked such as ADMA, asymmetrical dimethyl arginine; Apo B, apolipoprotein B; CETP, cholesterol ester transfer protein; GPX1, glutathione peroxidase; IL, interleukin; IMT, intimal-medial thickness; Lp(a), lipoprotein a; LpPLA2, lipoprotein-associated phospholipase A2; LV, left ventricle; LVH, LV hypertrophy; MMP, matrix metalloproteinase; MPO, myeloperoxidase; SAA, serum amyloid A; sCD40L, soluble CD40 ligand; sICAM, soluble intercellular adhesion molecule; PAI-1, plasminogen activator inhibitor 1; PET, positron emission tomography; TIMP, tissue inhibitor of matrix metalloproteinases; and TPA, tissue plasminogen activator.

Generally, people with type 1 diabetes present with acute symptoms of diabetes and markedly elevated blood glucose levels. Because of the acute onset of symptoms, most cases of type 1 diabetes are detected soon after symptoms develop. Type 2 diabetes is frequently not diagnosed until complications appear, and approximately one-third of all people with diabetes may be undiagnosed. Individuals at high risk should be screened for diabetes and pre-diabetes. In one embodiment, the system analyzes clinical risk models that include individuals who are overweight (BMI≥25 kg/m2*) and have additional risk factors including: are habitually physically inactive, have a first-degree relative with diabetes, are members of a high-risk ethnic population (e.g., African American, Latino, Native American, Asian American, Pacific Islander), have delivered a baby weighing >9 lb or have been diagnosed with GDM, are hypertensive (>140/90 mmHg), have an HDL cholesterol level <35 mg/dl (0.90 mmol/l) and/or a triglyceride level >250 mg/dl (2.82 mmol/l), have PCOS, on previous testing, had IGT or IFG, have other clinical conditions associated with insulin resistance (e.g., PCOS or acanthosis nigricans), have a history of vascular disease.

The system can monitor urinary protein associated with diabetes mellitus. They include defense proteins (al-antitrypsin, Complement factor H, C3, B, I, C7, 9), Alpha-1-antichymotrypsin precursor, Antithrombin-III, Alpha-2-glycoprotein 1, zinc, Ig gamma 1 chain C region, Alpha and beta-2-microglobulin, Alpha-2-antiplasmin precursor, Vitronectin precursor); Transport (Serotransferrin precursor, Ceruloplasmin precursor, Hemopexin, AMBP protein, Albumin, Haptoglobin precursor, Transthyretin precursor, VDBP); Metabolism (ApoA-1, ApoA-II precursor, Apo-D, Alpha-1B-glycoprotein, Beta-2-glycoprotein 1 precursor, Prostaglandin H2 D-isomerase precursor, Alpha-2-HS-glycoprotein precursor, E-cadherin, Dystroglycan precursor, Fibrinogen beta chain precursor); Signal transduction (Kininogen precursor, B-factor, properdin, Clusterin, Angiotensinogen, Sulfated glycoprotein 2, retinol-binding protein 4, Epidermal growth factor) and cell development protein such as Lumican precursor.

The system can track proteins in human serum of patients having diabetes mellitus such as:

Cytokines and cytokine-related proteins Leptin, TNF-alpha, IL-6

Immune-related proteins MCP-1

Proteins involved in fibrinolytic system PAI-1

Tissue factor

Complement and complement-related proteins Adipsin (complement factor D), ASP, Adiponectin Lipids and proteins for lipid metabolism or transport Lipoprotein lipase (LPL), Apolipoprotein E, Apolipoprotein A1, Apolipoprotein A2, Apolipoprotein B+, Apolipoprotein H, Apolipoprotein C1, C2, NEFAs, Cholesterol ester transferase protein (CETP), Inflammatory proteins C-reactive protein (CRP), α-tumor necrosis factor (αTNF)

Individuals at high risk for developing diabetes are made aware of the many benefits of modest weight loss and participating in regular physical activity. The system can generate recommendations and track patient compliance. Follow-up counseling is important for success and a coach can be assigned to help the patient. Monitoring for the development of diabetes in those with pre-diabetes is performed regularly using mobile fitness devices. The system can also recommend appropriate treatment given for, other CVD risk factors (e.g., tobacco use, hypertension, dyslipidemia). Because of possible side effects and cost, there is insufficient evidence to support the use of drug therapy. An intensive lifestyle modification program has been shown to be very effective (~58% reduction after 3 years). Use of the pharmacologic agents metformin, acarbose, orlistat, and rosiglitazone has also been shown to decrease incident diabetes to various degrees. Of note, however, each of these drugs may cause side effects of varying severity in a small number of individuals.

Physical activity and behavior modification are important components of weight loss programs and are most helpful in maintenance of weight loss. Thus, lifestyle change should be the primary approach to weight loss. The system recommends and monitors structured programs that emphasize lifestyle changes, including education, reduced energy and fat (~30% of total energy) intake, regular physical activity, and regular participant contact to achieve produce long-term weight loss on the order of 5-7% of starting weight. Saturated fat intake should be <7% of total calories. Intake of trans fat should be minimized. The system monitors carbohydrate, whether by carbohydrate counting, exchanges, camera detection or experience-based estimation, for glycemic control.

The methods and systems as disclosed herein may comprise, or comprise the use of, predicting, diagnosing, and/or prognosing a status or outcome of a disease or condition in a subject based on one or more biomedical outputs. Predicting, diagnosing, and/or prognosing a status or outcome of a disease in a subject may comprise diagnosing a disease or condition, identifying a disease or condition, determining the stage of a disease or condition, assessing the risk of a disease or condition, assessing the risk of disease recurrence, assessing reproductive risk, assessing genetic risk to a fetus, assessing the efficacy of a drug, assessing risk of an adverse drug reaction, predicting optimal drug dosage, predicting drug resistance, or a combination thereof.

The samples disclosed herein may be from a subject suffering from a cancer. The sample may comprise malignant tissue, benign tissue, or a mixture thereof. The cancer may be a recurrent and/or refractory cancer. Examples of cancers include, but are not limited to, sarcomas, carcinomas, lymphomas or leukemias.

Additional diseases and/or conditions include, but are not limited to, atherosclerosis, inflammatory diseases, autoimmune diseases, rheumatic heart disease. Examples of inflammatory diseases include, but are not limited to, acne vulgaris, Alzheimer's, ankylosing spondylitis, arthritis (osteoarthritis, rheumatoid arthritis (RA), psoriatic arthritis), asthma, atherosclerosis, celiac disease, chronic prostatitis, Crohn's disease, colitis, dermatitis, diverticulitis, fibromyalgia, glomerulonephritis, hepatitis, irritable bowel syndrome (IBS), systemic lupus erythematous (SLE), nephritis, Parkinson's disease, pelvic inflammatory disease, sarcoidosis, ulcerative colitis, and vasculitis.

Examples of autoimmune diseases include, but are not limited to, acute disseminated encephalomyelitis (ADEM), Addison's disease, agammaglobulinemia, alopecia greata, amyotrophic Lateral Sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behçet's disease, Berger's disease, Bickerstaffs encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressiva, fibrosing alveolitis (or idiopathic pulmonary fibrosis), gastritis, gastrointestinal pemphigoid, giant cell arteritis, glomerulonephritis, Goodpasture's syndrome, Graves' disease, Guillain-Barré syndrome (GBS), Hashimoto's encephalopathy, Hashimoto's thyroiditis, Henoch-Schonlein purpura, herpes gestationis aka gestational pemphigoid, hidradenitis suppurativa, Hughes-Stovin syndrome, hypogammaglobulinemia, idiopathic inflammatory demyelinating diseases, idiopathic pulmonary fibrosis, IgA nephropathy, inclusion body myositis, chronic inflammatory demyelinating polyneuropathy, interstitial cystitis, juvenile idiopathic arthritis aka juvenile rheumatoid arthritis, Kawasaki's disease, Lambert-Eaton myasthenic syndrome, leukocytoclastic vasculitis, Lichen planus, Lichen sclerosus, linear IgA disease (LAD), Lou Gehrig's disease (Also Amyotrophic lateral sclerosis), lupoid hepatitis aka autoimmune hepatitis, lupus erythematosus, Majeed syndrome, Meniere's disease, microscopic polyangiitis, mixed connective tissue disease, morphea, Mucha-Habermann disease, multiple sclerosis, myasthenia gravis, myositis, neuromyelitis optica (also Devic's disease), neuromyotonia, ocular cicatricial pemphigoid, opsoclonus myoclonus syndrome, Ord's thyroiditis, palindromic rheumatism, PANDAS (pediatric autoimmune neuropsychiatric disorders associated with *streptococcus*), paraneoplastic cerebellar degeneration, paroxysmal nocturnal hemoglobinuria (PNH), Parry Romberg syndrome, Parsonage-Turner syndrome, Pars planitis, pemphigus vulgaris, pernicious anemia, perivenous encephalomyelitis, POEMS syndrome, polyarteritis nodosa, polymyalgia rheumatica, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, Schmidt syndrome another form of APS, Schnitzler syndrome, scleritis, scleroderma, serum sickness, Sjögren's syndrome, spondyloarthropathy, Stiff person syndrome, subacute bacterial endocarditis (SBE), Susac's syndrome, Sweet's syndrome, sympathetic ophthalmia, Takayasu's arteritis, temporal arteritis (also known as "giant cell arteritis"), thrombocytopenia, Tolosa-Hunt syndrome, transverse myelitis, ulcerative colitis, undifferentiated connective tissue disease different from mixed connective tissue disease, undifferentiated spondyloarthropathy, urticarial vasculitis, vasculitis, vitiligo, and Wegener's granulomatosis.

The methods and systems as provided herein may also be useful for detecting, monitoring, diagnosing and/or predicting a subject's response to an implanted device. Exemplary medical devices include but are not limited to stents, replacement heart valves, implanted cerebella stimulators, hip replacement joints, breast implants, and knee implants.

The methods and systems as disclosed herein may be used for monitoring the health of a fetus using whole or partial genome analysis of nucleic acids derived from a fetus, as compared to the maternal genome. For example, nucleic acids can be useful in pregnant subjects for fetal diagnostics, with fetal nucleic acids serving as a marker for gender, rhesus D status, fetal aneuploidy, and sex-linked disorders. The methods and systems as disclosed herein may identify fetal mutations or genetic abnormalities. The methods and systems as disclosed herein can enable detection of extra or missing chromosomes, particularly those typically associated with birth defects or miscarriage. The methods and systems as disclosed herein may comprise, or comprise the use of, the diagnosis, prediction or monitoring of autosomal trisomies (e.g., Trisomy 13, 15, 16, 18, 21, or 22) and may be based on the detection of foreign molecules. The trisomy may be associated with an increased chance of miscarriage (e.g., Trisomy 15, 16, or 22). Alternatively, the trisomy that is detected is a live born trisomy that may indicate that an infant may be born with birth defects (e.g., Trisomy 13 (Patau Syndrome), Trisomy 18 (Edwards Syndrome), and Trisomy 21 (Down Syndrome)). The abnormality may also be of a sex chromosome (e.g., XXY (Klinefelter's Syndrome), XYY (Jacobs Syndrome), or XXX (Trisomy X). The methods disclosed herein may comprise one or more genomic regions on the following chromosomes: 13, 18, 21, X, or Y. For example, the foreign molecule may be on chromosome 21 and/or on chromosome 18, and/or on chromosome 13. The one or more genomic regions may comprise multiple sites on multiple chromosomes.

Further fetal conditions that can be determined based on the methods and systems herein include monosomy of one or more chromosomes (X chromosome monosomy, also known as Turner's syndrome), trisomy of one or more chromosomes (13, 18, 21, and X), tetrasomy and pentasomy of one or more chromosomes (which in humans is most commonly observed in the sex chromosomes, e.g., XXXX, XXYY, XXXY, XYYY, XXXXX, XXXXY, XXXYY, XYYYY and XXYYY), monoploidy, triploidy (three of every chromosome, e.g., 69 chromosomes in humans), tetraploidy (four of every chromosome, e.g., 92 chromosomes in humans), pentaploidy and multiploidy.

The methods and systems as disclosed may comprise detecting, monitoring, quantitating, or evaluating one or more pathogen-derived nucleic acid molecules or one or more diseases or conditions caused by one or more pathogens. Exemplary pathogens include, but are not limited to, *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio*, or *Yersinia*. Additional pathogens include, but are not limited to, *Mycobacterium tuberculosis, Streptococcus, Pseudomonas, Shigella, Campylobacter*, and *Salmonella*.

The disease or conditions caused by one or more pathogens may comprise tuberculosis, pneumonia, foodborne illnesses, tetanus, typhoid fever, diphtheria, syphilis, leprosy, bacterial vaginosis, bacterial meningitis, bacterial pneumonia, a urinary tract infection, bacterial gastroenteritis, and bacterial skin infection. Examples of bacterial skin infections include, but are not limited to, impetigo which may be caused by *Staphylococcus aureus* or *Streptococcus pyogenes*; erysipelas which may be caused by a *streptococcus* bacterial infection of the deep epidermis with lymphatic spread; and cellulitis which may be caused by normal skin flora or by exogenous bacteria.

The pathogen may be a fungus, such as, *Candida, Aspergillus, Cryptococcus, Histoplasma, Pneumocystis*, and *Stachybotrys*. Examples of diseases or conditions caused by a fungus include, but are not limited to, jock itch, yeast infection, ringworm, and athlete's foot.

The pathogen may be a virus. Examples of viruses include, but are not limited to, adenovirus, coxsackievirus, Epstein-Barr virus, Hepatitis virus (e.g., Hepatitis A, B, and C), herpes simplex virus (type 1 and 2), cytomegalovirus, herpes virus, HIV, influenza virus, measles virus, mumps virus, papillomavirus, parainfluenza virus, poliovirus, respiratory syncytial virus, rubella virus, and varicella-zoster virus. Examples of diseases or conditions caused by viruses include, but are not limited to, cold, flu, hepatitis, AIDS, chicken pox, rubella, mumps, measles, warts, and poliomyelitis.

The pathogen may be a protozoan, such as *Acanthamoeba* (e.g., *A. astronyxis, A. castellanii, A. culbertsoni, A. hatchetti, A. polyphaga, A. rhysodes, A. healyi, A. divionensis*), *Brachiola* (e.g., *B. connori, B. vesicularum*), *Cryptosporidium* (e.g., *C. parvum*), *Cyclospora* (e.g., *C. cayetanensis*), *Encephalitozoon* (e.g., *E. cuniculi, E. hellem, E. intestinalis*), *Entamoeba* (e.g., *E. histolytica*), *Enterocytozoon* (e.g., *E. bieneusi*), *Giardia* (e.g., *G. lamblia*), *Isospora* (e.g, *I. belli*), *Microsporidium* (e.g., *M. africanum, M. ceylonensis*), *Naegleria* (e.g., *N. fowleri*), *Nosema* (e.g., *N. algerae, N. ocularum*), *Pleistophora, Trachipleistophora* (e.g., *T. anthropophthera, T. hominis*), and *Vittaforma* (e.g., *V. corneae*).

The methods and systems as disclosed herein may comprise, or comprise the use of, treating and/or preventing a disease or condition in a subject based on one or more biomedical outputs. The one or more biomedical outputs may recommend one or more therapies. The one or more biomedical outputs may suggest, select, designate, recommend or otherwise determine a course of treatment and/or prevention of a disease or condition. The one or more biomedical outputs may recommend modifying or continuing one or more therapies. Modifying one or more therapies may comprise administering, initiating, reducing, increasing, and/or terminating one or more therapies. The one or more therapies comprise an anti-cancer, antiviral, antibacterial, antifungal, immunosuppressive therapy, or a combination thereof. The one or more therapies may treat, alleviate, or prevent one or more diseases or indications.

Examples of anti-cancer therapies include, but are not limited to, surgery, chemotherapy, radiation therapy, immunotherapy/biological therapy, photodynamic therapy. Anti-cancer therapies may comprise chemotherapeutics, monoclonal antibodies (e.g., rituximab, trastuzumab), cancer vaccines (e.g., therapeutic vaccines, prophylactic vaccines), gene therapy, or combination thereof.

The one or more therapies may comprise an antimicrobial. Generally, an antimicrobial refers to a substance that kills or inhibits the growth of microorganisms such as bacteria, fungi, virus, or protozoans. Antimicrobial drugs either kill microbes (microbicidal) or prevent the growth of microbes (microbiostatic). There are mainly two classes of antimicrobial drugs, those obtained from natural sources (e.g., antibiotics, protein synthesis inhibitors (such as aminoglycosides, macrolides, tetracyclines, chloramphenicol, polypeptides)) and synthetic agents (e.g., sulphonamides, cotrimoxazole, quinolones). In some instances, the antimicrobial drug is an antibiotic, anti-viral, anti-fungal, anti-malarial, anti-tuberculosis drug, anti-leprotic, or anti-protozoal.

Antibiotics are generally used to treat bacterial infections. Antibiotics may be divided into two categories: bactericidal antibiotics and bacteriostatic antibiotics. Generally, bactericidals may kill bacteria directly where bacteriostatics may prevent them from dividing. Antibiotics may be derived from living organisms or may include synthetic antimicrobials, such as the sulfonamides. Antibiotics may include aminoglycosides, such as amikacin, gentamicin, kanamycin, neomycin, netilmicin, tobramycin, and paromomycin. Alternatively, antibiotics may be ansamycins (e.g., geldanamycin, herbimycin), cabacephems (e.g., loracarbef), carbapenems (e.g., ertapenem, doripenem, imipenem, cilastatin, meropenem), glycopeptides (e.g., teicoplanin, vancomycin, telavancin), lincosamides (e.g., clindamycin, lincomycin, daptomycin), macrolides (e.g., azithromycin, clarithromycin, dirithromycin, erythromycin, roxithromycin, troleandomycin, telithromycin, spectinomycin, spiramycin), nitrofurans (e.g., furazolidone, nitrofurantoin), and polypeptides (e.g., bacitracin, colistin, polymyxin B).

In some instances, the antibiotic therapy includes cephalosporins such as cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, and ceftobiprole.

The antibiotic therapy may also include penicillins. Examples of penicillins include amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, temocillin, and ticarcillin.

Alternatively, quinolines may be used to treat a bacterial infection. Examples of quinilones include ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin.

In some instances, the antibiotic therapy comprises a combination of two or more therapies. For example, amoxicillin and clavulanate, ampicillin and sulbactam, piperacillin and tazobactam, or ticarcillin and clavulanate may be used to treat a bacterial infection.

Sulfonamides may also be used to treat bacterial infections. Examples of sulfonamides include, but are not limited to, mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxazole (co-trimoxazole) (tmp-smx).

Tetracyclines are another example of antibiotics. Tetracyclines may inhibit the binding of aminoacyl-tRNA to the mRNA-ribosome complex by binding to the 30S ribosomal subunit in the mRNA translation complex. Tetracyclines include demeclocycline, doxycycline, minocycline, oxytetracycline, and tetracycline. Additional antibiotics that may be used to treat bacterial infections include arsphenamine, chloramphenicol, fosfomycin, fusidic acid, linezolid, metronidazole, mupirocin, platensimycin, quinupristin/dalfopristin, rifaximin, thiamphenicol, tigecycline, tinidazole, clofazimine, dapsone, capreomycin, cycloserine, ethambutol, ethionamide, isoniazid, pyrazinamide, rifampicin, rifamycin, rifabutin, rifapentine, and streptomycin.

Antiviral therapies are a class of medication used specifically for treating viral infections. Like antibiotics, specific antivirals are used for specific viruses. They are relatively harmless to the host, and therefore can be used to treat infections. Antiviral therapies may inhibit various stages of the viral life cycle. For example, an antiviral therapy may inhibit attachment of the virus to a cellular receptor. Such antiviral therapies may include agents that mimic the virus associated protein (VAP and bind to the cellular receptors. Other antiviral therapies may inhibit viral entry, viral uncoating (e.g., amantadine, rimantadine, pleconaril), viral synthesis, viral integration, viral transcription, or viral translation (e.g., fomivirsen). In some instances, the antiviral therapy is a morpholino antisense. Antiviral therapies should be distinguished from viricides, which actively deactivate virus particles outside the body.

Many of the antiviral drugs available are designed to treat infections by retroviruses, mostly HIV. Antiretroviral drugs may include the class of protease inhibitors, reverse transcriptase inhibitors, and integrase inhibitors. Drugs to treat HIV may include a protease inhibitor (e.g., invirase, saquinavir, kaletra, lopinavir, lexiva, fosamprenavir, norvir, ritonavir, prezista, duranavir, reyataz, viracept), integrase inhibitor (e.g., raltegravir), transcriptase inhibitor (e.g., abacavir, ziagen, agenerase, amprenavir, aptivus, tipranavir, crixivan, indinavir, fortovase, saquinavir, Intelence™, etravirine, isentress, viread), reverse transcriptase inhibitor (e.g., delavirdine, efavirenz, epivir, hivid, nevirapine, retrovir, AZT, stuvadine, truvada, videx), fusion inhibitor (e.g., fuzeon, enfuvirtide), chemokine coreceptor antagonist (e.g., selzentry, emtriva, emtricitabine, epzicom, or trizivir). Alternatively, antiretroviral therarapies may be combination therapies, such as atripla (e.g., efavirenz, emtricitabine, and tenofovira disoproxil fumarate) and completer (emtricitabine, rilpivirine, and tenofovir disoproxil fumarate). Herpes viruses, best known for causing cold sores and genital herpes, are usually treated with the nucleoside analogue acyclovir. Viral hepatitis (A-E) are caused by five unrelated hepatotropic viruses and are also commonly treated with antiviral drugs depending on the type of infection. Influenza A and B viruses are important targets for the development of new influenza treatments to overcome the resistance to existing neuraminidase inhibitors such as oseltamivir.

In some instances, the antiviral therapy may comprise a reverse transcriptase inhibitor. Reverse transcriptase inhibitors may be nucleoside reverse transcriptase inhibitors or non-nucleoside reverse transcriptase inhibitors. Nucleoside reverse transcriptase inhibitors may include, but are not limited to, combivir, emtriva, epivir, epzicom, hivid, retrovir, trizivir, truvada, videx ec, videx, viread, zerit, and ziagen. Non-nucleoside reverse transcriptase inhibitors may comprise edurant, intelence, rescriptor, sustiva, and viramune (immediate release or extended release).

Protease inhibitors are another example of antiviral drugs and may include, but are not limited to, agenerase, aptivus, crixivan, fortovase, invirase, kaletra, lexiva, norvir, prezista, reyataz, and viracept. Alternatively, the antiviral therapy may comprise a fusion inhibitor (e.g., enfuviride) or an entry inhibitor (e.g., maraviroc).

Additional examples of antiviral drugs include abacavir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, fusion inhibitors, ganciclovir, ibacitabine, immunovir, idoxuridine, imiquimod, indinavir, inosine, integrase inhibitor, interferons (e.g., interferon type I, II, III), lamivudine, lopinavir, loviride, maraviroc, moroxydine, methisazone, nelfinavir, nevirapine, nexavir, nucleoside analogues, oseltamivir, peginterferon alfa-2a, penciclovir, peramivir, pleconaril, podophyllotoxin, protease inhibitors, raltegravir, reverse transcriptase inhibitors, ribavirin, rimantadine, ritonavir, pyramidine, saquinavir, stavudine, tea tree oil, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

An antifungal drug is medication that may be used to treat fungal infections such as athlete's foot, ringworm, candidiasis (thrush), serious systemic infections such as cryptococcal meningitis, and others. Antifungals work by exploiting differences between mammalian and fungal cells to kill off the fungal organism. Unlike bacteria, both fungi and humans are eukaryotes. Thus, fungal and human cells are similar at the molecular level, making it more difficult to find a target for an antifungal drug to attack that does not also exist in the infected organism.

Antiparasitics are a class of medications which are indicated for the treatment of infection by parasites, such as nematodes, cestodes, trematodes, infectious protozoa, and amoebae. Like antifungals, they must kill the infecting pest without serious damage to the host.

Various dietary chemicals act on the human genome, either directly or indirectly, to alter gene expression or structure. Nutrients may act directly as ligands for transcription factor receptors; may be metabolized by primary or secondary metabolic pathways, thereby altering concentrations of substrates or intermediates involved in gene regulation or cell signaling; or alter signal transduction pathways and signaling. The degree to which diet influences the balance between healthy and disease states depends on an individual's genetic makeup. The system includes monitoring nutrigenomics and metabolomics using mass spectroscopic techniques to identify multiple analytes in parallel and detect gene expression in response to an environment.

In one embodiment, proteomics workflows identify the proteins in a sample. In shotgun proteomics, the sample's proteins are solubulized and digested into short peptides of 10-20 amino-acids using a proteolytic enzyme. The resulting peptide mixture is separated in time according to the peptides' physical and chemical properties using liquid chromatography and analyzed in real-time by the mass-spectrometer. As the peptides with similar physicochemical properties elute from the column, the mass spectrometer acquires survey scans to identify and select the most abundant peptide ions for analysis by tandem mass-spectrometry. Mass spectrometry measures the mass of molecules and atoms. The molecules to be analyzed are transformed into charged, gas-phase ions which can be manipulated and detected by the mass spectrometer. One embodiment is a quantum dot mass spectrometer with an array of different dots each filtering specific wavelengths of light. Each dot only lets through a certain wavelength of light and the dots are so small they can be printed onto a thin film and can be placed on top of a camera or they can be deposited onto each camera pixel sensor.

Various open-source and commercial tandem mass-spectrometry search engines can be used including Mascot from company Matrix Science, and SEQUEST available from Thermo Fisher, or open source software such as X!Tandem and OMSSA. The automated acquisition of tandem mass spectra in conjunction with liquid-chromatography can be done, and tandem mass-spectrometry search engines analyze these shotgun proteomics datasets to identify the sample's proteins. The search engines match the tandem mass spectra with peptide sequences from a protein sequence database and use the identified peptides to infer the protein content of the sample. A mass analyzer uses electrical, magnetic, and RF fields to separate the gas-phase ions in time or space before they are counted and detected.

The system recommends dietary intervention based on knowledge of nutritional requirement, nutritional status, and genotype (i.e., "individualized nutrition") can be used to prevent, mitigate or cure chronic disease. In another preferred embodiment the physiological data includes epigenetic data, genetic data, genomic data, and nutrigenomic data. In a further preferred embodiment, the physiological data comprises measurements of heart rate, breathing rate and volume and blood pressure. In a still further preferred embodiment, the physiological data includes measurements of weight, BMI, HDL, LDL, cholesterol, glucose, lipids, HbAlc, blood pressure, biomarkers of inflammation, TNF-α, HsCRP, leukotrienes, prostaglandins, and hormones. In a more preferred embodiment, the hormones comprise insulin, glucagon, and leptins. In another preferred embodiment the physiological data is collected before and after consumption of a food item. In a yet further preferred embodiment the disease or disorder is selected from type 2 diabetes, mellitus (T2DM), obesity, metabolic syndrome, Alzheimer's disease, cardiovascular disease, and cancer. In a most preferred embodiment, the disease or disorder is type 2 diabetes mellitus.

For coronary syndromes, potential biomarkers include the following:

| Plaque | Unstable plaque | Plaque rupture | Thrombosis | Ischemia | Necrosis | LV re-modeling |
|---|---|---|---|---|---|---|
| LDL | MMP-9 | sCD40L | PAI-1 | IMA | cTNT | BNP |
| αx LDL | MPO | PIGF | sCD40L | FFA | cTNI | NT-ProBNP |
| CRP | ICAM | PAPP-A | VwF | Choline | CK-MB | ProBNP |
| IL-6 | VCAM | VCAM | D-dimer | BNP | Myg | MMP |
| IL-10 | | | | | ?IL-6/TF | |
| IL-18 | | | | | | |
| Fbg | | | | | | |
| TNF-_ | | | | | | |

Biomarkers that may be elevated at each phase of coronary disease are displayed in the above sequence, where sCD40L indicates soluble CD40 ligand; Fbg, fibrinogen; FFA, free fatty acid; ICAM, intercellular adhesion molecule; IL, interleukin; IMA, ischemia modified albumin; MMP, matrix metalloproteinases; MPO, myeloperoxidase; Myg, myoglobin; NT-proBNP, N-terminal proBNP; Ox-LDL, oxidized low-density lipoprotein; PAI-1, plasminogen activator inhibitor; PAPP-A, pregnancy-associated plasma protein-A; PIGF, placental growth factor; TF, tissue factor; TNF, tumor necrosis factor; TNI, troponin I; TNT, troponin T; VCAM, vascular cell adhesion molecule; and VWF, von Willebrand factor.

In the following example, an exemplary process for providing interoperability between a device within the base station network (and an external device at a clinic or hospital is described. Pseudo-code for the device interoperability process is as follows:

Hospital/Clinic devices and In-Network devices requests registration with remote server (S42)
Remote server forwards registration request to all base stations, which in turn register hospital/clinic device (S44)
Hospital device requests application data from server, which in turn forwards request to base station (S46)
Base station searches for a responsive device from its registration list and forwards request to responsive device over preferred communication channel (S48)
Responsive device replies to base station with data (S50)
Base station reformats data to match requestor's preference (S52)
Base station forwards formatted data to hospital/clinic device through the remote server (S54)

In this example, a doctor at a hospital, clinic or doctor office registers and authenticates with the remote server. In a thin-client application, the server maintains all patient information in its database. Upon authentication, the server polls the base station for the latest information and displays the patient screens for the doctor. In this case, the server uses secure HTTP (SHTTP) protocol for communication with the base station and the base station performs auto-translation among devices. For example, a hospital EKG device can store time series EKG data in XML format, while a home based EKG device can store compressed EKG data. The base station can translate the Open EKG format to the uncompressed XML data.

In another embodiment, instead of having the doctor using a thin-client, a remote user such as a patient representative (attorney in fact), family member, or a doctor can be running his/her own computer system that is registered with the server 200 as an authorized user. The server 200 forwards such registration to the base station and the base station registers the doctor's computer as an authorized doctor base station in the network. The doctor base station in turn communicates with devices in the doctor's office such as digital scales, blood pressure measurement devices, digital X-ray machines, glucose measurement devices, digital scanners such as computer aided tomography (CAT) scanners and nuclear magnetic resonance (NMR) scanners, among others. These devices capture patient information through a unique patient identifier and the data is stored in the doctor base station and can also be uploaded to the remote server 200 to store data. Since numerous base stations can exist that provide medical information on a patient (different doctors/specialists, different hospitals and care centers), the server performs data synchronization to ensure that all base stations have access to the latest information.

To allow the remote person such as a physician or a family member to monitor a patient, a plurality of user interface modules enable the remote person to control each appliance and to display the data generated by the appliance. In one example scenario, an EKG sensor wirelessly communicates with the patient base station and outputs a continuous EKG waveform. A pattern recognizer or analyzer positioned at the doctor's station accepts waveform data and generates a variety of statistics that characterize the waveform and can generate alarms or messages to the doctor if certain predefined conditions are met. While it is operating, the EKG sends its waveform data to its subscribing components or modules at the doctor's office and the analyzer processes the data and sends summaries or recommendations to the doctor for viewing. If, during the operation of this network of components, any of these components experience an event that compromises its ability to support the protocol (e.g., the EKG unit is disconnected or deactivated from the base station), then the affected components notify the remote base station of a disconnected appliance. When finished with the EKG data sampling, the user may "deselect" the device on the user interface framework, which results in the EKG user interface module being disabled and terminating data collection by the EKG device. In turn, the protocol instructs each of the leased components to terminate its subscriptions. The protocol then notifies the registry that it is vacating its lease on these components and tells the user interface event handler that it is ending.

The system can support procedure-centric workflow management such as those described in Application Serial No. 20060122865. In one example, the system manages a workflow involving a specialist, an electronic medical record (EMR) or other external patient information system, a referring provider, a rural health care facility, and appropriate appliances (e.g., modalities) corresponding to the particular procedure of interest. In one example, the specialist's workflow includes capturing/reviewing patient history, which itself entails reviewing prior procedures, reviewing prior data and/or digital images, reviewing problem lists in communication with the EMR, capturing/reviewing patient physical and history information in communication with EMR, and reviewing lab results in communication with EMR. The workflow further includes capturing follow-up orders in communication with EMR. In addition, the workflow also involves capturing procedure results and corresponding data obtained during the procedure, and distributing such data in communication with a referring provider and rural facility. Finally, in communication with external devices or appliances, the specialist receives the captured data from the procedure and reviews/interprets the data or digital images. Workflow management as described here includes recognition of various roles of people involved in workflows, whether they are different types of caregivers or different types of patients.

In one embodiment, the authentication source is a trusted key distribution center (KDC) and the authentication type is user IDs with passwords. The initial authentication can also be based on public key. The public key infrastructure (PKI) system can be used where the authentication source is a certificate authority (CA) and the authentication type is challenge/response. Another authentication system called the secure remote password (SRP) protocol authenticates clients to servers securely, in cases where the client must memorize a small secret (like a password) and carries no other secret information, and where the server carries a verifier which allows it to authenticate the client but which, if compromised, would not allow someone to impersonate the client.

In one embodiment, a device first appears on a network. The device searches the local cache for information regarding the base station. If base station information is found, the device attempts to contact the base station and setup a connection. Otherwise if the information is not found, then a discovery request is sent. The discovery request may be sent via a broadcast or a multicast. In this regard, the device sends out a discovery request and all the devices in the network neighborhood should receive the message and respond appropriately. The device agent examines the responses to determine and/or confirm the base station. If the device does not discover the base station, the system assumes that there is no base station in the network neighborhood at present and repeats the discovery request process until a base station is found. Otherwise, if the device discovers the base station, the connection token is saved (an XML message that tells where the device communicator is located and how to contact it) in the cache for later usage. The cache may allow for faster discovery but it may also expire due to the feature that devices may join and leave the network. Therefore a time-to-live (TTL) may be attached so that after a certain period the cached data may be considered expired. A check may also be preformed to ensure that the device exists before a network connection is initiated. To provide a generalized format, XML may be used to provide an easily expandable and hierarchical representation. XML may also be used to aggregate information from other agents and send back results from service providers to device through the base station.

A multitude of standards address mid to high data rates for voice, PC LANs, video, among others. ZigBee provides good bandwidth with low latency and very low energy consumption for long battery lives and for large device arrays. Bluetooth provides higher speed (and higher power consumption) for cell phone headset applications, among others. Variants of the 802.11 standard (802.11b, 802.11g, 802.11a) provide yet faster data transmission capability with correspondingly high power consumption. Other devices include WiMAX (802.16) and ultrawideband devices that are very high in power consumption and provide long range and/or video capable transmission.

Device discovery and service discovery are provided for each class of devices (Zigbee or Bluetooth, for example). For interoperability, a local discovery mapper running on the personal server or a remote discovery mapper running on a remote server is provided to enable Zigbee services to be advertised to Bluetooth devices and vice versa, for example. In other implementations, the services of ZigBee devices can be advertised to body PAN devices (PAN devices that are attached to a biological being such as humans or pets), Bluetooth devices, cellular devices, UWB devices, WiFi, and WiMAX devices, among others.

The appliances can communicate data conforming to the interoperable format over one of: cellular protocol, ZigBee protocol, Bluetooth protocol, WiFi protocol, WiMAX protocol, USB protocol, ultrawideband protocol. The appliances can communicate over two or more protocols. The first medical appliance can transmit the first vital information over a first protocol (such as Bluetooth protocol) to a computer, wherein the computer transmits the first vital information to the second medical appliance over a second protocol (such as ZigBee protocol). The computer can then transmit to a hospital or physician office using broadband such as WiMAX protocol or cellular protocol. The computer can perform the interoperable format conversion for the appliances or devices, or alternatively each appliance or device can perform the format conversion. Regardless of which device performs the protocol conversion and format conversion, the user does not need to know about the underlying format or protocol in order to use the appliances. The user only needs to plug an appliance into the network, the data transfer is done automatically so that the electronic "plumbing" is not apparent to the user. In this way, the user is shielded from the complexity supporting interoperability.

Another exemplary process for monitoring a patient is discussed next. The process starts with patient registration (1000) and collection of information on patient (1002). Next, the process selects a treatment template based on treatment plan for similar patients (1004). The process generates a treatment plan from the template and customizes the treatment plan (1006). The system considers the following factors: medical condition, amount of weight to lose, physician observations regarding mental state of the patient.

In the event the patient has extensive or contraindicating medical history or information, the system alerts the doctor to manually review the patient file and only generate recommendations with authorization from a doctor.

The doctor subsequently reviews and discusses the customized plan with the patient. In one embodiment, during the discussion, the doctor offers the patient the opportunity to enroll in the automated monitoring program. For a monthly or yearly fee, the system would provide the patient with periodic encouragements or comments from the system or the physician. In one embodiment, the doctor can provide the patient with an optional monitoring hardware that measures patient activity (such as accelerometers) and/or vital signs (such as EKG amplifiers).

Upon user enrollment, the system's workflow helps the doctor with setting goals with the patient, establishing a bond of trust and loyalty, and providing positive feedback for improving compliance. Loyalty to the practitioner initially produces higher compliance, emphasizing that establishing a close relationship helps. By providing rapid feedback through instant messaging or emails, the system helps doctors earn the patient's respect and trust, set goals together with the patient, and praise progress when it occurs.

Once enrolled, the system collects data on patient compliance with a treatment plan (1008). This can be done using mobile devices with sensors such as MEMS devices including accelerometer and others as described more fully below. Alternatively, the system periodically requests patient data will be weighed, measured, body fat calculated, blood pressure, resting heart rate and overall well-being. In one embodiment, the system provides a daily (7 days a week) counseling process using texting, email or social network communications.

The process also accumulates reward points for patient to encourage healthy activities, such as jogging, walking, or gardening (1010). The process also compares patient progress with other patients (1012) and sends automatic encouraging messages to patients (1014). Upon patient authorization, the system announces the patient's goals and progress to a social network such as Facebook. The social network strengthens the patient's will for dieting and exercise by the "extent to which individuals perceive that significant others encourage choice and participation in decision-making, provide a meaningful rationale, minimize pressure, and acknowledge the individual's feelings and perspectives." The system supplements the treatment through social supports at home and encourages the patient to make their family and close friends aware of their condition and the expectations of diet and exercise. This will provide the patient with encouragement and accountability.

Periodically, the system shows patient status to doctor (1016) and presents recommendations to doctor on preventive steps, such as check-ups and basic blood tests (1018). Automatically, the system schedules in person consultation for patient and doctor (1020). Captured progress data can be viewed by the physicians and patients using a web based system. The physician can review all interactions between the system and the patient. The physician is able to see their progress reports, interactive e mail which includes daily menus and notes between the service and the patient. The physician will be able to check on the patient's progress at any time of day or night. The system improves the Doctor-Patient relationship and influences compliance.

The system's interactive behavior combines four key elements: just-in-time information, automation in checking with patients, persuasive techniques or messaging, and user control elements. In one embodiment, reports about the user's calorie consumption and exercise activity over time, and in comparison to similarly situated people, are generated.

The system provides meaningful feedback, allowing customers to "see" their food consumption, exercise and the impact of changes. When calories from eating go up between months, a graph depicts so and by how much. Without the system's report to conveniently compare food consumption and exercise from one week to the next, it would be much harder to track those changes. Feedback provides the information crucial to bring about self-awareness of one's actions.

Additionally, the greater value of the system is that it provides useful information about what other similar users' actions and impacts are like. The report shows where the patient's energy intake and outtake are in comparison to the healthiest and the average person. This information serves as a descriptive norm, letting customers know where they are in the spectrum of average and healthy people. When customers see that they are below or even just above average, they want to move "up" on the exercise but reduce their calorie intake. As humans, users are programmed to want to be unique . . . but not too unique—they want to have "normal" food consumption and normal health.

With regard to the message persuasiveness, content is positive and targeted to the user's specific situation. The system provides action opportunities with its reports. If the user is mildly overweight, it might offer a suggestion of having salad with a low calorie dressing for dinner. One embodiment provides a "marketplace" concept, which means that the suggestion would be accompanied by, say, a coupon for salad at a local restaurant. In one embodiment, the system has prior relationships with partners such as restaurants that would offer meals with preset calorie and can send the user coupons to different partners on different days, thus providing users with a wide range of healthy food selections. The system's power lies in its ability to simultaneously prep individuals for action and give them an easy opportunity to do so.

In sum, the system's feedback is effective because:

It is provided frequently, as soon after the consumption behavior as possible.

It is clearly and simply presented.

It is customized to the patient's specific medical condition.

It is provided relative to a meaningful standard of comparison.

It is provided over an extended period of time.

It includes specific food consumption and calorie breakdown.

It is interactive through instant messaging, email, or social networks.

In one embodiment, body analysis data is determined from enrollment data, and include: body mass ratio, pounds of lean muscle mass, percentage of body fat and an optimal range for the specific individual of that percentage, pounds of body fat and an optimal range of body fat for that specific individual, and suggested pounds of body fat to lose. The body analysis includes the following: Basal Metabolic Rate (BMR) is the number of calories burned by the patient's lean body mass in a 24 hour period at complete rest using formulas such as the Harris-Benedict formula or other suitable formulas. Specific Dynamic Action of Foods (SDA) is the numbers of calories required to process and utilize consumed foods (in one case estimated at 5-15% of BMR, depending on personalization). Resting Energy Expenditure (REE) is the sum of BMR and SDA and represents the number of calories that the patient's body requires in a 24 hour period at complete rest. The system determines a Program Recommendation Total Caloric Intake as the caloric supplement required to achieve weight loss of approximately 2 pounds per week. Medications or stimulating substances (such as caffeine, gingsen, or diethylpropion) to assist in weight loss may be recommended and if so the program increases calorie consumption based on a model of the patient's response to such substances.

In one embodiment using the optional mobile monitoring hardware, the system determines Activities of Daily Living (ADL) as the number of calories burned by the patient's body during normal daily activities using accelerometers. The accelerometers can also determine the Calories Burned by Exercise as the number of calories burned by the exercises selected by the patient. Also included, is the level and intensity of the patient's activities. In one embodiment without the optional mobile monitoring hardware, the system approximates the Activities of Daily Living (ADL) as an average of calories expected to be burned by the patient's body during normal daily activities, and in one case is estimated at 20% or REE. The system can also receive averaged approximations of Calories Burned by Exercise is the number of calories burned by the exercises selected by the patient. Also included, is the level and intensity of the patient's activities.

An exemplary process for monitoring patient food intake is discussed next. The process first determines and recommends optimal diet based on patient parameters (1030). To monitor progress, the process takes user entered calorie data and optionally captures images of meals using a mobile device such as a mobile camera (1032). The process then translates images of the meals into calories (1034). The patient's actual diet is then compared to with the recommended diet (1036).

In one embodiment, the camera captures images of the food being served to the patient. The image is provided to an image search system such as the Google image search engine, among others. The search returns the likely type of food in the dish, and an estimation of the container volume is done. In one embodiment, the volume can be done using a 3D reconstruction using two or more images of the food found as the intersection of the two projection rays (triangulation). The two images from the 2D images are selected to form a stereo pair and from dense sets of points, correspondences between the two views of a scene of the two images are found to generate a 3D reconstruction is done to estimate the 3D volume of each food item.

The system determines and looks up a database that contains calorie per unit volume for the dish being served, and multiplies the food volume estimate with the calorie per unit volume for the type of food to arrive at the estimated total calorie for the dish. The user is presented with the estimate and the details of how the estimation was arrived at are shown so the user can correct the calorie estimation if needed.

Next is an exemplary exercise recommendation and monitoring process. First, the process determines and recommends an exercise routine that is customized to the patient's medical condition (1040). The process then captures patient exercise activity using micro-electromechanical systems (MEMS) sensors (1042). The MEMS sensors can include Accelerometer, Gyroscope, Magnetometer, Pressure sensor, Temperature, and Humidity sensor, among others. The process then correlates actual patient activity with the recommended exercises (1044).

An exemplary process for applying the power of social networking to health is discussed next. The process collects data from crowd (1050). The process then compares the performance of the patient with similar patients (1052). The process engages and motivates through Social Network Encouragement (1054).

The system or method described herein may be deployed in part or in whole through a machine that executes software programs on a server such as server, domain server, Internet server, intranet server, and other variants such as secondary server, host server, distributed server, or other such computer or networking hardware on a processor. The processor may be a part of a server, client, network infrastructure, mobile computing platform, stationary computing platform, or other computing platform. The processor may be any kind of computational or processing device capable of executing program instructions, codes, binary instructions or the like that may directly or indirectly facilitate execution of program code or program instructions stored thereon. In addition, other devices required for execution of methods as described in this application may be considered as a part of the infrastructure associated with the server.

The system or method described herein may be deployed in part or in whole through network infrastructures. The network infrastructure may include elements such as computing devices, servers, routers, hubs, firewalls, clients, wireless communication devices, personal computers, communication devices, routing devices, and other active and passive devices, modules or components as known in the art. The computing or non-computing device(s) associated with the network infrastructure may include, apart from other components, a storage medium such as flash memory, buffer, stack, RAM, ROM, or the like. The processes, methods, program codes, and instructions described herein and elsewhere may be executed by the one or more network infrastructural elements.

What is claimed is:

1. A system, comprising:
 a mirror;
 an augmented reality display disposed as part of the mirror to convey digital information and images during an active period;
 a multi-spectral module in the mirror including a video camera and an infrared camera to determine a body shape or dimension for a user;
 a high definition video camera in the mirror, the high definition video camera capturing images of the user and one or more items worn or in contact with the user;
 a wearable heart rate sensor and a temperature sensor worn by the user; and
 a processor coupled to the augmented reality display; and a genetic sequencer or mass spectrometer.

2. The system of claim 1, wherein the high definition video camera captures skin condition.

3. The system of claim 1, wherein the high definition video camera includes an extension to view throat structure, ear structure or nose structure.

4. The system of claim 1, comprising a thermometer, a scale and a blood pressure measurement device coupled to the processor.

5. The system of claim 1, wherein the genetic sequencer or the mass spectrometer analyzes DNA materials.

6. The system of claim 5, wherein the genetic sequencer or mass spectrometer analyzes omic data from urine, stool, sweat, saliva, tear, or bodily fluid.

7. The system of claim 5, wherein the genetic sequencer or mass spectrometer analyzes cell-free DNA.

8. The system of claim 1, wherein the genetic sequencer or the mass spectrometer analyzes omic data from urine, stool, sweat, saliva, tear, or bodily fluid; and wherein the processor executes code to predict a health condition.

9. The system of claim 8, wherein the processor analyzes omic data and health data over a period of time.

10. The system of claim 1, comprising a processor configured to communicate with a pharmacy, a hospital, an ambulance, or a health provider.

11. The system of claim 1, comprising a processor configured for Medical Records Interface and Access to Personal Health Record (PHR) and Electronic Medical Record (EMR) and for rule-based care planning or rule-based education.

12. The system of claim 1, comprising a Thermometer, an Otoscope, an Oximeter, a Stethoscope, a Blood Pressure Sensor, an EKG sensor, a Spirometer, and a Blood Glucose sensor.

13. The system of claim 1, comprising a scale built into a seat or a floor for measuring weight.

14. The system of claim 1, wherein the processor receives voice or video instructions from a remote professional.

15. The system of claim 1, comprising a blood analyzer to characterize the blood, wherein the processor executes code to predict a health condition.

16. The system of claim 1 configured to collect data for a population.

17. The system of claim 16, comprising a processor configured to analyze health at a population level.

18. The system of claim 16, comprising a processor configured to analyze population data spatially at a predetermined location or temporally over a period of time.

* * * * *